United States Patent
Ohyu

(10) Patent No.: US 11,942,212 B2
(45) Date of Patent: Mar. 26, 2024

(54) MEDICAL DATA PROCESSING APPARATUS, MEDICAL DATA PROCESSING METHOD, AND NON-TRANSITORY COMPUTER MEDIUM STORING COMPUTER PROGRAM

(71) Applicant: CANON MEDICAL SYSTEMS CORPORATION, Otawara (JP)

(72) Inventor: Shigeharu Ohyu, Yaita (JP)

(73) Assignee: CANON MEDICAL SYSTEMS CORPORATION, Otawara (JP)

(*) Notice: Subject to any disclaimer, the term of this patent is extended or adjusted under 35 U.S.C. 154(b) by 392 days.

(21) Appl. No.: 17/468,277

(22) Filed: Sep. 7, 2021

(65) Prior Publication Data

US 2021/0407655 A1    Dec. 30, 2021

Related U.S. Application Data

(63) Continuation of application No. PCT/JP2020/010079, filed on Mar. 9, 2020.

(30) Foreign Application Priority Data

Mar. 8, 2019 (JP) ................................. 2019-042501
Mar. 9, 2020 (JP) ................................. 2020-039545

(51) Int. Cl.
G16H 30/40 (2018.01)
G06F 17/18 (2006.01)
G06T 7/00 (2017.01)

(52) U.S. Cl.
CPC ............ *G16H 30/40* (2018.01); *G06F 17/18* (2013.01); *G06T 7/0012* (2013.01); *G06T 2207/20076* (2013.01); *G06T 2207/20081* (2013.01); *G06T 2207/30096* (2013.01)

(58) Field of Classification Search
None
See application file for complete search history.

(56) References Cited

U.S. PATENT DOCUMENTS

| | | | |
|---|---|---|---|
| 2017/0098301 A1* | 4/2017 | Ikemoto | G06T 7/0012 |
| 2018/0232883 A1 | 8/2018 | Sethi et al. | |
| 2019/0058330 A1 | 2/2019 | Kobayashi et al. | |
| 2020/0218943 A1* | 7/2020 | Osake | G06F 18/217 |

FOREIGN PATENT DOCUMENTS

| | | |
|---|---|---|
| JP | 2014-2473 A | 1/2014 |
| JP | 2015-116319 A | 6/2015 |
| WO | WO2017/170018 A1 | 10/2017 |

OTHER PUBLICATIONS

International Search Report dated Jun. 23, 2020 in PCT/JP2020/010079 filed Mar. 9, 2020, 2 pages.
Matthew A. Kupinski, et al., "Ideal Observer Approximation Using Bayesian Classification Neural Networks", IEEE Transactions On Medical Imaging, vol. 20, No. 9, Sep. 2001, 14 pages.

* cited by examiner

*Primary Examiner* — Leon Flores
(74) *Attorney, Agent, or Firm* — Oblon, McClelland, Maier & Neustadt, L.L.P.

(57) ABSTRACT

The medical data processing apparatus according to any of embodiments includes processing circuitry. The processing circuitry is configured to calculate a probability that target image data has a lesion and a confidence interval indicating a reliability of the probability, and to output data on the lesion based on the probability and the confidence interval of the probability.

16 Claims, 57 Drawing Sheets

| PATTERN NUMBER | PATTERN NAME | PATTERN CLASSIFICATION CRITERIA (BELONGING TO PATTERN WHEN CRITERIA IS MET) WEIGHTING FUNCTION OF PATTERN | DISPLAY CRITERIA (DISPLAYED WHEN CRITERIA IS MET) | CHILD PATTERN | DESIGNED GOAL |
|---|---|---|---|---|---|
| h=1 | simple SMOOTH-MARGINATING | $xs1 \leq T1h$ $u(T1h-xs1)$ ※T1h INDICATES T11 | True (ALWAYS DISPLAYED) | 3, 4 | FOR NEGATIVE PREDICTION, PPV<0.05, MAXIMIZING SPECIFICITY |
| h=2 | complex NON-SMOOTH-MARGINATING | $xs1 > T1h$ $1-u(t1h-xs1)$ | True (ALWAYS DISPLAYED) | 5, 6 | FOR NEGATIVE PREDICTION, PPV<0.05, MAXIMIZING SPECIFICITY |
| h=3 | simple-downslope SMOOTH-MARGINATING/DESCENDING | $xs1 \leq T1h$ and $xs2 \leq T2h$ | LARGER CLASSIFICATION REASONABILITY SCALE THAN ALL ABOVE PATTERNS (PARENT PATTERNS) | 7, 8 | FOR NEGATIVE PREDICTION, PPV<0.05, MAXIMIZING SPECIFICITY |
| h=4 | simple-not downslope SMOOTH-MARGINATING/NON-DESCENDING | $xs1 \leq T1h$ and $xs2 > T2h$ | LARGER CLASSIFICATION REASONABILITY SCALE THAN ALL ABOVE PATTERNS (PARENT PATTERNS) | 9, 10 | FOR POSITIVE PREDICTION, PPV>0.9, MAXIMIZING SENSITIVITY |
| h=5 | complex-downslope NON-SMOOTH-MARGINATING/DESCENDING | $xs1 > T1h$ and $xs2 \leq T2h$ | LARGER CLASSIFICATION REASONABILITY SCALE THAN ALL ABOVE PATTERNS (PARENT PATTERNS) | 11, 12 | FOR NEGATIVE PREDICTION, PPV<0.05, MAXIMIZING SPECIFICITY |
| h=6 | complex-not downslope NON-SMOOTH-MARGINATING/ NON-DESCENDING | $xs1 > T1h$ and $xs2 > T2h$ | LARGER CLASSIFICATION REASONABILITY SCALE THAN ALL ABOVE PATTERNS (PARENT PATTERNS) | 13, 14 | FOR NEGATIVE PREDICTION, PPV<0.05, MAXIMIZING SPECIFICITY |
| ... | ... | ... | ... | | ... |
| h=9 | simple-not downslope-uniform SMOOTH-MARGINATING/DESCENDING/ UNIFORM | $xs1 \leq T1h$ and $xs2 \leq T2h$ and $xs2 \leq T3h$ | LARGER CLASSIFICATION REASONABILITY SCALE THAN ALL ABOVE PATTERNS (PARENT PATTERNS) | | FOR NEGATIVE PREDICTION, PPV<0.05, MAXIMIZING SPECIFICITY |
| h=10 | simple-not downslope-not uniform SMOOTH-MARGINATING/DESCENDING/ NON-UNIFORM | $xs1 \leq T1h$ and $xs2 \leq T2h$ and $xs2 > T3h$ | LARGER CLASSIFICATION REASONABILITY SCALE THAN ALL ABOVE PATTERNS (PARENT PATTERNS) | | FOR POSITIVE PREDICTION, PPV>0.9, MAXIMIZING SENSITIVITY |
| ... | ... | | | | ... |

FIG. 7

```
if ( DESIGNED GOAL BEING "FOR NEGATIVE PREDICTION" )    { // POSITIVE PREDICTION
    PROTRUSION AMOUNT FROM CONFIDENCE INTERVAL AT TIME OF POSITIVE PREDICTION =
    LOWER LIMIT BY PPV-DESIGN AT TIME OF POSITIVE PREDICTION - LOWER LIMIT OF CONFIDENCE INTERVAL FOR PREDICTED POSITIVE RATE
    CLASSIFICATION REASONABILITY SCALE = - ( PROTRUSION AMOUNT FROM CONFIDENCE INTERVAL AT TIME OF POSITIVE DECISION )
    if ( PROTRUSION AMOUNT FROM CONFIDENCE INTERVAL AT TIME OF POSITIVE PREDICTION <= 0 )
        CLASSIFICATION REASONABILITY SCALE = LOWER LIMIT OF CONFIDENCE INTERVAL FOR POSITIVE RATE IN MALIGNANT GROUP // HIGHER SENSITIVE ONE IS APPROPRIATE
}
else {  // NEGATIVE PREDICTION
    PROTRUSION AMOUNT FROM CONFIDENCE INTERVAL AT TIME OF NEGATIVE PREDICTION =
    UPPER LIMIT OF CONFIDENCE INTERVAL FOR PREDICTED POSITIVE RATE - UPPER LIMIT BY PPV-DESIGN AT TIME OF NEGATIVE PREDICTION
    CLASSIFICATION REASONABILITY SCALE = - ( PROTRUSION AMOUNT FROM CONFIDENCE INTERVAL AT TIME OF NEGATIVE PREDICTION )
    if ( PROTRUSION AMOUNT FROM CONFIDENCE INTERVAL AT TIME OF NEGATIVE PREDICTION <= 0 )
        CLASSIFICATION REASONABILITY SCALE = 1 - UPPER LIMIT OF CONFIDENCE INTERVAL FOR POSITIVE RATE IN BENIGN GROUP // HIGHER SPECIFIC ONE IS APPROPRIATE
}
```

FIG. 8

| PATTERN NUMBER | PATTERN NAME | WEIGHTING FUNCTION OF PATTERN | DISPLAY CRITERIA (DISPLAYED WHEN CRITERIA IS MET) | CHILD PATTERN | DESIGNED GOAL |
|---|---|---|---|---|---|
| h=1 | complexity###<br>COMPLEXITY### | Normdist xs1<br>※σ1h INDICATES σ11 | True (ALWAYS DISPLAYED) | 3 | FOR NEGATIVE PREDICTION, PPV<0.05, MAXIMIZING SPECIFICITY |
| h=2 | complexity###<br>COMPLEXITY### | Normdist xs1 | True (ALWAYS DISPLAYED) | 4 | FOR POSITIVE PREDICTION, PPV>0.9, MAXIMIZING SENSITIVITY |
| h=3 | complexity###-downslope###-<br>COMPLEXITY###-DESCENDING### | Normdist xs1, xs2 | LARGER CLASSIFICATION REASONABILITY SCALE THAN ALL ABOVE PATTERNS (PARENT PATTERNS) | 5 | FOR NEGATIVE PREDICTION, PPV<0.05, MAXIMIZING SPECIFICITY |
| h=4 | complexity###-downslope###-<br>COMPLEXITY###-DESCENDING### | Normdist xs1, xs2 | LARGER CLASSIFICATION REASONABILITY SCALE THAN ALL ABOVE PATTERNS (PARENT PATTERNS) | 6 | FOR POSITIVE PREDICTION, PPV>0.9, MAXIMIZING SENSITIVITY |
| h=5 | complexity###-downslope###-<br>nonuniformity###<br>COMPLEXITY###-DESCENDING###-NON-UNIFORM### | Normdist xs1, xs2, xs3 | LARGER CLASSIFICATION REASONABILITY SCALE THAN ALL ABOVE PATTERNS (PARENT PATTERNS) | | FOR NEGATIVE PREDICTION, PPV<0.05, MAXIMIZING SPECIFICITY |
| h=6 | complexity###-downslope###-<br>nonuniformity###<br>COMPLEXITY###-DESCENDING###-NON-UNIFORM### | Normdist xs1, xs2, xs3 | LARGER CLASSIFICATION REASONABILITY SCALE THAN ALL ABOVE PATTERNS (PARENT PATTERNS) | | FOR POSITIVE PREDICTION, PPV>0.9, MAXIMIZING SENSITIVITY |
| ... | ... | ... | ... | ... | ... |

FIG. 11

|  | PREDICTION | | | |
|---|---|---|---|---|
| CLASS | GLIOMA | PCNSL | BRAIN METASTASIS | OTHER |
| N=1308 | N=254 | 279 | 372 | 403 |
| INSTITUTIONAL PREVALENCE | 25.0% | 20.0% | 30.0% | 25.0% ← CHANGEABLE |
| CATEGORY | HIGH POSSIBILITY | UNPREDICTABLE | LOW PROBABILITY | UNPREDICTABLE |
| AVERAGE PROBABILITY (THE NUMBER OF CASES) | 91.1% (136/151) | 2.6% (4/151) | 2.1% (3/151) | 4.2% (4/151) |
| CONFIDENCE INTERVAL — UPPER LIMIT | 97.7% | 28.1% | 17.9% | 37.4% |
| CONFIDENCE INTERVAL — LOWER LIMIT | 8.68% | 1.4% | 0.3% | 0.2% |
| DETERMINISTIC | 95% | | | |
| HIGH POSSIBILITY | 80% | | | |
| INDEFINITE | | | | |
| LOW PROBABILITY | 20% | | | |
| NEGATIVE | 5% | | | |
| | 0% | | | |

FIG. 21B

| CATEGORY | GROUP | |
|---|---|---|
| | SLIGHT POSSIBILITY OF LESION | LESION-PRESENCE |
| DEFINITE LESION | UPPER LIMIT 0%– 1% | LOWER LIMIT 99%–100% |
| LESION-PRESENCE | UPPER LIMIT 1%– 5% | LOWER LIMIT 95%– 99% |
| HIGH PROBABILITY OF LESION | UPPER LIMIT 5%– 20% | LOWER LIMIT 80%– 95% |
| MEDIUM PROBABILITY OF LESION | UPPER LIMIT 20%–100%<br>LOWER LIMIT 0%– 80%<br>DIFFERENCE <20 | UPPER LIMIT 20%–100%<br>LOWER LIMIT 0%– 80%<br>DIFFERENCE <20 |
| UNPREDICTABLE | UPPER LIMIT 20%–100%<br>LOWER LIMIT 0%– 80%<br>DIFFERENCE >20 | UPPER LIMIT 20%–100%<br>LOWER LIMIT 0%– 80%<br>DIFFERENCE >20 |
| LOW PROBABILITY OF LESION | LOWER LIMIT 80%– 95% | UPPER LIMIT 5%– 20% |
| SLIGHT POSSIBILITY OF LESION | LOWER LIMIT 95%– 99% | UPPER LIMIT 1%– 5% |
| NEGATIVE | LOWER LIMIT 99%–100% | UPPER LIMIT 0%– 1% |

| CATEGORY | GROUP TO BE PREDICTED / DISPLAY EXAMPLE OF GROUP | GROUP | | | | |
|---|---|---|---|---|---|---|
| | | A AND B / OTHER THAN C AND D | C AND D / OTHER THAN A AND B | C / OTHER THAN A,B,D | A,B,D / OTHER THAN C | D / OTHER THAN A,B,C |
| DEFINITIVE | | UPPER LIMIT 0%–1% | LOWER LIMIT 99%–100% | UPPER LIMIT 0%–1% | LOWER LIMIT 99%–100% | LOWER LIMIT 99%–100% |
| ALMOST DEFINITIVE | | UPPER LIMIT 1%–5% | LOWER LIMIT 95%–99% | UPPER LIMIT 1%–5% | LOWER LIMIT 95%–99% | LOWER LIMIT 95%–99% |
| HIGH PROBABILITY | | UPPER LIMIT 5%–20% | LOWER LIMIT 80%–95% | UPPER LIMIT 5%–20% | LOWER LIMIT 80%–95% | LOWER LIMIT 80%–95% |
| MEDIUM PROBABILITY | | UPPER LIMIT 20%–100% | UPPER LIMIT 20%–100% | UPPER LIMIT 20%–100% | UPPER LIMIT 20%–100% | UPPER LIMIT 20%–100% |
| | | LOWER LIMIT 0%–80% | LOWER LIMIT 0%–80% | LOWER LIMIT 0%–80% | LOWER LIMIT 0%–80% | LOWER LIMIT 0%–80% |
| | | DIFFERENCE <20 | DIFFERENCE >20 | DIFFERENCE <20 | DIFFERENCE >20 | DIFFERENCE >20 |
| UNPREDICTABLE | | UPPER LIMIT 20%–100% | UPPER LIMIT 20%–100% | UPPER LIMIT 20%–100% | UPPER LIMIT 20%–100% | UPPER LIMIT 20%–100% |
| | | LOWER LIMIT 0%–80% | LOWER LIMIT 0%–80% | LOWER LIMIT 0%–80% | LOWER LIMIT 0%–80% | LOWER LIMIT 0%–80% |
| | | DIFFERENCE >20 | DIFFERENCE <20 | DIFFERENCE >20 | DIFFERENCE <20 | DIFFERENCE <20 |
| LOW PROBABILITY | | LOWER LIMIT 80%–95% | UPPER LIMIT 5%–20% | LOWER LIMIT 80%–95% | UPPER LIMIT 5%–20% | UPPER LIMIT 5%–20% |
| SLIGHT POSSIBILITY | | LOWER LIMIT 95%–99% | UPPER LIMIT 1%–5% | LOWER LIMIT 95%–99% | UPPER LIMIT 1%–5% | UPPER LIMIT 1%–5% |
| NEGATIVE | | LOWER LIMIT 99%–100% | UPPER LIMIT 0%–1% | LOWER LIMIT 99%–100% | UPPER LIMIT 0%–1% | UPPER LIMIT 0%–1% |

| CATEGORY | GROUP TO BE PREDICTED | GROUP | | | | | |
|---|---|---|---|---|---|---|---|
| | | F0 | F0 | F1 | F2 | F3 | F4 |
| | DISPLAY EXAMPLE OF GROUP | F0 | OTHER THAN F0 | F1 | F2 | F3 | F4 |
| CATEGORY | | | | | | | |

FIG. 38

| CATEGORY | GROUP | | | | | |
|---|---|---|---|---|---|---|
| | DRUG A | | DRUG B | | DRUG C | |
| EFFECTIVE | LOWER LIMIT | 95%–100% | LOWER LIMIT | 95%–100% | LOWER LIMIT | 95%–100% |
| OFTEN EFFECTIVE | LOWER LIMIT | 80%–95% | LOWER LIMIT | 80%–95% | LOWER LIMIT | 80%–95% |
| A LITTLE EFFECTIVE | UPPER LIMIT | 20%–100% | UPPER LIMIT | 20%–100% | UPPER LIMIT | 20%–100% |
| | LOWER LIMIT | 0%–80% | LOWER LIMIT | 0%–80% | LOWER LIMIT | 0%–80% |
| | DIFFERENCE | <20 | DIFFERENCE | <20 | DIFFERENCE | <20 |
| UNKNOWN EFFECT | UPPER LIMIT | 20%–100% | UPPER LIMIT | 20%–100% | UPPER LIMIT | 20%–100% |
| | LOWER LIMIT | 0%–80% | LOWER LIMIT | 0%–80% | LOWER LIMIT | 0%–80% |
| | DIFFERENCE | >20 | DIFFERENCE | >20 | DIFFERENCE | >20 |
| OFTEN INEFFECTIVE | UPPER LIMIT | 5%–20% | UPPER LIMIT | 5%–20% | UPPER LIMIT | 5%–20% |
| NO EFFECT | UPPER LIMIT | 0%–5% | UPPER LIMIT | 0%–5% | UPPER LIMIT | 0%–5% |

FIG. 39A

| CATEGORY | GROUP | | | | | | |
|---|---|---|---|---|---|---|---|
| | DRUG A | | DRUG B | | DRUG C | | |
| HIGH FREQUENCY OF SIDE EFFECT | LOWER LIMIT | 95%–100% | LOWER LIMIT | 95%–100% | LOWER LIMIT | 95%–100% | |
| SLIGHTLY HIGH FREQUENCY OF SIDE EFFECT | LOWER LIMIT | 80%–95% | LOWER LIMIT | 80%–95% | LOWER LIMIT | 80%–95% | |
| MIDDLE FREQUENCY OF SIDE EFFECT | UPPER LIMIT | 20%–100% | UPPER LIMIT | 20%–100% | UPPER LIMIT | 20%–100% | |
| | LOWER LIMIT | 0%–80% | LOWER LIMIT | 0%–80% | LOWER LIMIT | 0%–80% | |
| | DIFFERENCE | <20 | DIFFERENCE | <20 | DIFFERENCE | <20 | |
| UNKNOWN FREQUENCY OF SIDE EFFECT | UPPER LIMIT | 20%–100% | UPPER LIMIT | 20%–100% | UPPER LIMIT | 20%–100% | |
| | LOWER LIMIT | 0%–80% | LOWER LIMIT | 0%–80% | LOWER LIMIT | 0%–80% | |
| | DIFFERENCE | >20 | DIFFERENCE | >20 | DIFFERENCE | >20 | |
| SLIGHTLY LOW FREQUENCY OF SIDE EFFECT | UPPER LIMIT | 5%–20% | UPPER LIMIT | 5%–20% | UPPER LIMIT | 5%–20% | |
| LOW FREQUENCY OF SIDE EFFECT | UPPER LIMIT | 0%–5% | UPPER LIMIT | 0%–5% | UPPER LIMIT | 0%–5% | |

FIG. 39B

| CATEGORY | GROUP | | | | | | | | | | |
|---|---|---|---|---|---|---|---|---|---|---|---|
| | MYOCARDIAL INFARCTION | | FATAL ARRHYTHMIA | | CORONARY ARTERY RECONSTRUCTION | | BYPASS SURGERY | | SUDDEN CARDIAC DEATH | | |
| MORE THAN 80% | LOWER LIMIT | 80%-100% | LOWER LIMIT | 80%-100% | LOWER LIMIT | 80%-100% | LOWER LIMIT | 80%-100% | LOWER LIMIT | 80%-95% | |
| POSSIBILITY OF 20% OR MORE | UPPER LIMIT | 20%-100% | UPPER LIMIT | 20%-100% | UPPER LIMIT | 20%-100% | UPPER LIMIT | 20%-100% | UPPER LIMIT | 20%-100% | |
| | LOWER LIMIT | 0%-80% | LOWER LIMIT | 0%-80% | LOWER LIMIT | 0%-80% | LOWER LIMIT | 0%-80% | LOWER LIMIT | 0%-80% | |
| | DIFFERENCE | <20 | DIFFERENCE | <20 | DIFFERENCE | <20 | DIFFERENCE | <20 | DIFFERENCE | <20 | |
| UNKNOWN | UPPER LIMIT | 20%-100% | UPPER LIMIT | 20%-100% | UPPER LIMIT | 20%-100% | UPPER LIMIT | 20%-100% | UPPER LIMIT | 20%-100% | |
| | LOWER LIMIT | 0%-80% | LOWER LIMIT | 0%-80% | LOWER LIMIT | 0%-80% | LOWER LIMIT | 0%-80% | LOWER LIMIT | 0%-80% | |
| | DIFFERENCE | >20 | DIFFERENCE | >20 | DIFFERENCE | >20 | DIFFERENCE | >20 | DIFFERENCE | >20 | |
| LESS THAN 20% | UPPER LIMIT | 5%-20% | UPPER LIMIT | 5%-20% | UPPER LIMIT | 5%-20% | UPPER LIMIT | 5%-20% | UPPER LIMIT | 5%-20% | |
| LESS THAN 5% | UPPER LIMIT | 1%-5% | UPPER LIMIT | 1%-5% | UPPER LIMIT | 1%-5% | UPPER LIMIT | 1%-5% | UPPER LIMIT | 1%-5% | |
| LESS THAN 1% | UPPER LIMIT | 0%-1% | UPPER LIMIT | 0%-1% | UPPER LIMIT | 0%-1% | UPPER LIMIT | 0%-1% | UPPER LIMIT | 0%-1% | |

FIG. 40A

| CATEGORY | GROUP | | | | |
|---|---|---|---|---|---|
| | GOOD PHYSICAL FUNCTION | PAINLESS AND GOOD | GOOD HEALTH | GOOD DAILY ROLE FUNCTION | MENTAL HEALTH |
| MORE THAN 80% | LOWER LIMIT 80%–100% | LOWER LIMIT 80%–100% | LOWER LIMIT 80%–100% | LOWER LIMIT 80%–100% | LOWER LIMIT 80%–95% |
| POSSIBILITY OF 20% OR MORE | UPPER LIMIT 20%–100%<br>LOWER LIMIT 0%–80%<br>DIFFERENCE <20 | UPPER LIMIT 20%–100%<br>LOWER LIMIT 0%–80%<br>DIFFERENCE <20 | UPPER LIMIT 20%–100%<br>LOWER LIMIT 0%–80%<br>DIFFERENCE <20 | UPPER LIMIT 20%–100%<br>LOWER LIMIT 0%–80%<br>DIFFERENCE <20 | UPPER LIMIT 20%–100%<br>LOWER LIMIT 0%–80%<br>DIFFERENCE <20 |
| UNKNOWN | UPPER LIMIT 20%–100%<br>LOWER LIMIT 0%–80%<br>DIFFERENCE >20 | UPPER LIMIT 20%–100%<br>LOWER LIMIT 0%–80%<br>DIFFERENCE >20 | UPPER LIMIT 20%–100%<br>LOWER LIMIT 0%–80%<br>DIFFERENCE >20 | UPPER LIMIT 20%–100%<br>LOWER LIMIT 0%–80%<br>DIFFERENCE >20 | UPPER LIMIT 20%–100%<br>LOWER LIMIT 0%–80%<br>DIFFERENCE >20 |
| LESS THAN 20% | UPPER LIMIT 5%–20% | UPPER LIMIT 5%–20% | UPPER LIMIT 5%–20% | UPPER LIMIT 5%–20% | UPPER LIMIT 5%–20% |
| LESS THAN 5% | UPPER LIMIT 1%–5% | UPPER LIMIT 1%–5% | UPPER LIMIT 1%–5% | UPPER LIMIT 1%–5% | UPPER LIMIT 1%–5% |
| LESS THAN 1% | UPPER LIMIT 0%–1% | UPPER LIMIT 0%–1% | UPPER LIMIT 0%–1% | UPPER LIMIT 0%–1% | UPPER LIMIT 0%–1% |

FIG. 40B

| GROUP | LESION PROBABILITY ||||
|---|---|---|---|---|
| | LESION 1 | LESION 2 | LESION 3 | LESION-ABSENCE |
| N=1308 | N=254 | 279 | 372 | 403 |
| RATE IN FACILITY | 25.0% | 20.0% | 30.0% | 25.0% |
| CATEGORY | HIGH PROBABILITY | UNPREDICTABLE | LOW PROBABILITY | UNPREDICTABLE |
| AVERAGE PROBABILITY (THE NUMBER OF CASES) | 91.1% (136/151) | 2.6% (4/151) | 2.1% (3/151) | 4.2% (4/151) |
| CONFIDENCE INTERVAL — UPPER LIMIT | 97.7% | 28.1% | 17.9% | 37.4% |
| CONFIDENCE INTERVAL — LOWER LIMIT | 8.68% | 1.4% | 0.3% | 0.2% |

| DEFINITIVE | |
|---|---|
| HIGH PROBABILITY | 95% – 80% |
| UNPREDICTABLE | 20% – 5% |
| LOW PROBABILITY | |
| NEGATIVE | 0% |

FIG. 41B

MEDICAL DATA PROCESSING APPARATUS, MEDICAL DATA PROCESSING METHOD, AND NON-TRANSITORY COMPUTER MEDIUM STORING COMPUTER PROGRAM

CROSS-REFERENCE TO RELATED APPLICATION

This application is a Continuation Application of No. PCT/JP2020/010079, filed on Mar. 9, 2020, and the PCT application is based upon and claims the benefit of priority from Japanese Patent Application No. 2019-042501, filed on Mar. 8, 2019, and Japanese Patent Application No. 2020-039545, filed on Mar. 9, 2020, the entire contents of each of which are incorporated herein by reference.

FIELD

Any of embodiments disclosed in specification and drawings relates to a medical data processing apparatus, a medical data processing method, and a non-transitory computer medium storing computer program.

BACKGROUND

It becomes possible to acquire a large amount of digitized high-definition medical images. This is due to the development of a medical apparatus such as an X-ray computed tomography (CT) apparatus or a magnetic resonance imaging (MRI) apparatus on the purpose of acquiring radiographic images, and development of virtual slide scanners that capture pathological specimens. In recent years, a picture archiving and communication systems (PACS) for storing the medical images have become widespread, and these images are sequentially stored together with the diagnostic findings of a doctor. As the digitization of the medical images and the accumulation of cases progress, the importance of computer aided diagnosis (CAD) for performing the lesion detection and automatic diagnosis using a computer is increasing.

When performing the lesion detection and automatic diagnosis with the computer, it is common to apply past cases as teacher data to machine learning. One of the problems of the machine learning in a medical data processing is the difficulty of securing cases to be used for learning. Dynamic update of knowledge can be considered as a means for solving such a problem.

The medical data processing apparatus realizes the dynamic update of the knowledge by online learning in order to dynamically update the knowledge. In addition, the end of learning can be determined using the correct answer rate and the number of support vectors of support vector machine (SVM).

In addition, the medical data processing apparatus generates feature generating parameters based on case data for learning, and generates a classification parameter based on the feature vector of each image data generated by using the feature generating parameter. The medical data processing apparatus is known to have a technique of storing feature generating parameter and classification parameter as new diagnostic knowledge in a diagnostic knowledge database.

BRIEF DESCRIPTION OF THE DRAWINGS

FIG. 7 is a diagram showing an example of a pattern setting table in the medical data processing apparatus according to the first embodiment.

FIG. 8 is a diagram showing an example of a pseudo code in the medical information processing apparatus according to the first embodiment.

FIG. 11 is a diagram showing an example of a pattern setting table in the medical data processing apparatus according to the first embodiment.

Figure 14A:
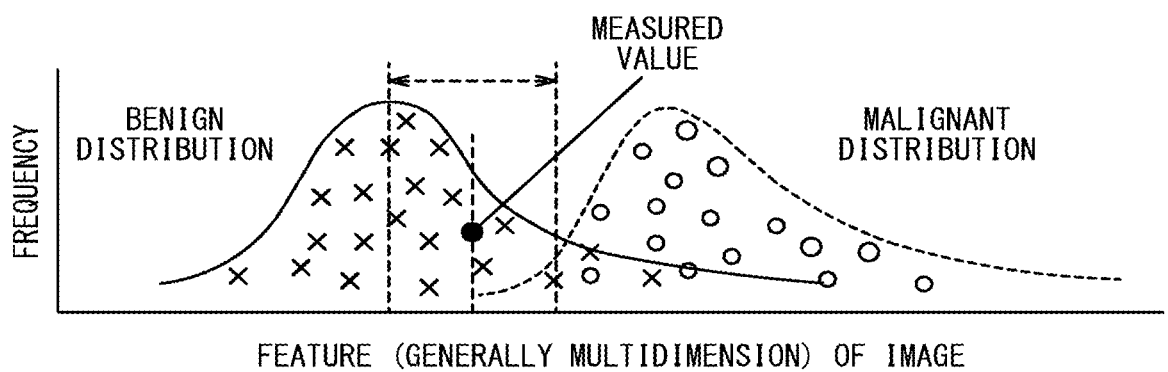
Figure 14B:
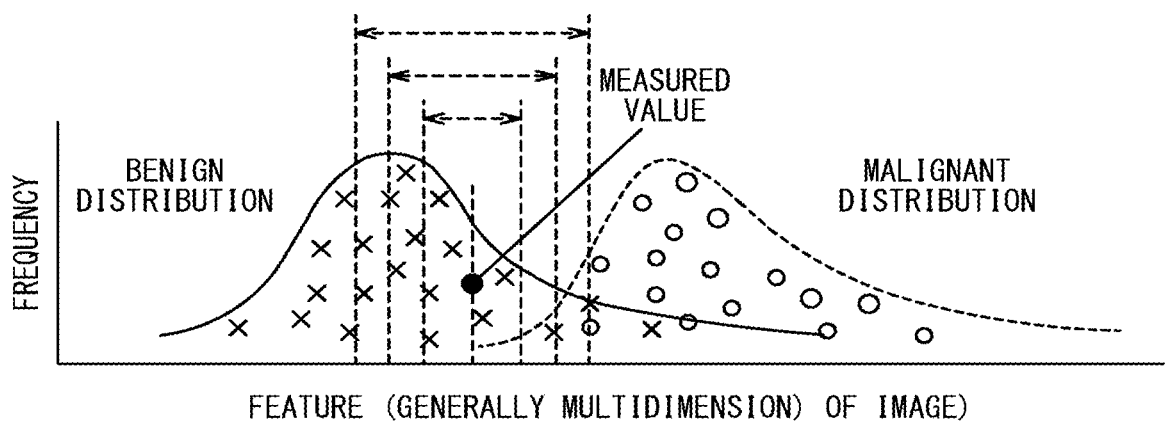

Each of FIGS. 14A and 14B is a diagram for explaining a method of calculating a confidence interval in the medical data processing apparatus according to the second embodiment.

Figure 15:
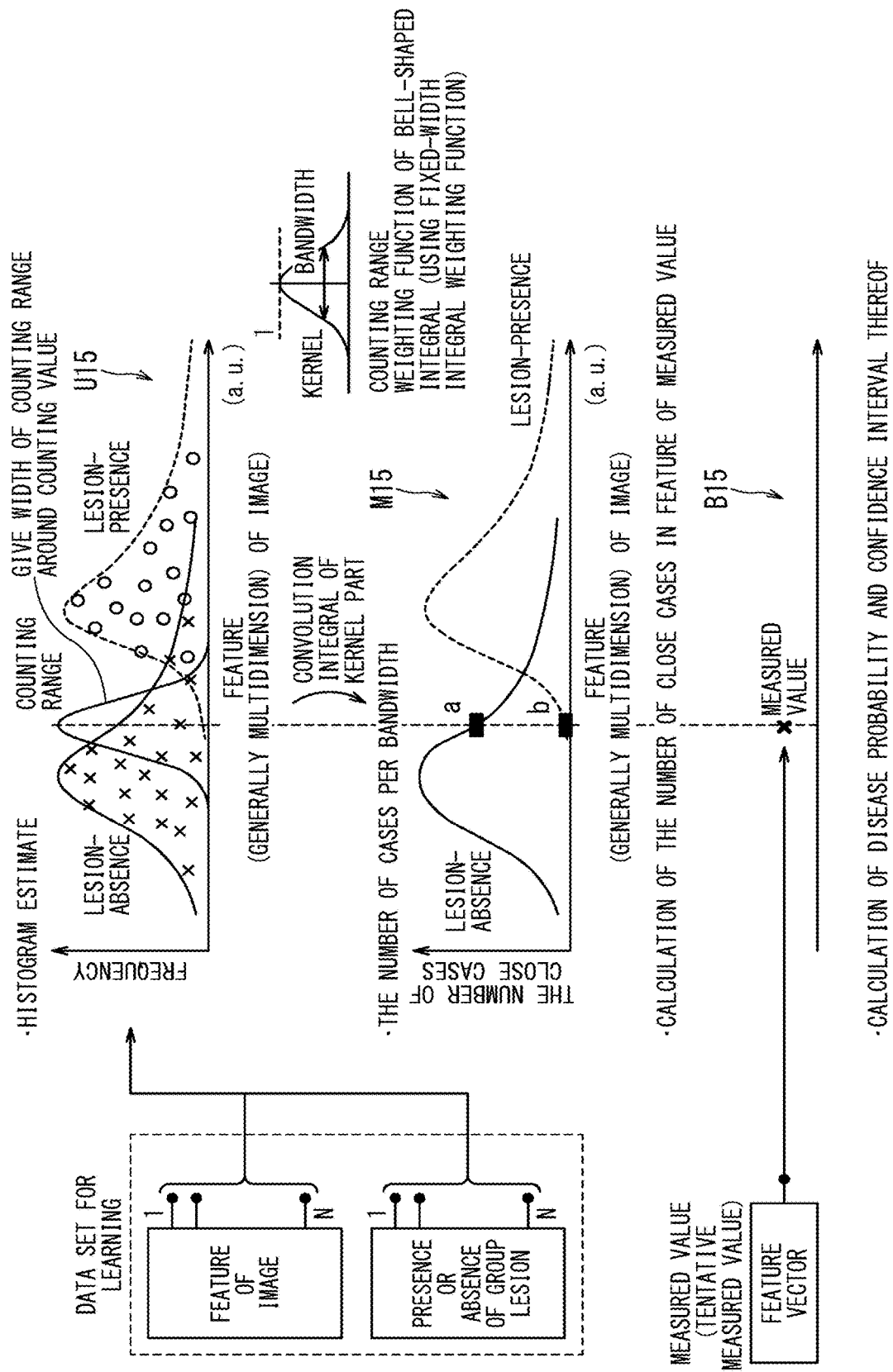

FIG. 15 is a diagram for explaining a method of calculating a confidence interval in the medical data processing apparatus according to the second embodiment.

Figure 16:
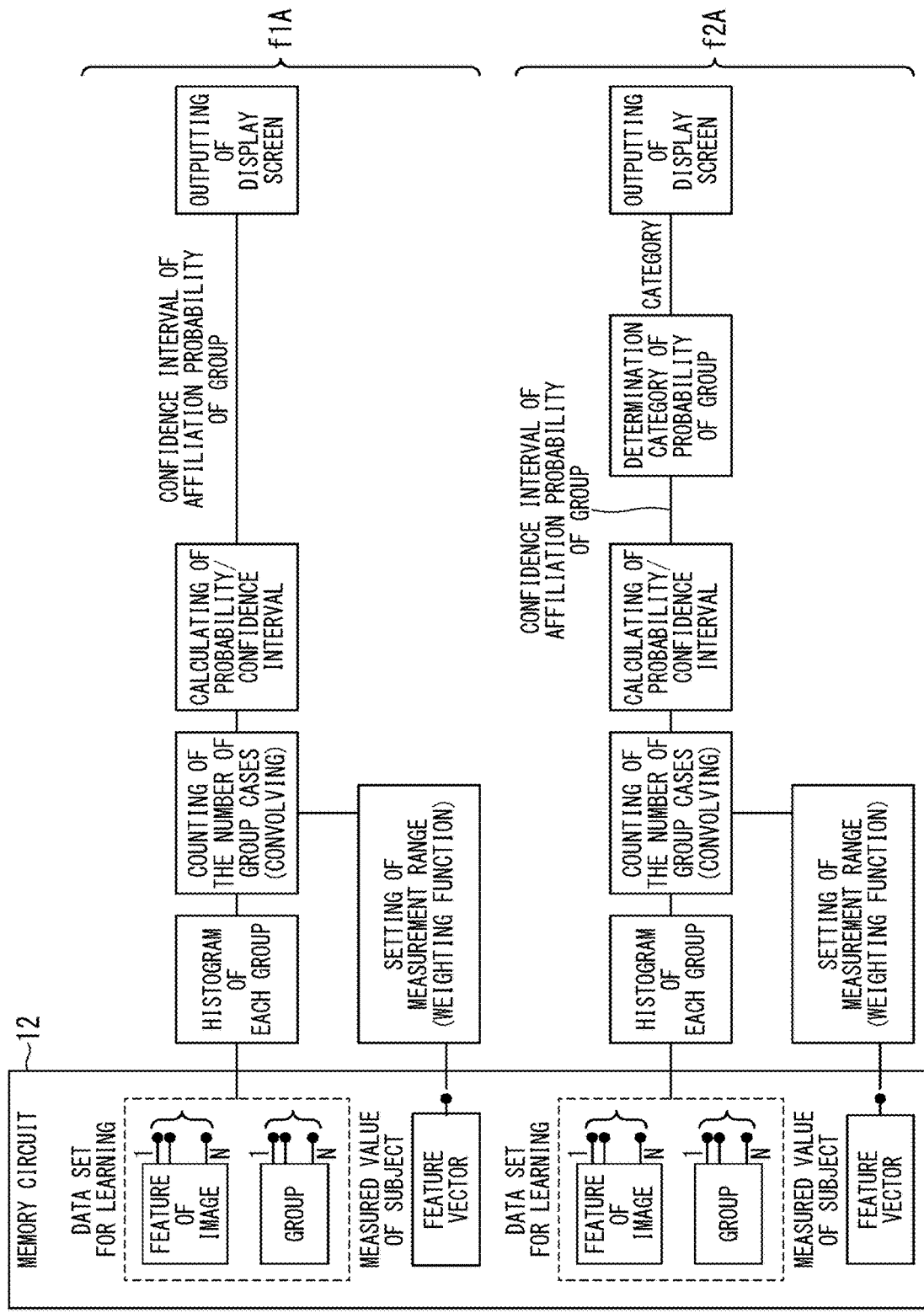

FIG. 16 is a data flow diagram showing the first-A function and the second-A function in the medical data processing apparatus according to the second embodiment.

Figure 17:
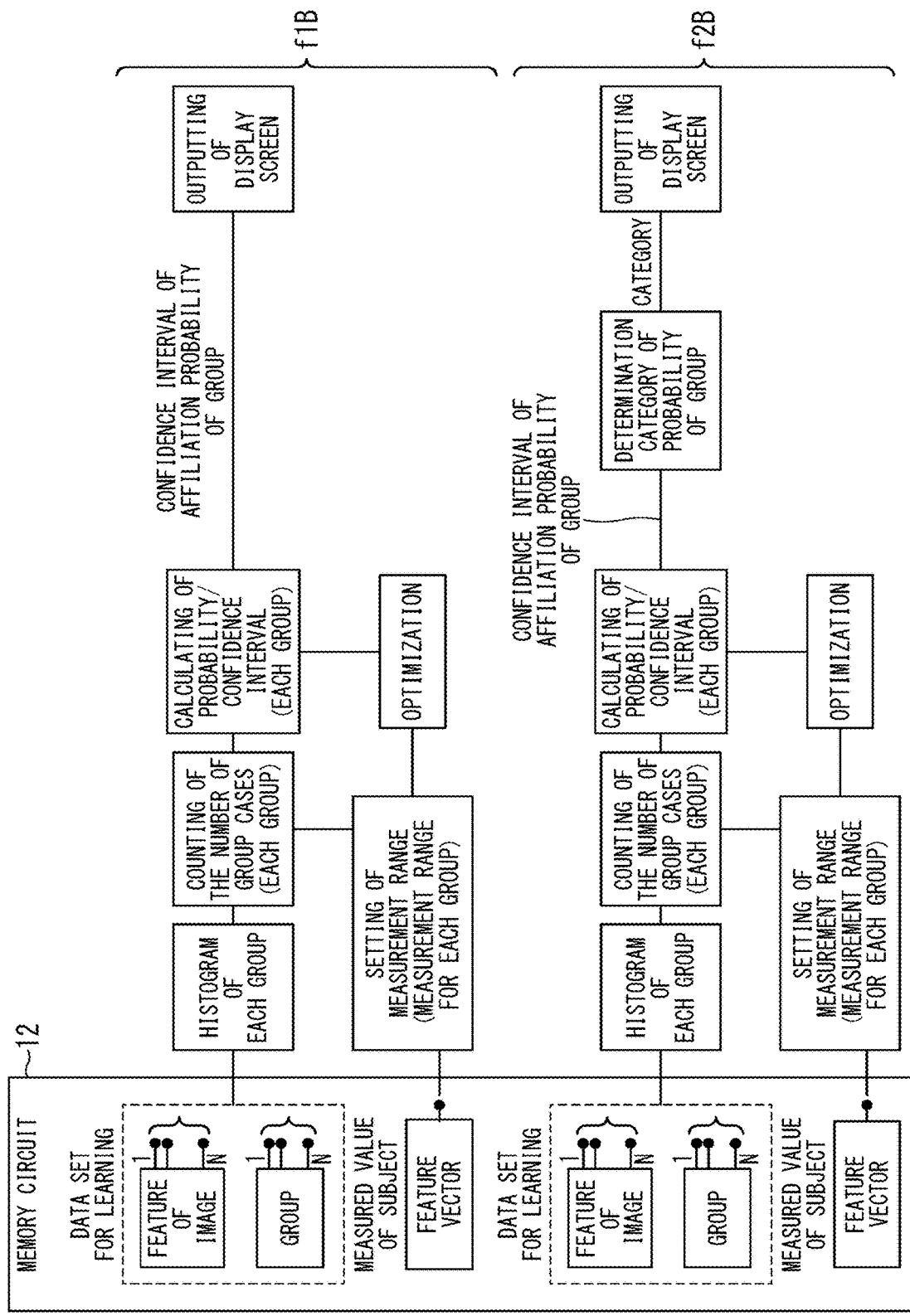

FIG. 17 is a data flow diagram showing the first-B function and the second-B function in the medical data processing apparatus according to the second embodiment.

Figure 18:
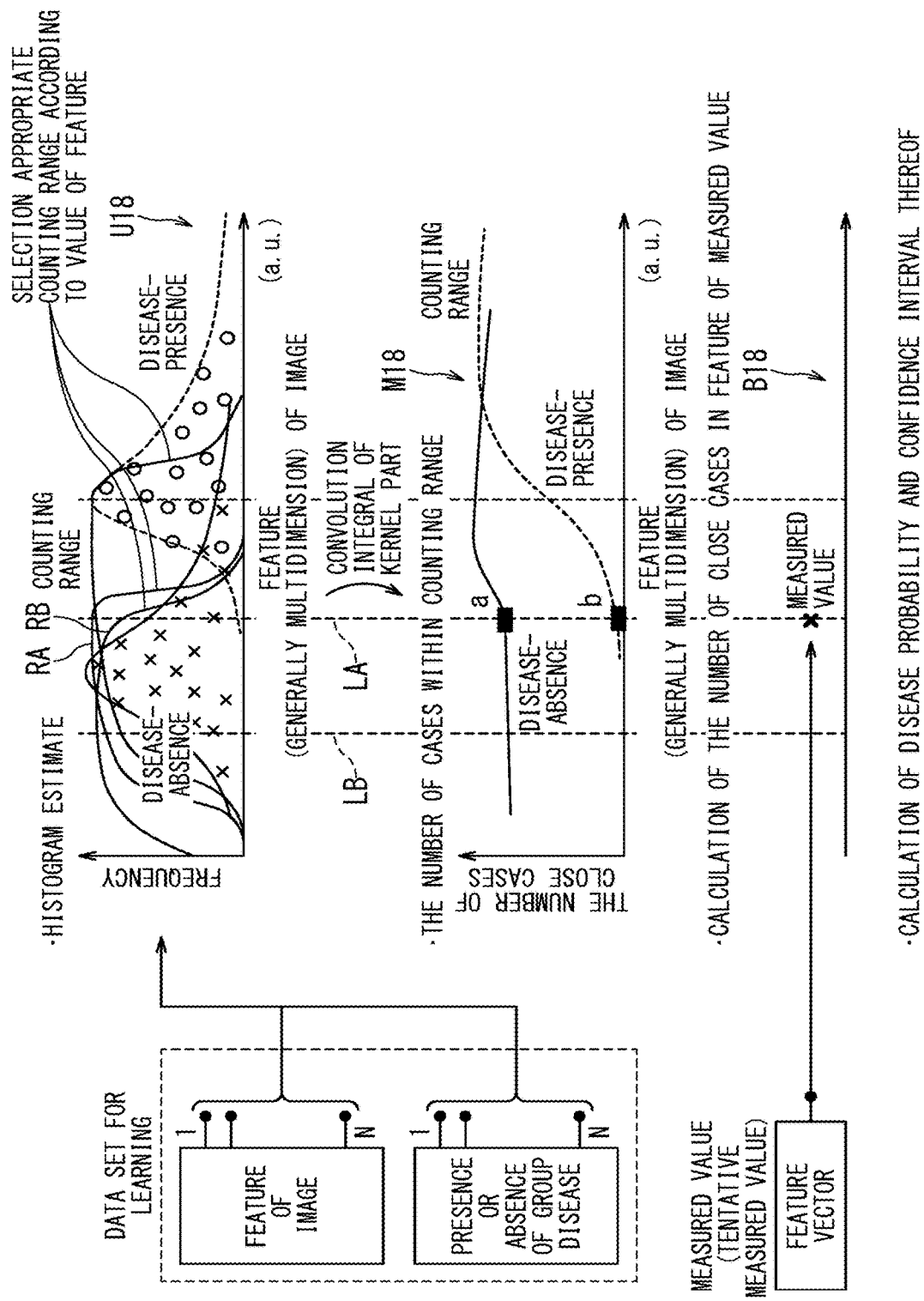

FIG. 18 is a diagram for explaining a method of calculating a confidence interval in the medical data processing apparatus according to the second embodiment.

Figure 19:
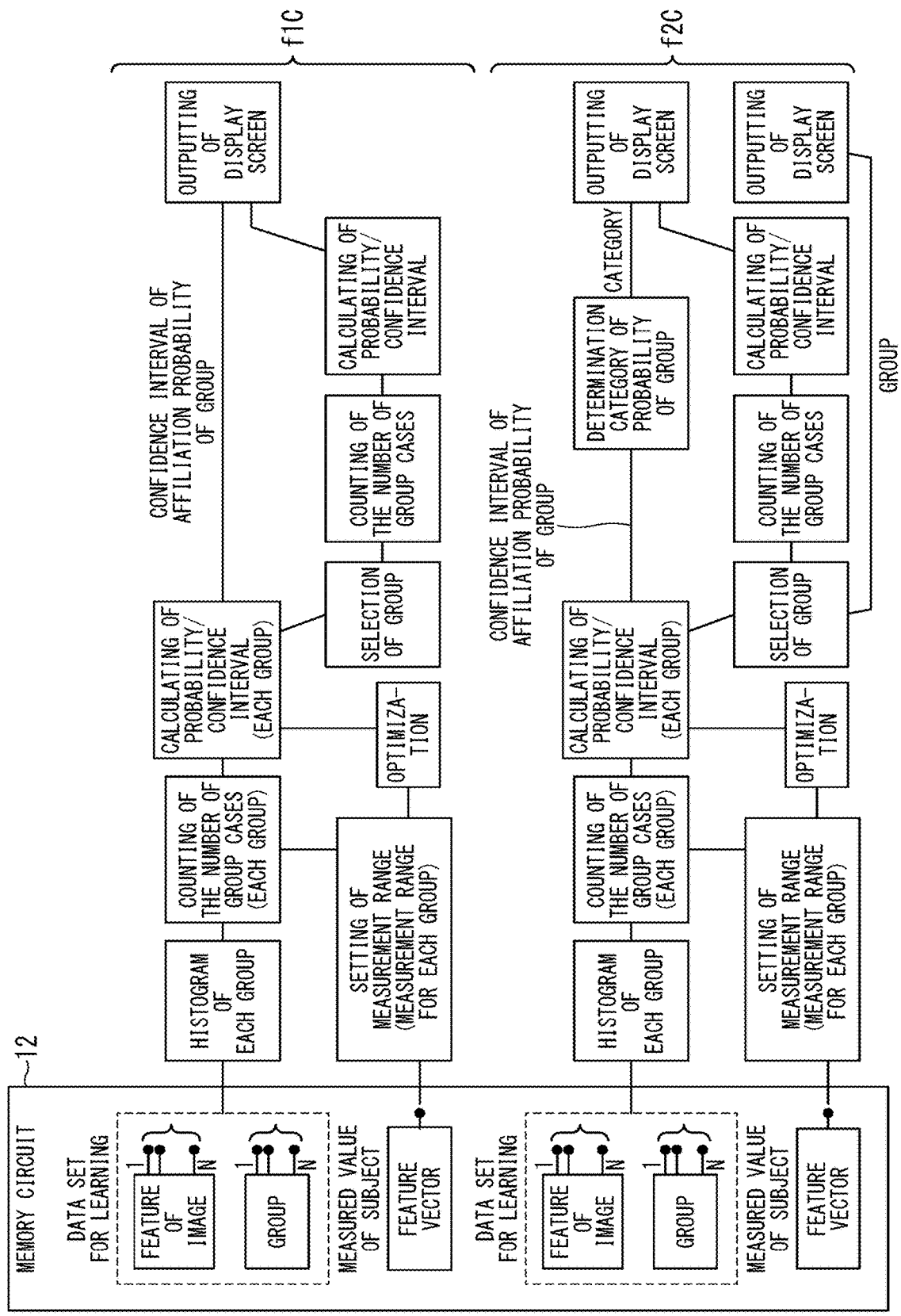

FIG. 19 is a data flow diagram showing the first-C function and the second-C function in the medical data processing apparatus according to the second embodiment.

Each of FIGS. 20A to 20D is a diagram showing an example of a predicted result in the medical data processing apparatus according to the second embodiment.

Figure 21A:
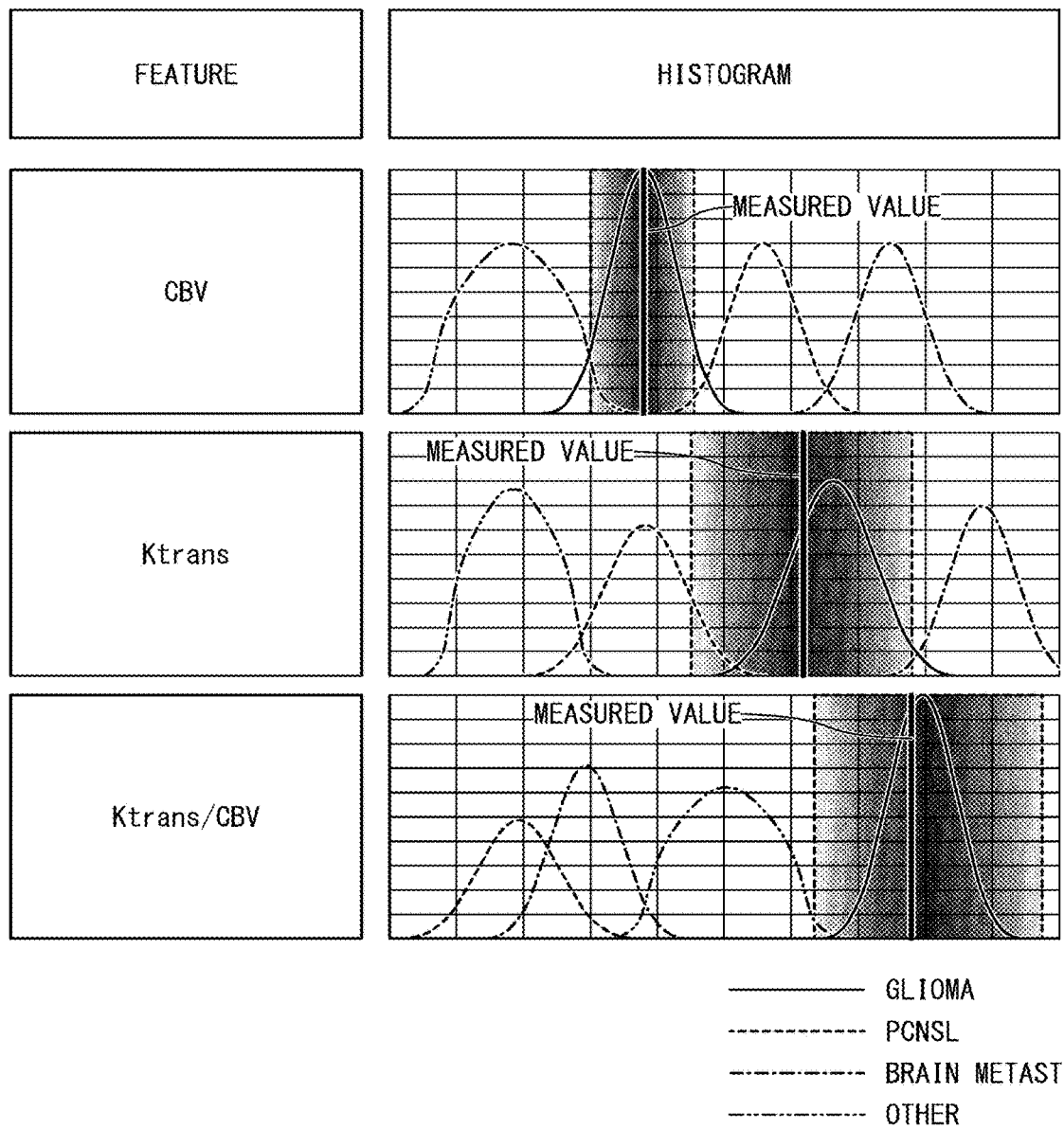
Figure 21C:
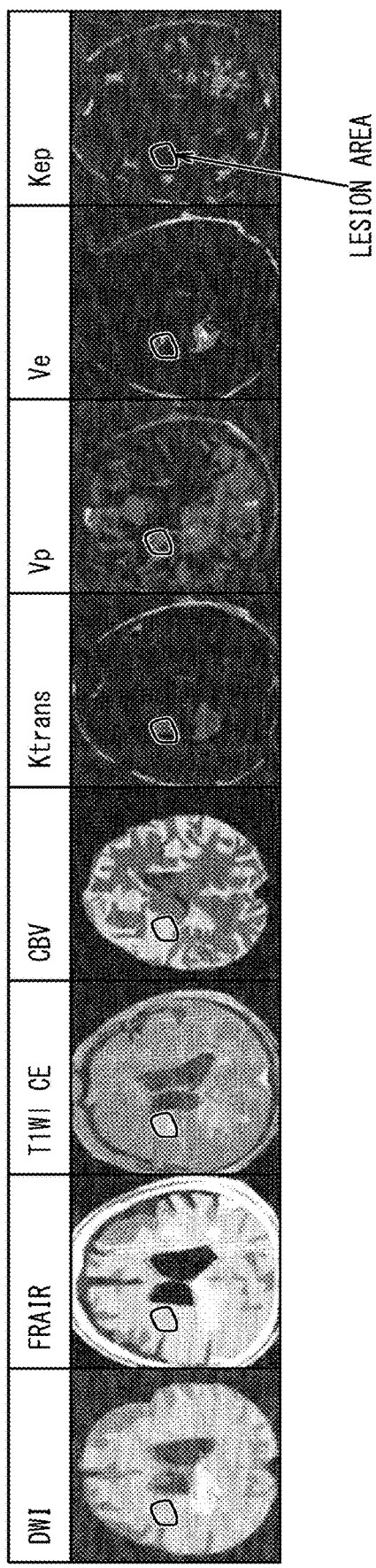

Each of FIGS. 21A to 21C is a diagram showing an example of a predicted result in the medical data processing apparatus according to the second embodiment.

Figure 22:
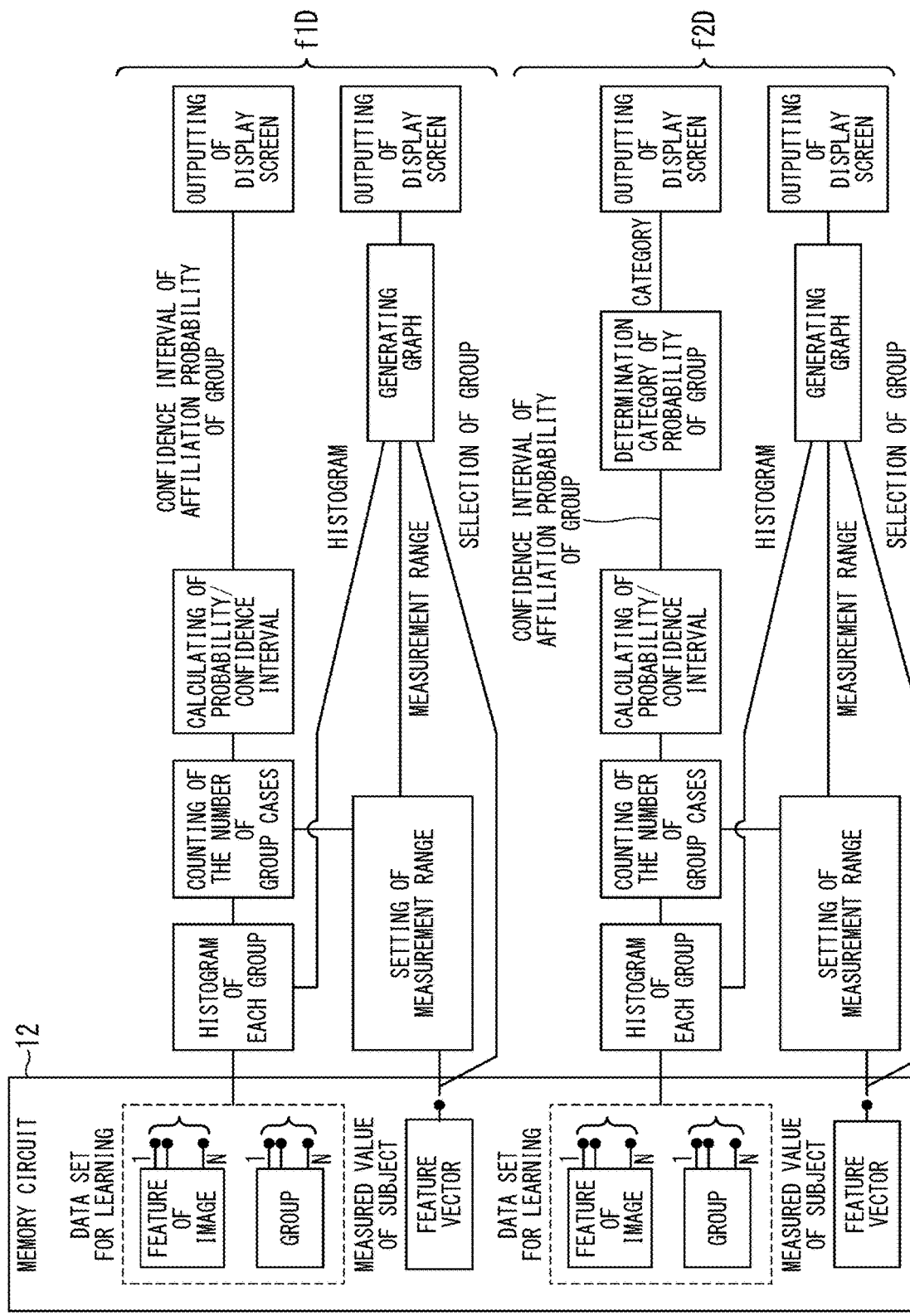

FIG. 22 is a data flow diagram showing the first-D function and the second-D function in the medical data processing apparatus according to the second embodiment.

Figure 23:
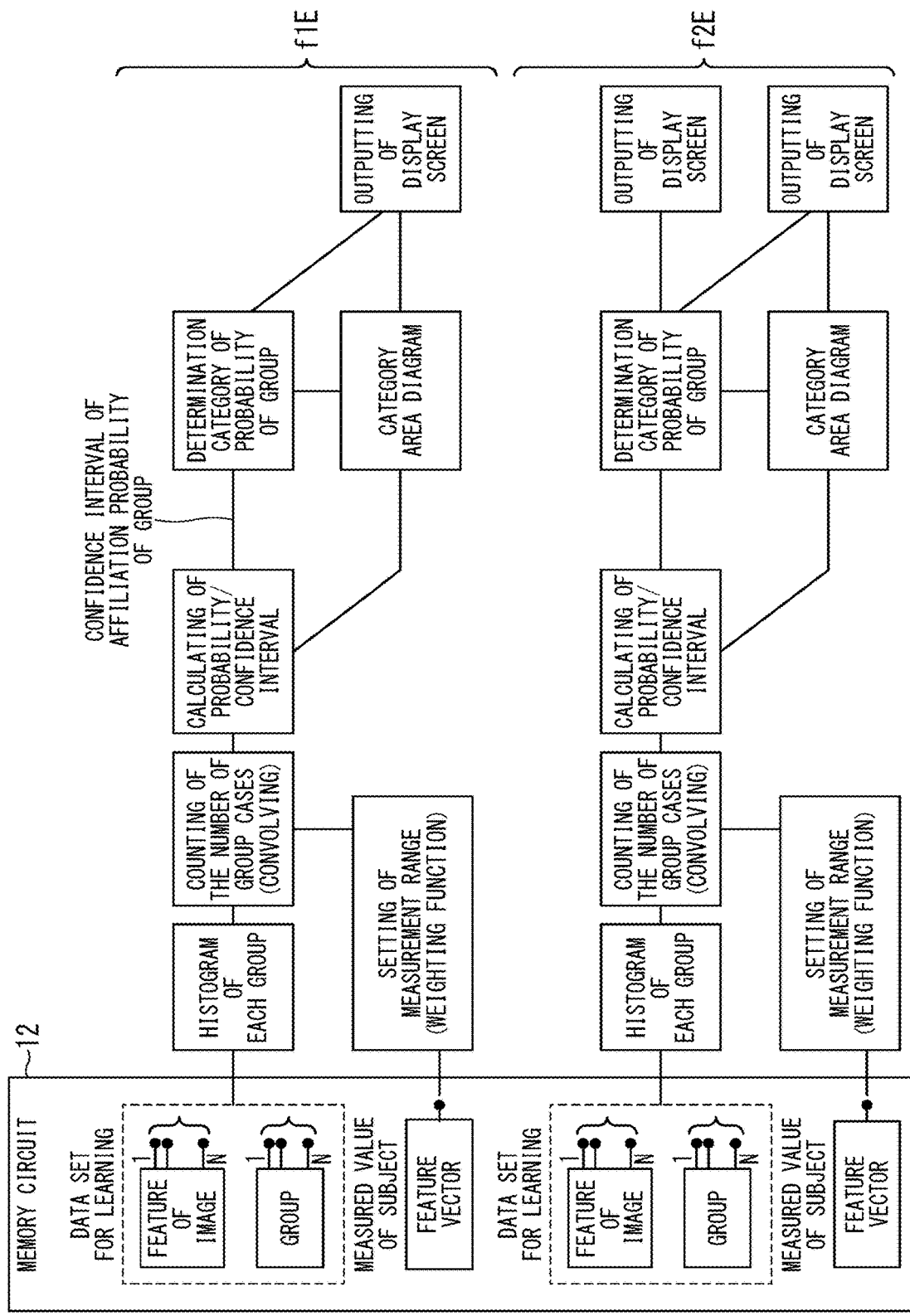

FIG. 23 is a data flow diagram showing the first-E function and the second-E function in the medical data processing apparatus according to the second embodiment.

Figure 24A:
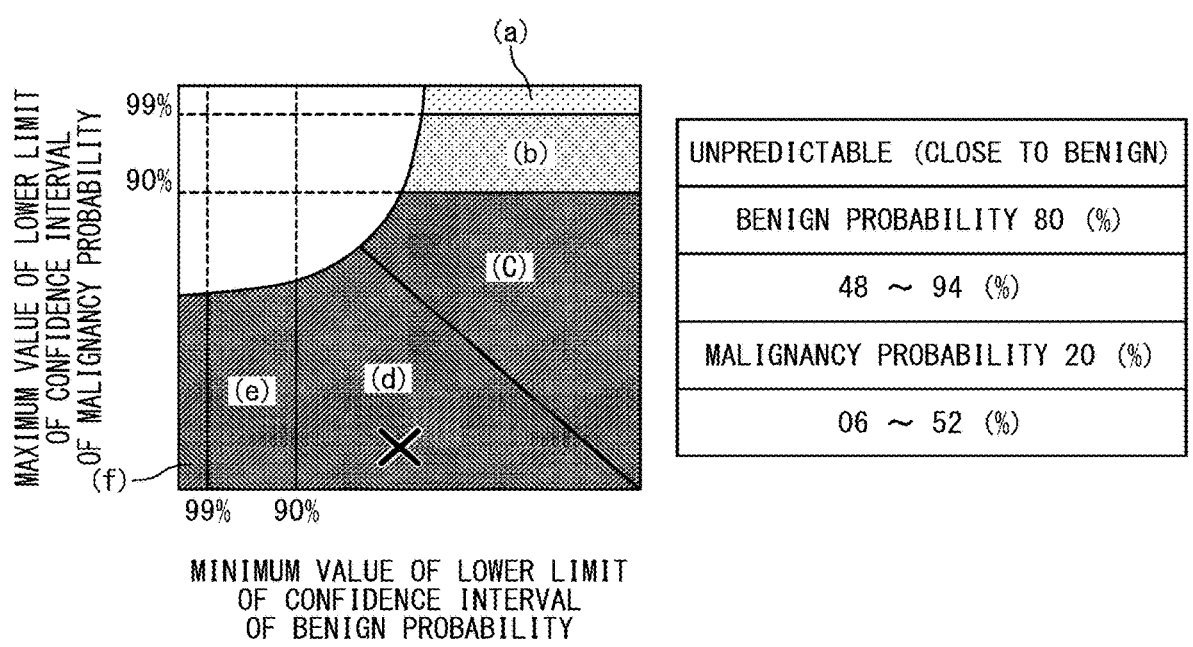
Figure 24B:
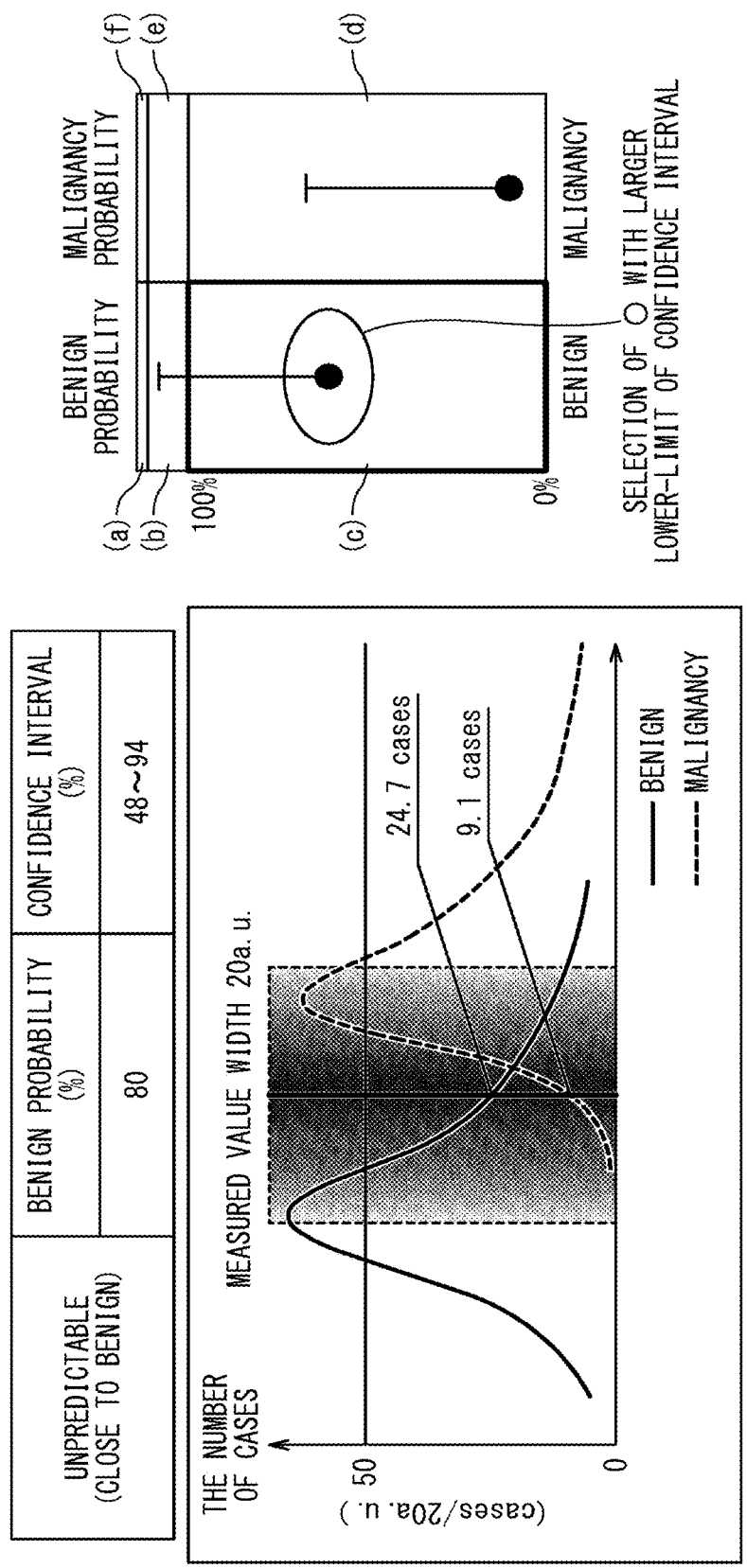

Each of FIGS. 24A and 24B is a diagram showing an example of a predicted result in the medical data processing apparatus according to the second embodiment.

Figure 25:
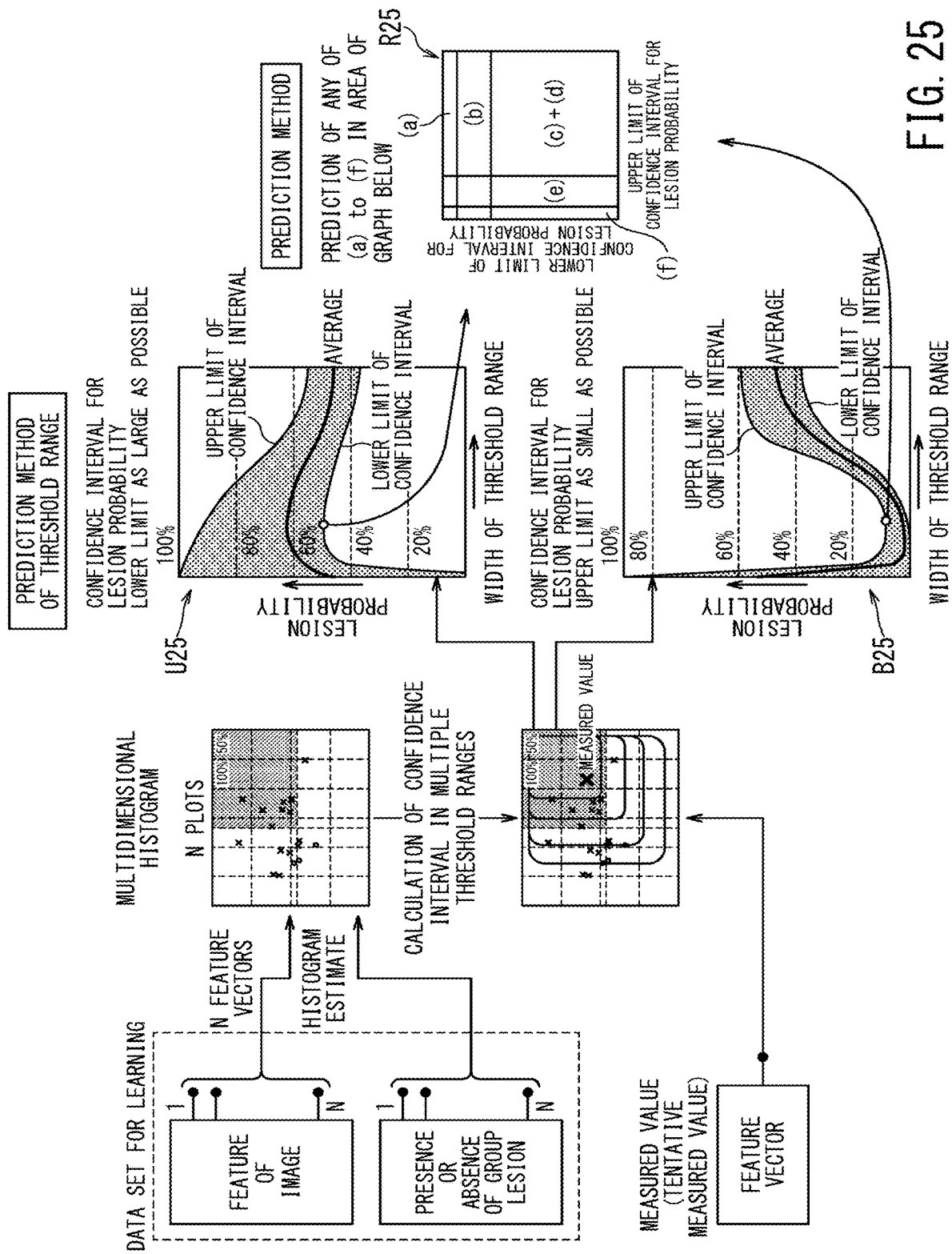

FIG. 25 is a diagram showing an example of a predicted result in the medical data processing apparatus according to the second embodiment.

Figure 26A:
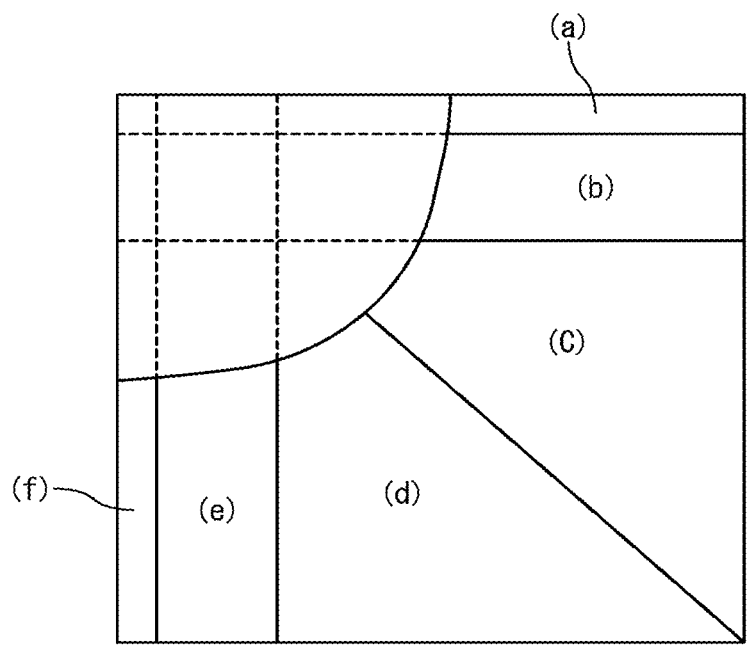
Figure 26B:
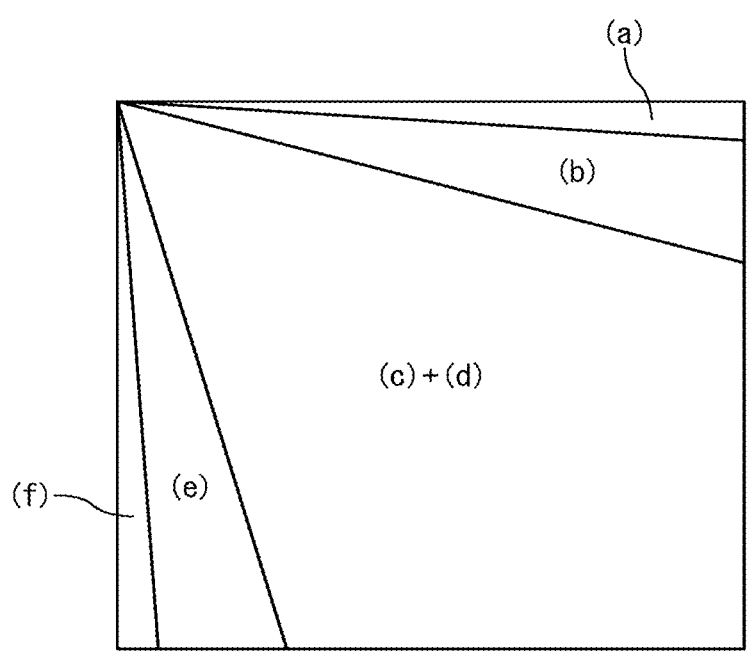

Each of FIGS. 26A and 26B is a diagram for explaining a predicted method in the medical data processing apparatus according to the second embodiment.

Figure 27:
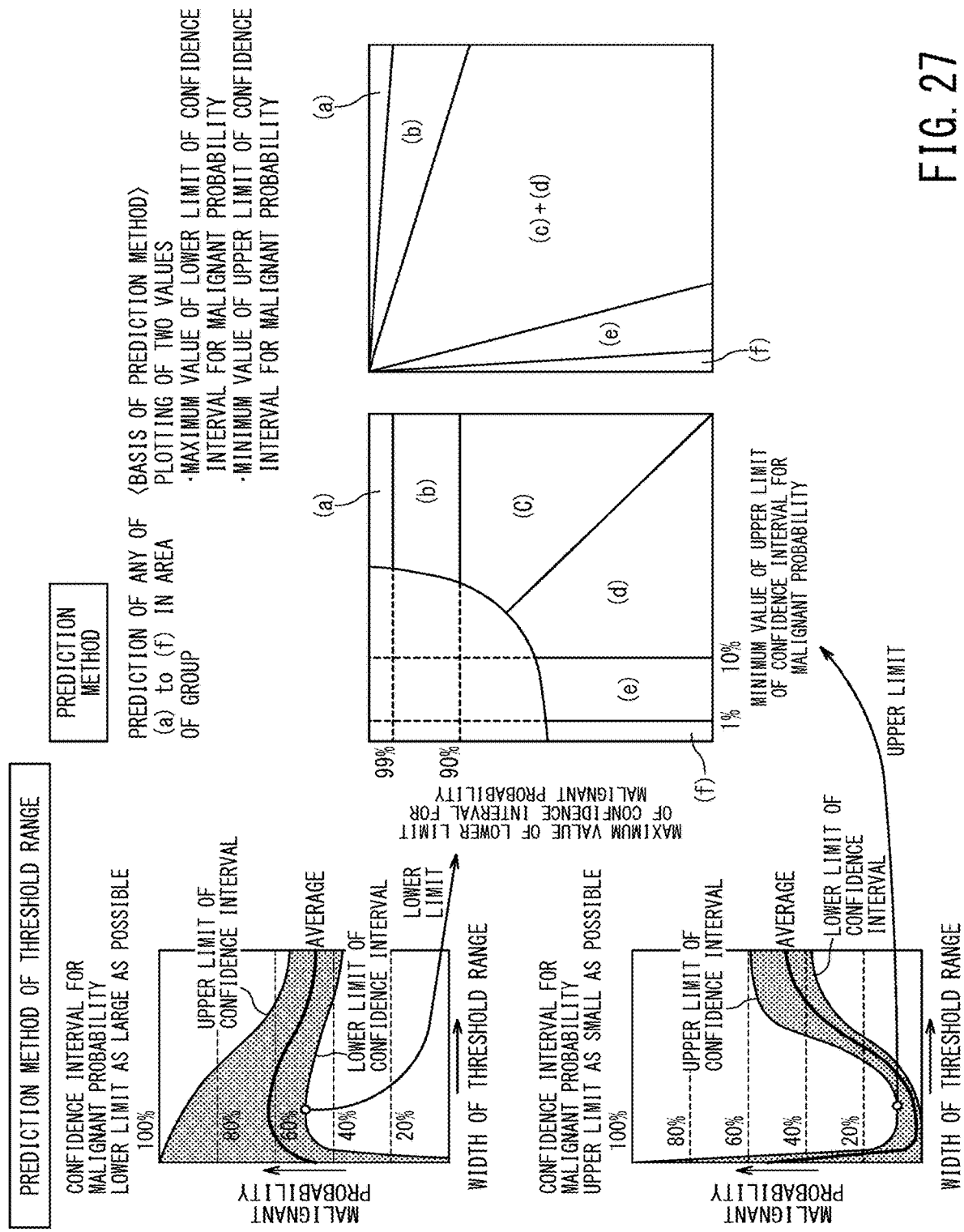

FIG. 27 is a diagram for explaining a predicted method in the medical data processing apparatus according to the second embodiment.

Figure 28:
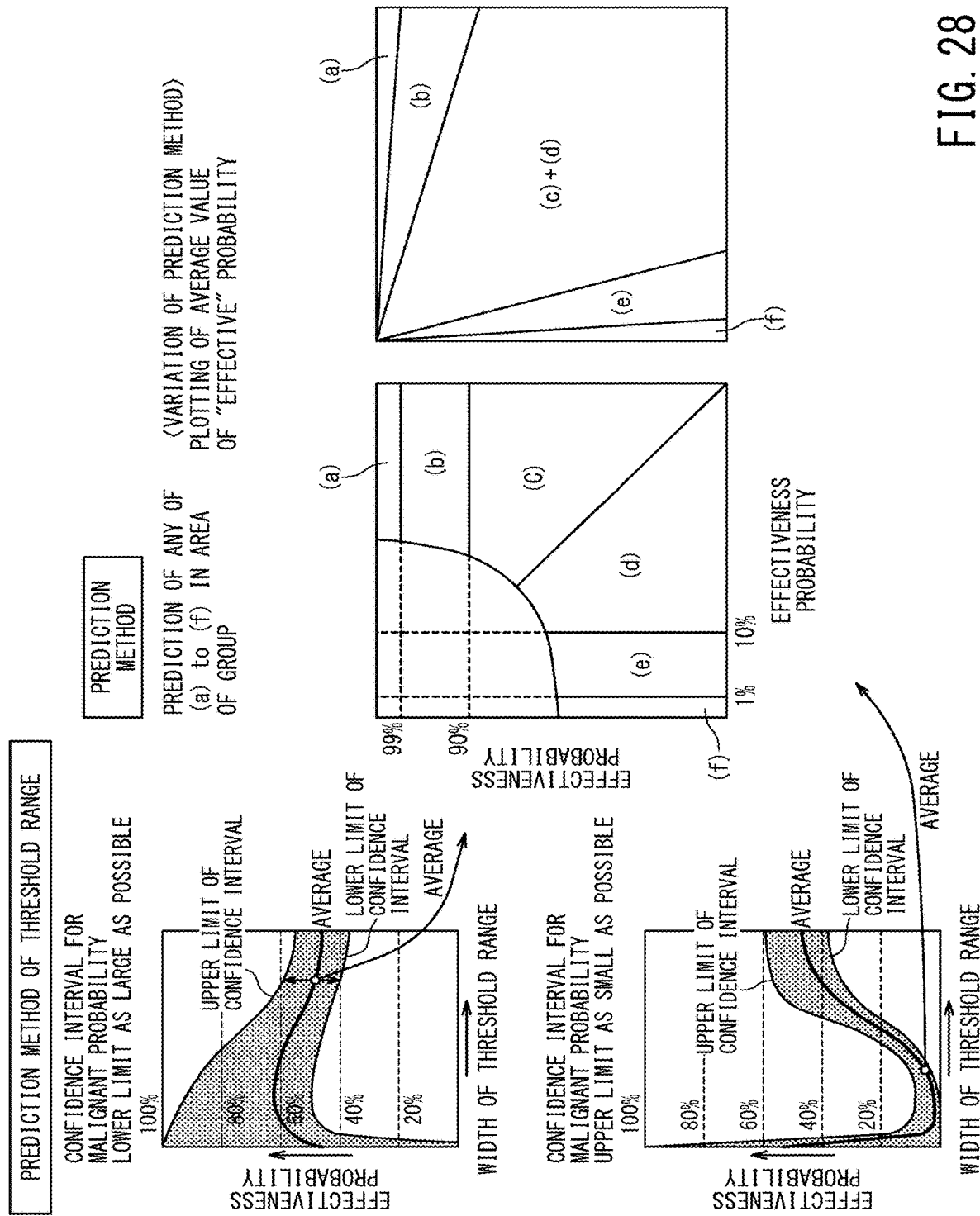

FIG. 28 is a diagram for explaining a predicted method in the medical data processing apparatus according to the second embodiment.

Figure 29:
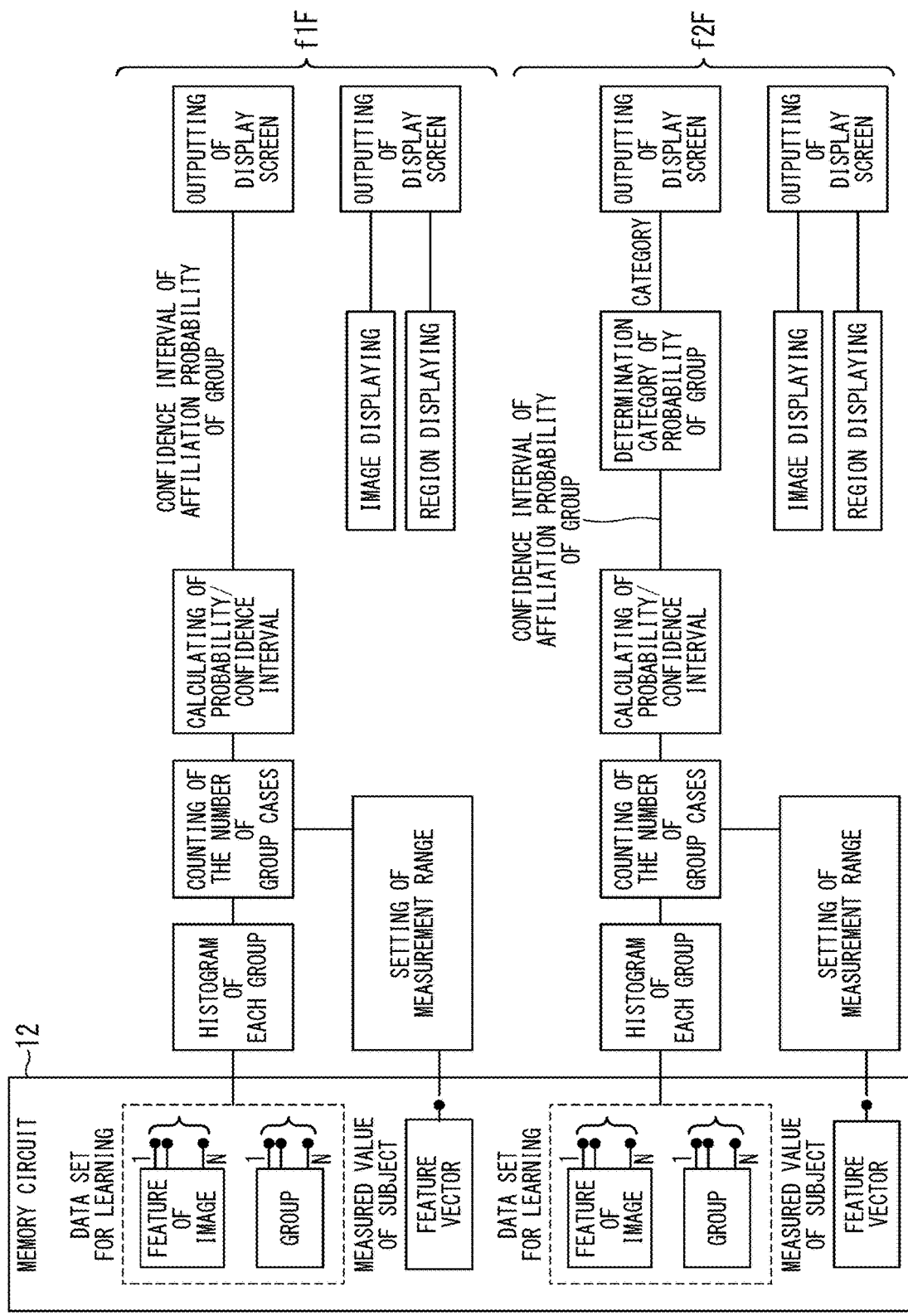

FIG. 29 is a data flow diagram showing the first-F function and the second-F function in the medical data processing apparatus according to the second embodiment.

Figure 30:
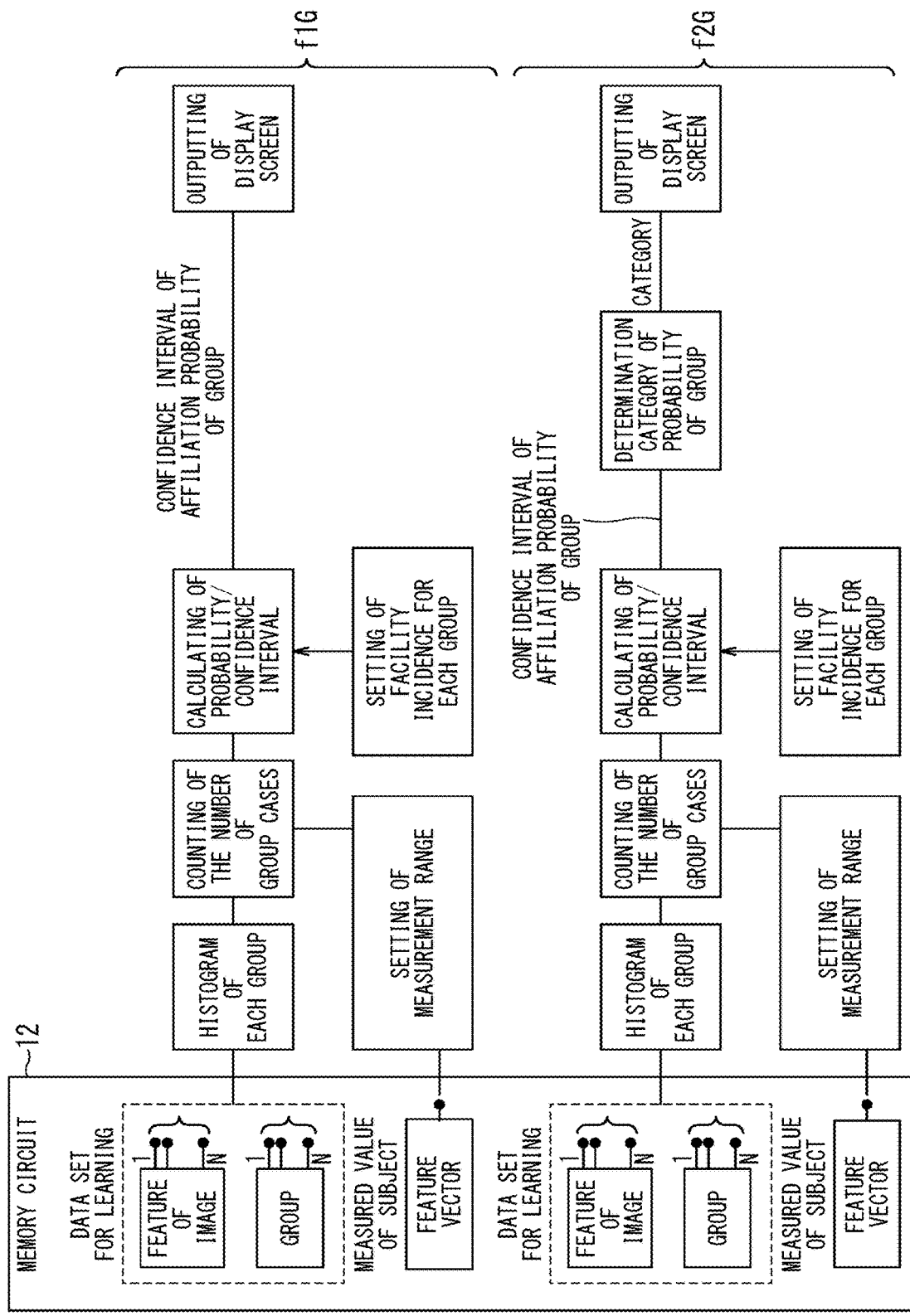

FIG. 30 is a data flow diagram showing the first-G function and the second-G function in the medical data processing apparatus according to the second embodiment.

Figure 31:
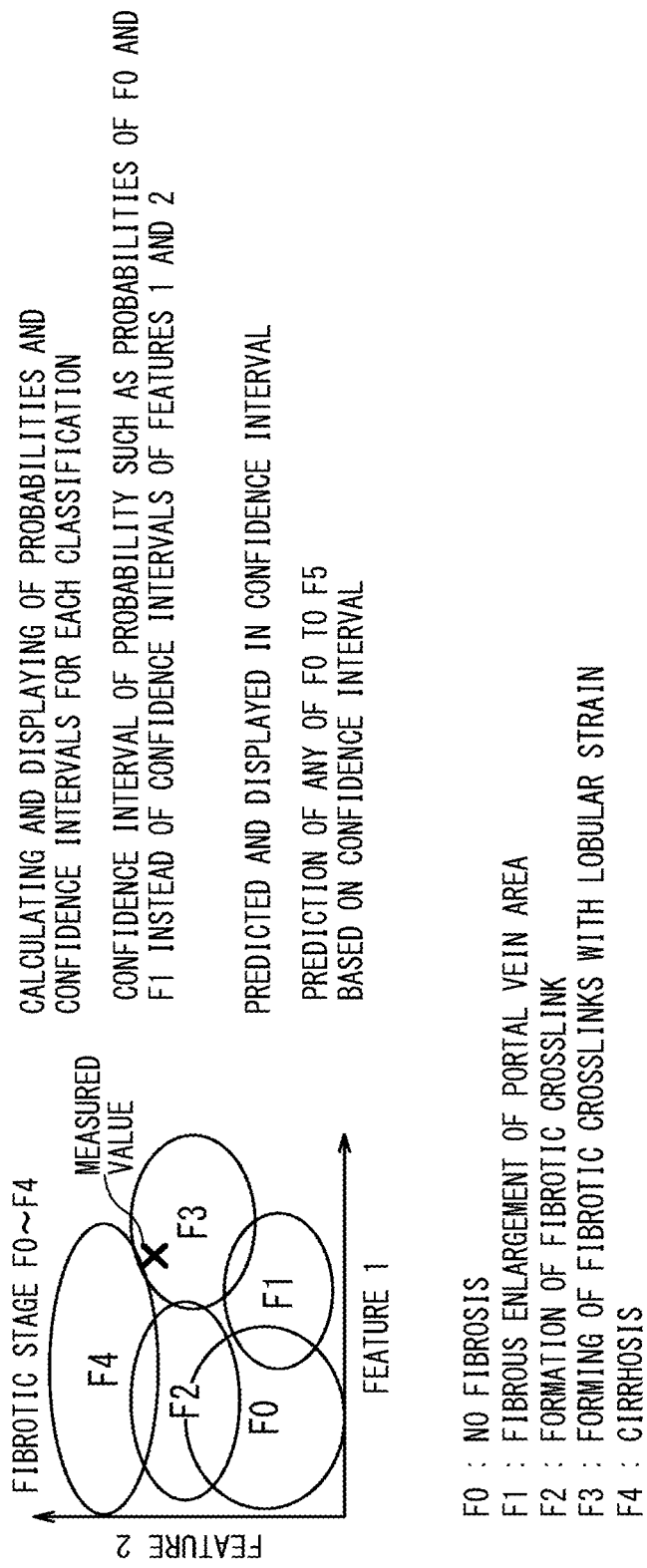

FIG. 31 is a diagram showing an example of a predicted result in the medical data processing apparatus according to the second embodiment.

Figure 32:
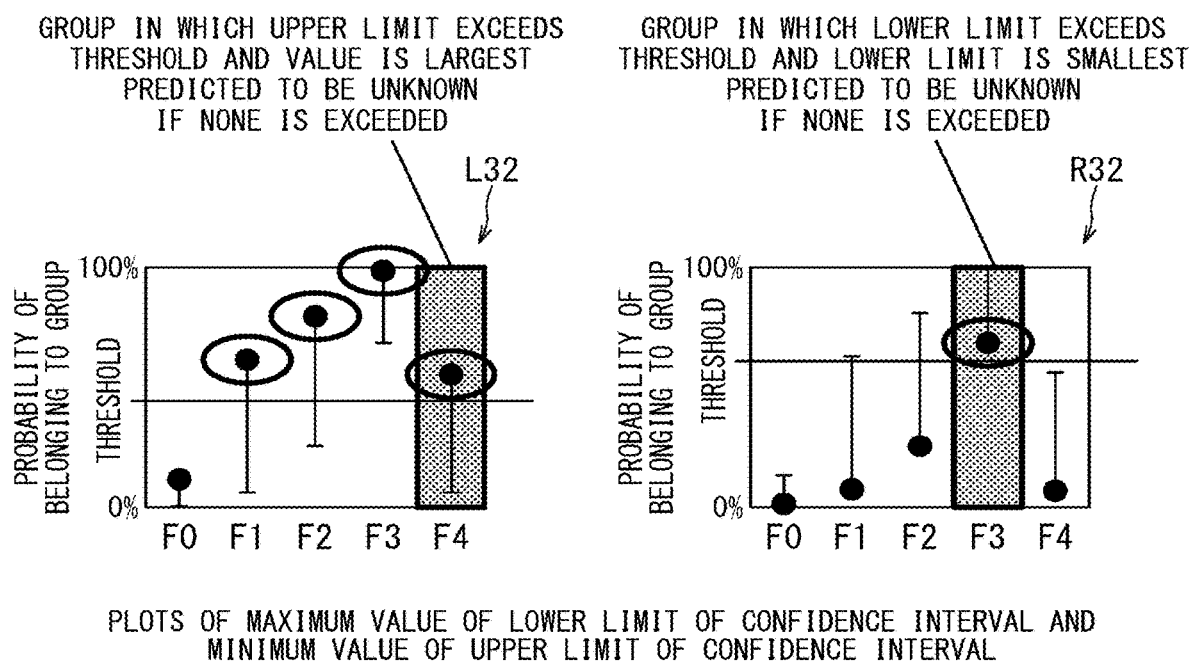

FIG. 32 is a diagram showing an example of a predicted result in the medical data processing apparatus according to the second embodiment.

Figure 33:
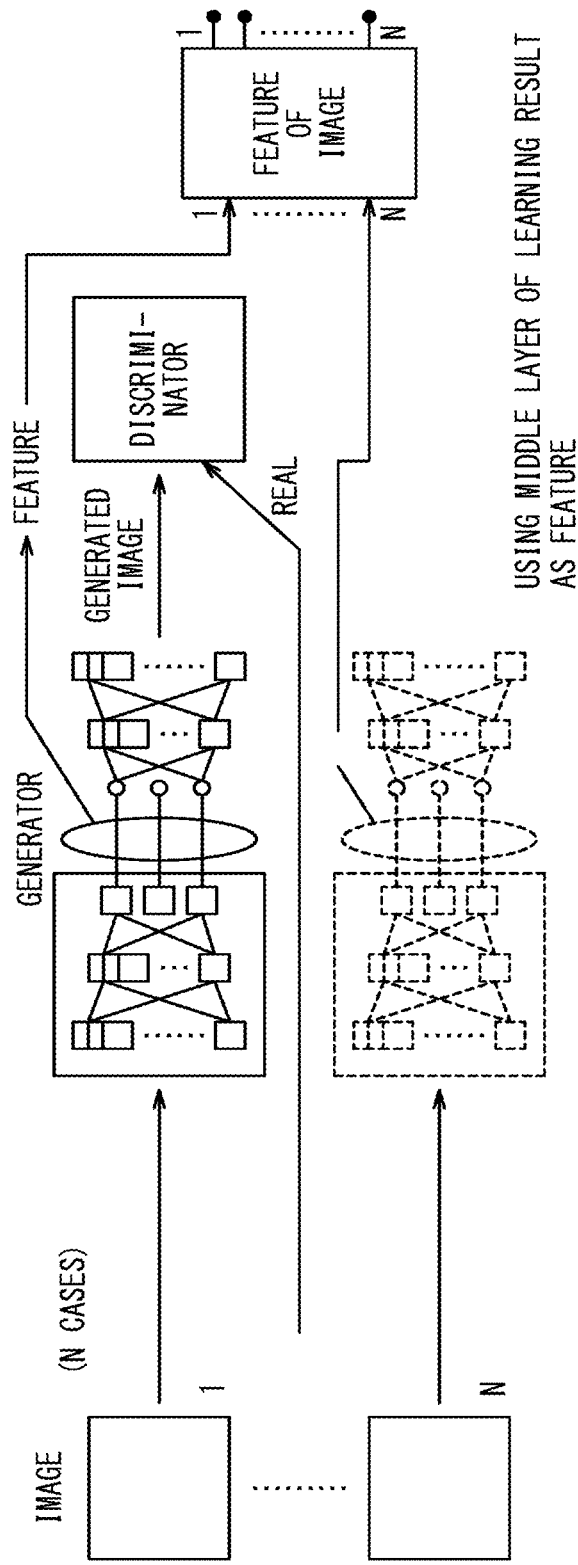

FIG. 33 is a diagram showing a configuration of a hostile generation network.

Figure 34:
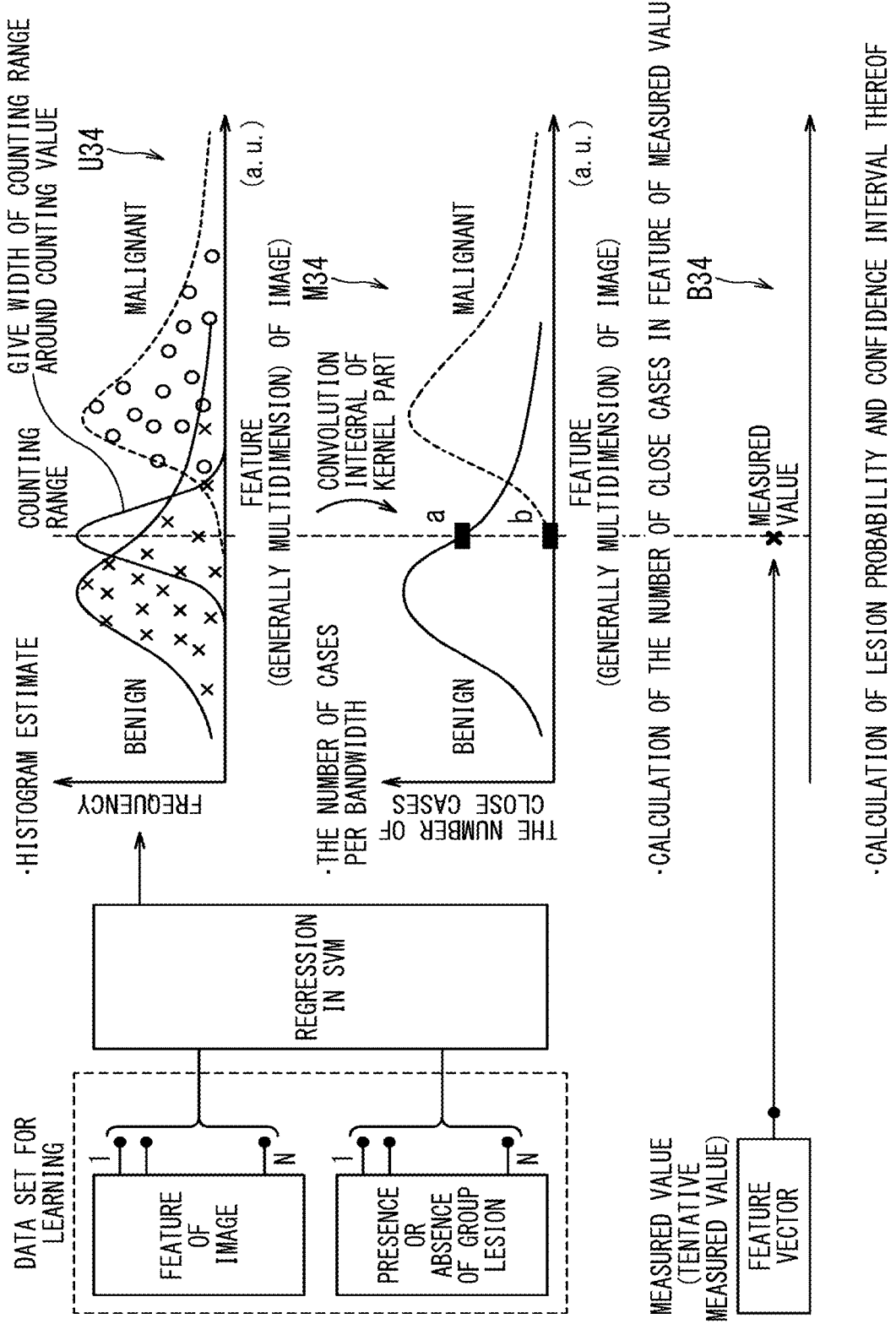

FIG. 34 is a diagram for explaining a method of calculating a confidence interval in the medical data processing apparatus according to the second embodiment.

Figure 35A:
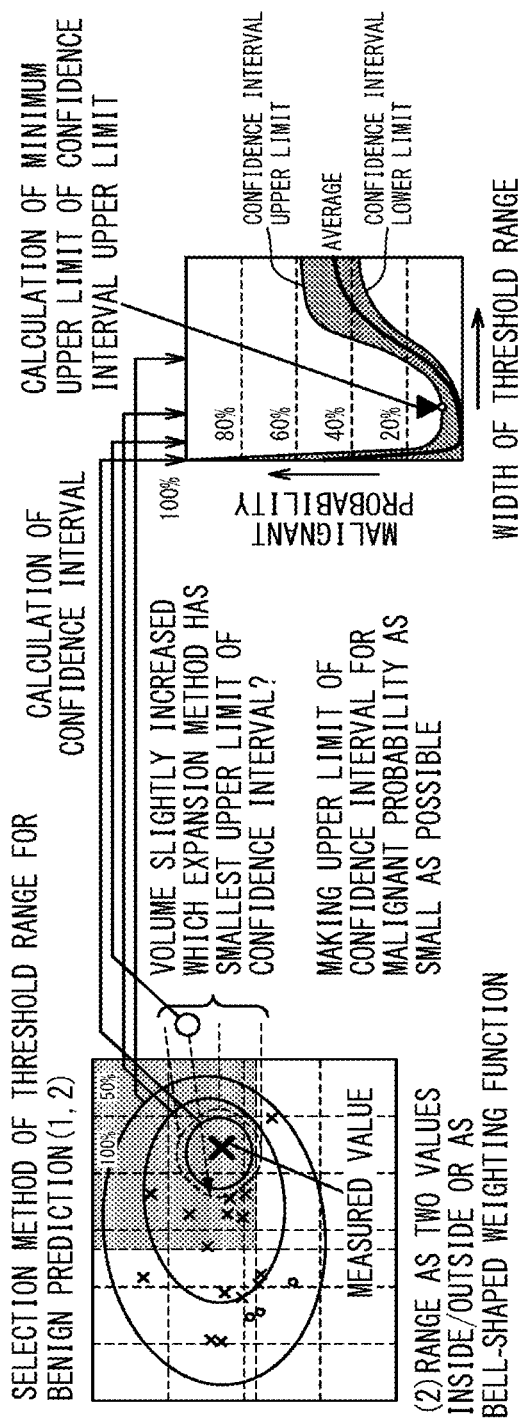
Figure 35B:
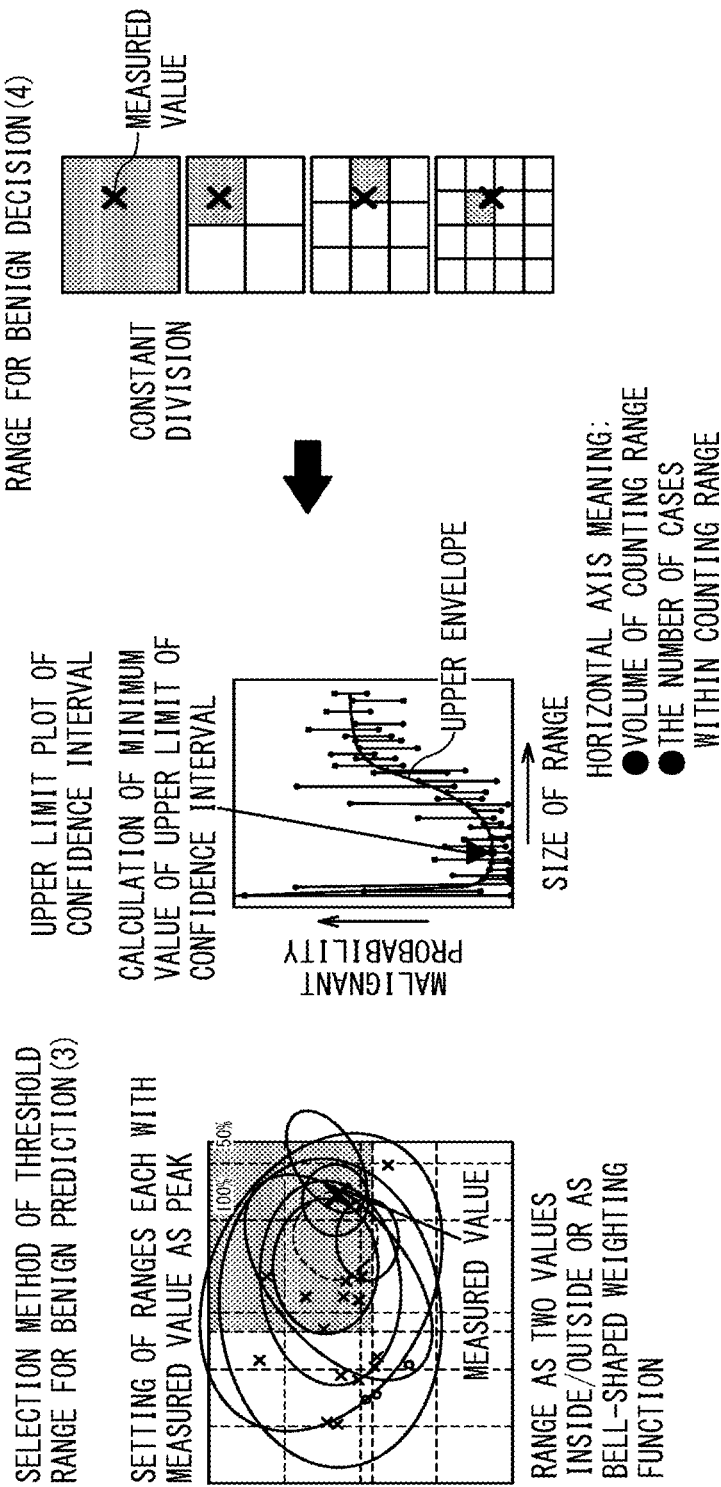

Each of FIGS. 35A and 35B is a diagram for explaining a method of correcting a confidence interval in the medical data processing apparatus according to the second embodiment.

FIG. 36 is a diagram showing an example of a predicted result in the medical data processing apparatus according to the second embodiment.

FIG. 37 is a diagram showing an example of a predicted result in the medical data processing apparatus according to the second embodiment.

FIG. 38 is a diagram showing an example of a predicted result in the medical data processing apparatus according to the second embodiment.

Each of FIGS. 39A and 39B is a diagram showing an example of a predicted result in the medical data processing apparatus according to the second embodiment.

Each of FIGS. 40A and 40B is a diagram showing an example of a predicted result in the medical data processing apparatus according to the second embodiment.

Each of FIGS. 41A to 41F is a diagram showing an example of a predicted result in the medical data processing apparatus according to the second embodiment.

Figure 42:
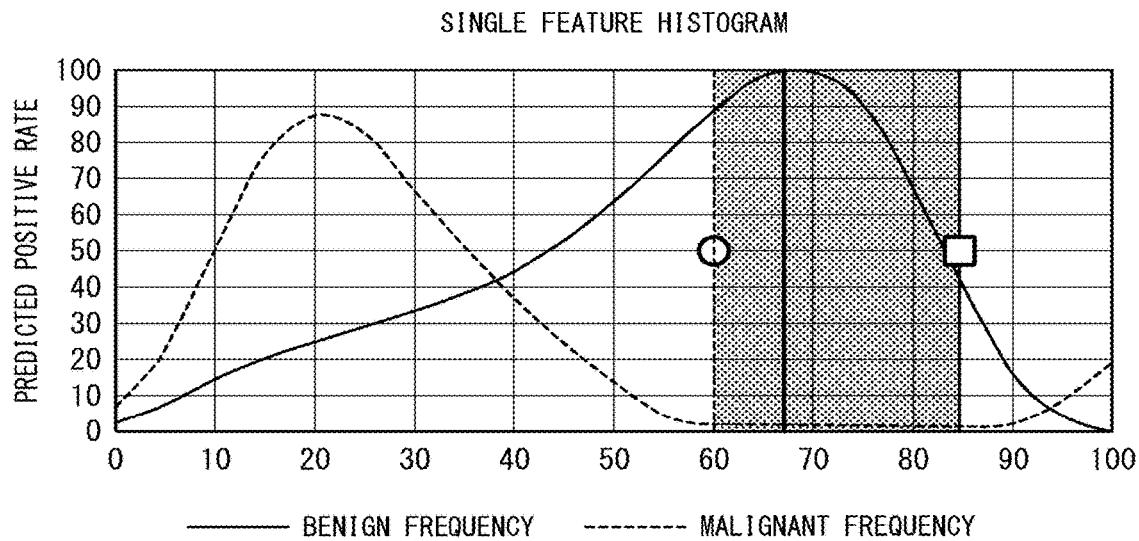

FIG. 42 is a diagram showing an example of a user interface in the medical data processing apparatus according to the second embodiment.

Figure 43:
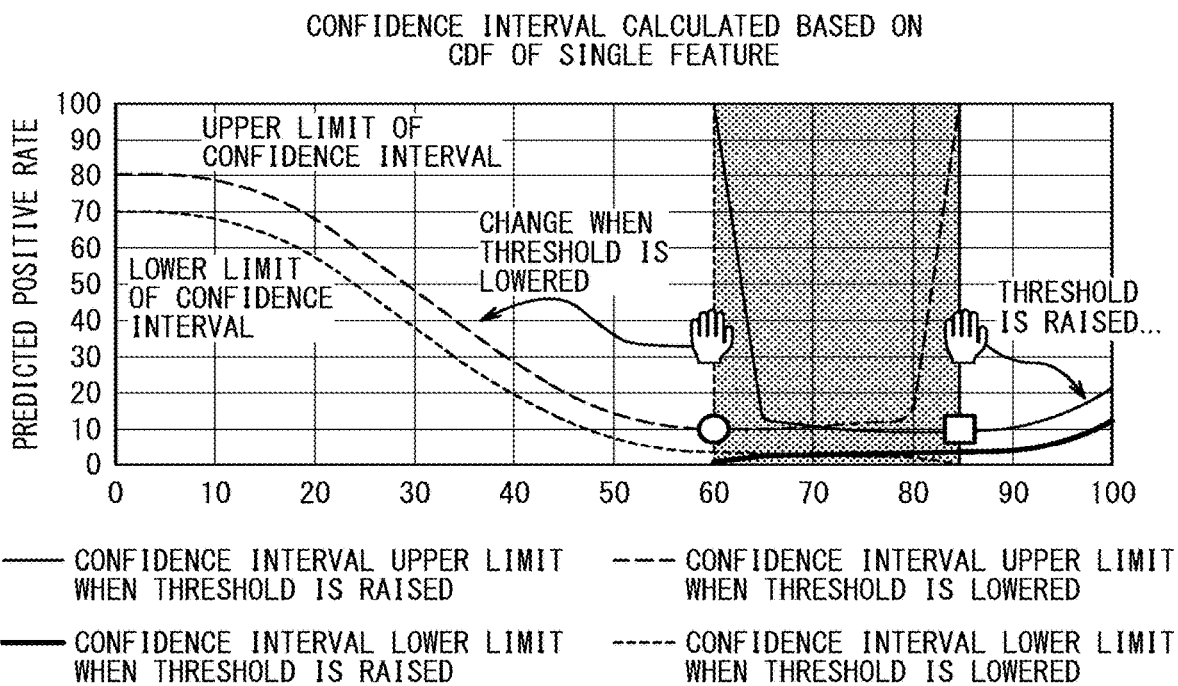

FIG. 43 is a diagram showing an example of a user interface in the medical data processing apparatus according to the second embodiment.

Figure 44:
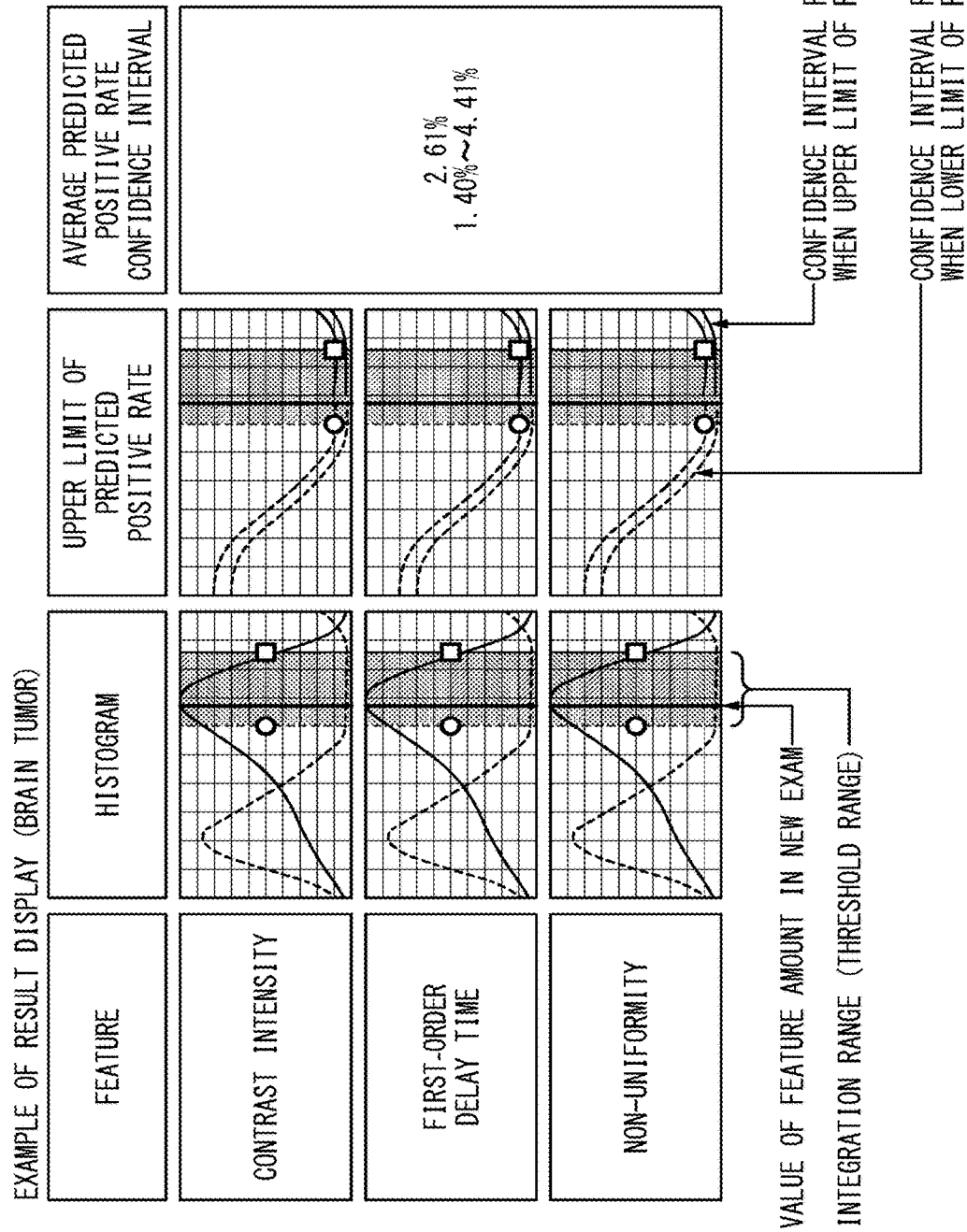

FIG. 44 is a diagram showing an example of a user interface in the medical data processing apparatus according to the second embodiment.

DETAILED DESCRIPTION

A medical data processing apparatus, a medical data processing method, and a non-transitory computer medium storing computer program according to any of embodiments will be described with reference to the accompanying drawings.

The medical data processing apparatus according to any of embodiments includes processing circuitry. The processing circuitry is configured to calculate a probability that target image data has a lesion and a confidence interval indicating a reliability of the probability, and to output data on the lesion based on the probability and the confidence interval of the probability.

An object of any of the embodiments is to output data on the lesion based on a probability (hereinafter referred to as "lesion probability") that the subject of the image actually has the lesion and the confidence interval which is an interval indicating the reliability of the lesion probability. In addition to the presence or absence of the lesion, the data on the lesion includes various lesion-related information such as the type of lesion, low and high value of the prognosis, the appropriateness of treatment, and the like. Further, probability designates the probability of categories defined in the data on the lesion. A case of calculating the lesion probability and the confidence interval only for one or more reliable image patterns that the confidence interval of "negative predictive value/positive predictive value" is relatively narrow and reliable among multiple image patterns (hereinafter, simply referred to as "patterns") will be described with reference to the first embodiment. The positive predictive value (PPV) means the ratio at which the cases predicted to be positive were actually positive. The negative predictive value (NPV) means the ratio at which the negative cases were actually negative. Further, a case where the confidence interval of the probability of the data on the lesion is calculated based on the feature value of the image data of the subject and the lesion probability is calculated based on the confidence interval will be described in the second embodiment.

First Embodiment

Figure 1:
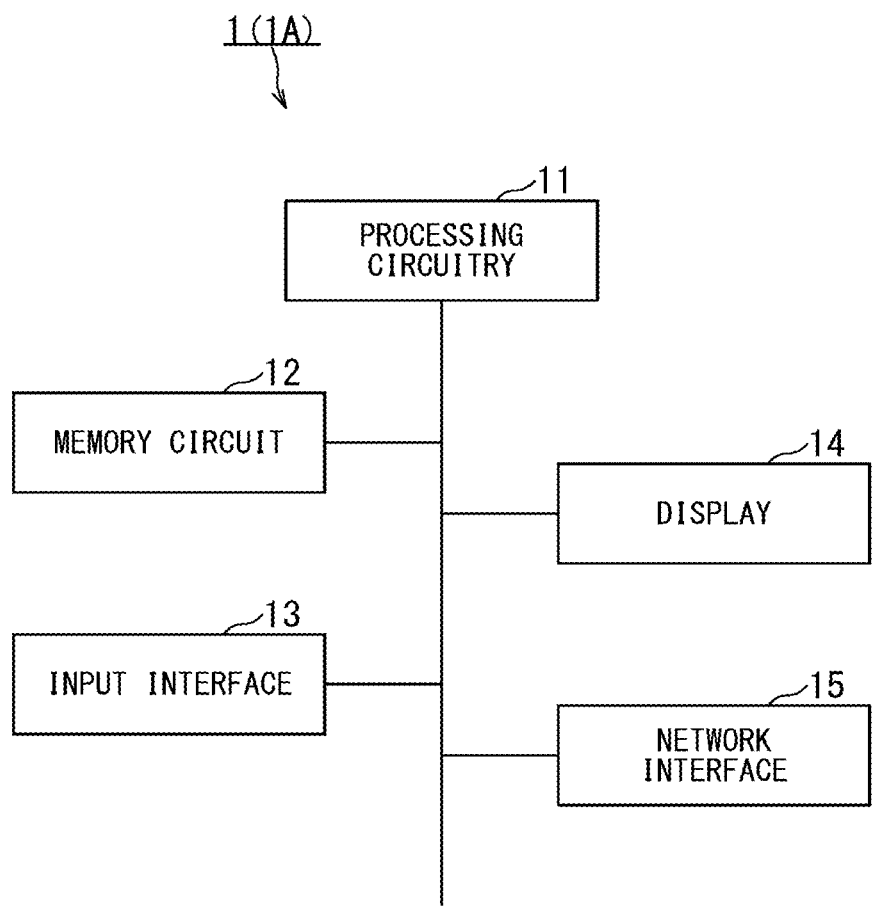
FIG. 1 is a schematic view showing a configuration example of a medical data processing apparatus according to the first embodiment.

FIG. 1 is a schematic view showing a configuration example of a medical data processing apparatus according to the first embodiment.

FIG. 1 shows a medical data processing apparatus 1 according to the first embodiment. The medical data processing apparatus 1 is a medical image managing apparatus (image server), a workstation, an image-interpretation terminal, or the like, and is provided on a medical image system connected via a network. The medical data processing apparatus 1 may be an offline device.

The medical data processing apparatus 1 includes processing circuitry 11, a memory circuit 12, an input interface 13, a display 14, and a network interface 15.

The processing circuitry 11 refers to an ASIC, a programmable logic device, etc. in addition to a dedicated or general purpose central processing unit (CPU), or a microprocessor unit (MPU). The programmable logic device may refer to, for example, a simple programmable logic device (SPLD), a complex programmable logic device (CPLD), a field programmable gate array (FPGA). The processing circuitry 11 realizes functions described later by reading and executing a program stored in the memory circuit 12 or directly incorporated in the processing circuitry 11.

Further, the processing circuitry 11 may be constituted by a single circuit or a combination of independent circuit elements. In the latter case, the memory circuit 12 may be provided individually for each circuit element, or a single memory circuit 12 may store programs corresponding to the functions of the circuit elements. The processing circuitry 11 is an example to a processor.

The memory circuit 12 is constituted by a semiconductor memory element such as a random-access memory (RAM), a flash memory, a hard disk, an optical disk, or the like. The memory circuit 12 may be constituted by a portable medium such as a universal serial bus (USB) memory and a digital video disk (DVD). The memory circuit 12 stores various processing programs (including an operating system (OS) and the like in addition to the application program) used in the processing circuitry 11 and data necessary for executing the program. The OS may include a graphical user interface (GUI), which makes extensive use of graphics when displaying data on the display 14 to an operator such as an image-interpreter, and performs basic operations using the input interface 13.

In addition, the memory circuit 12 stores images generated by a medical image diagnostic apparatus such as an X-ray computed tomography (CT) apparatus and a magnetic resonance imaging (MRI) apparatus. The memory circuit 12 is an example of a memory unit.

The input interface 13 includes an input device operable by an operator, and a circuit for inputting a signal from the input device. The input device may be a trackball, a switch, a mouse, a keyboard, a touch pad for performing an input operation by touching an operation surface, a touch screen in which a display screen and a touch pad are integrated, a non-contact input circuit using an optical sensor, an audio input circuit, and the like. When the input device is operated by the operator, the input interface 13 generates an input signal corresponding to the operation and outputs it to the processing circuitry 11. The medical data processing apparatus 1 may include a touch panel in which the input device is integrally configured with the display 14. The input interface 13 is an example of an input unit.

The display 14 is constituted by a display device such as a liquid crystal display, a plasma display panel, or an organic light emitting diode (OLED) display. The display 14 displays medical image under the control of the processing circuitry 11. The display 14 is an example of a display unit.

The network interface 15 is configured by composed of connectors that meet the parallel connection specifications and the serial connection specifications. The network interface 15 has a function of performing communication control according to each specification and being connectable to a network through a telephone line. Thereby, the network interface 15 can connect the medical data processing apparatus 1 to the network. The network interface 15 is an example of a network connecting unit.

Figure 2:
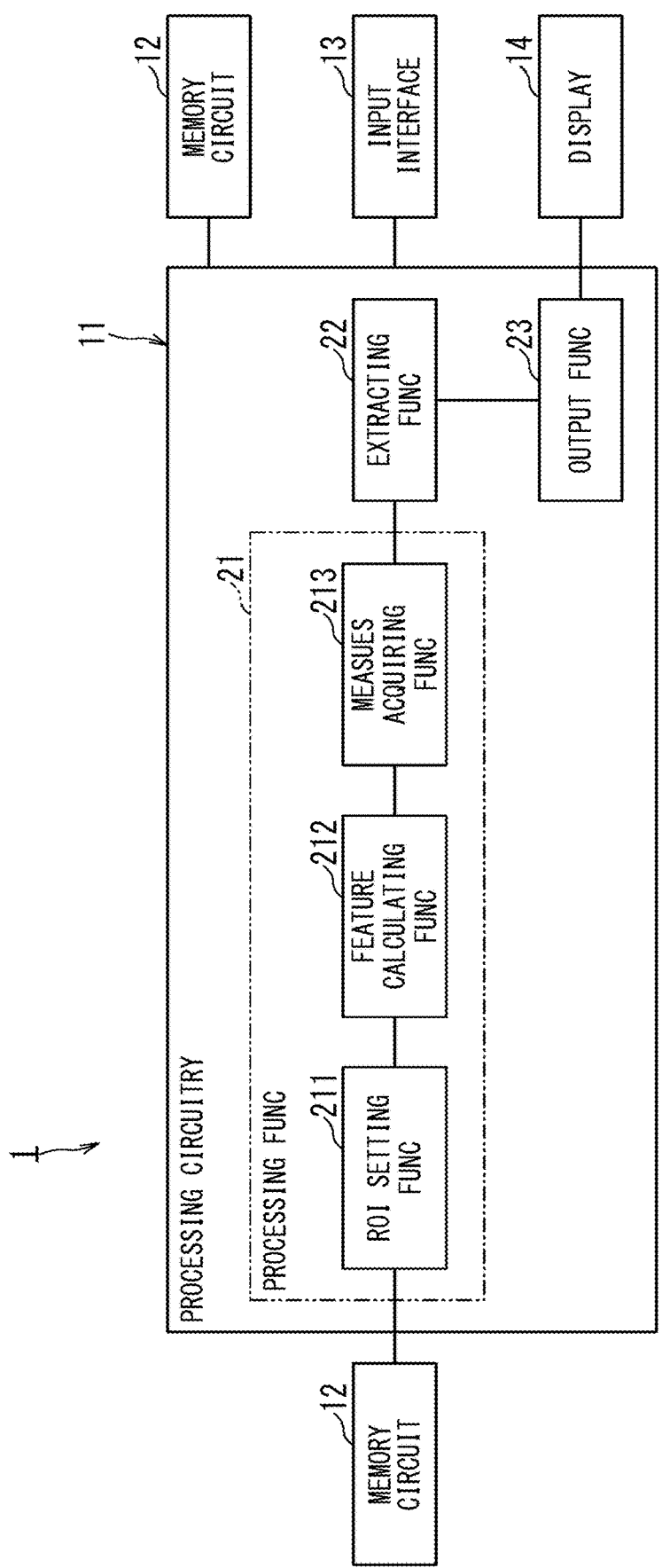
FIG. 2 is a block diagram showing functions of the medical data processing apparatus according to the first embodiment.

FIG. 2 is a block diagram showing functions of the medical data processing apparatus 1.

The processing circuitry 11 executes a computer program stored in a non-transient recording medium such as the memory circuit 12, thereby the medical data processing apparatus 1 realizes the processing function 21, the extracting function 22, and the output function 23. All or part of the functions 21 to 23 may be realized as a circuit such as an ASIC in the medical data processing apparatus 1.

The processing function 21 includes a function of classifying image data of a subject for determination into multiple patterns and calculating a measure value indicating the lesion probability of each pattern as a classification reasonability scale. For example, the processing function 21 generates the classification reasonability scale by inputting the image data of the subject into a trained model that generates the classification reasonability scale based on the image data of the subject. For example, the lesion probability is the benign/malignant probability of the mass. The processing function 21 is an example of a processing unit.

The extracting function 22 includes a function of extracting a part of patterns by which the lesion is easily identified from the multiple patterns based on the classification reasonability scale of each pattern of the multiple patterns. The extracting function 22 is an example of an extracting unit.

The output function 23 includes a function of preferentially outputting a part of the patterns extracted by the extracting function 22. For example, the output function 23 includes a function of generating a display where a part of the patterns extracted by the extracting function 22 is prioritized, and of displaying the display screen on the display 14. The output function 23 is an example of an output unit.

The processing function 21 includes a region of interest (ROI) setting function 211, a feature calculating function 212, and a measures acquiring function 213.

The ROI setting function 211 includes a function of extracting an ROI from each image data of a training image data set including multiple cases in a design stage. In addition, the ROI setting function 211 includes a function of extracting the ROI based on the image data of a new case in an examination stage. That is, the ROI setting function 211 sets the ROI of the image data of the subject, thereby being able to classify the image data of the subject into multiple patterns based on the ROI. The ROI setting function 211 is an example of an ROI setting unit.

The feature calculating function 212 includes a function of calculating features as a feature vector on the basis of the ROI of each image data in the design stage extracted by the ROI setting function 211, and of calculating a classification measure vector based on the feature vector. Further, the feature calculating function 212 includes a function of calculating the features as a feature vector on the basis of the ROI of the image data in the examination stage extracted by the ROI setting function 211, and of calculating a classification measure vector based on the feature vector. The feature calculating function 212 is an example of a feature calculating unit.

The measures acquiring function 213 includes a function of acquiring distribution data of the classification measure vector of each group in the examination stage and the lesion probability of a new case (assumed to be uniform if distribution is unknown). The measures acquiring function 213 directly acquires the classification measure vector belonging to the group (class) from the feature calculating function 212. In the present specification and drawings, the attributes of multiple target image data to be used, such as lesion-presence or lesion-absence (or no lesion), are referred to as "groups". The measures acquiring function 213 acquires the parameters of the statistical distribution of the classification measure vector of each group of the feature calculating function 212. The measures acquiring function 213 is an example of the measures acquiring unit.

The extracting function 22 includes a function of acquiring classification criteria for classifying each pattern and a display condition of the pattern from the classification measure vector acquired by the measures acquiring function 213, and of calculating reference data such as a predicted lesion probability based on the distribution of the classification measure vector of each group (and the classification measure vector of the ROI) for each of the pattern candidates. The extracting function 22 includes a function of calculating a potential scale for identifying by the pattern as an classification reasonability scale for each of the pattern candidates, and of determining a combination of patterns to be displayed based on the calculation. The extracting function 22 includes a function of setting a display flag according to a value of a classification vector, pattern classification criteria, and a group scale (the pattern classification criteria is generally a pattern weighting function).

The output function 23 has a function of displaying a name of the pattern and reference data (group scale data) of each pattern on the display 14 on the basis of the display flag extracted and set by the extracting function 22.

In the comparative example, the relationship between the categories for classification and the target image data is presented as user's reference. As an example, the categories are defined corresponding with lesion names, and images of cases near to a typical case of the lesion category is presented to provide data for visually reviewing whether or not the presented images of the lesion class are close to the target image. In addition, a degree of typical image that indicating whether the target image is near to a typical image of the lesion category is presented. These are data that can be used as a reference for diagnosis. However, the presented similar images are not always useful in the situation where the image-interpreter confirms whether the predicted result is appropriate because subjective image features on the classification are not presented in this example. Moreover, presented images are not useful for recording of decision process. Decision process and an additional confirmation process are needed to be described in language as a record of the decision (description in medical records and creation of diagnostic report). Then, the reference data presented by the conventional example may not be useful data for the image-interpreter to confirm and record the decision process.

For recording of the image-interpreter's additional confirmation process and the decision process, it is necessary to present reference data from a viewpoint different from the purpose of classification. For example, it is important to present data other than whether or not a person has a cold, such as the presence or absence of symptoms such as coughing and body temperature to decide if a cold is had or to record the decision process. In addition, the reference data presented needs to be able to be expressed as a language rather than something like a similar image. Furthermore, in order to use it for the purpose of diagnostic imaging, the reference data presented cannot be directly measured such as the presence or absence of symptoms and body temperature, but needs to be data that represents the characteristics of the image data.

Therefore, it is assumed that the medical data processing apparatus 1 includes the processing function 21, the extracting function 22, and the output function 23.

The specific operations of the functions 21 to 23 will be described later with reference to FIGS. 3 to 11.

Figure 3:
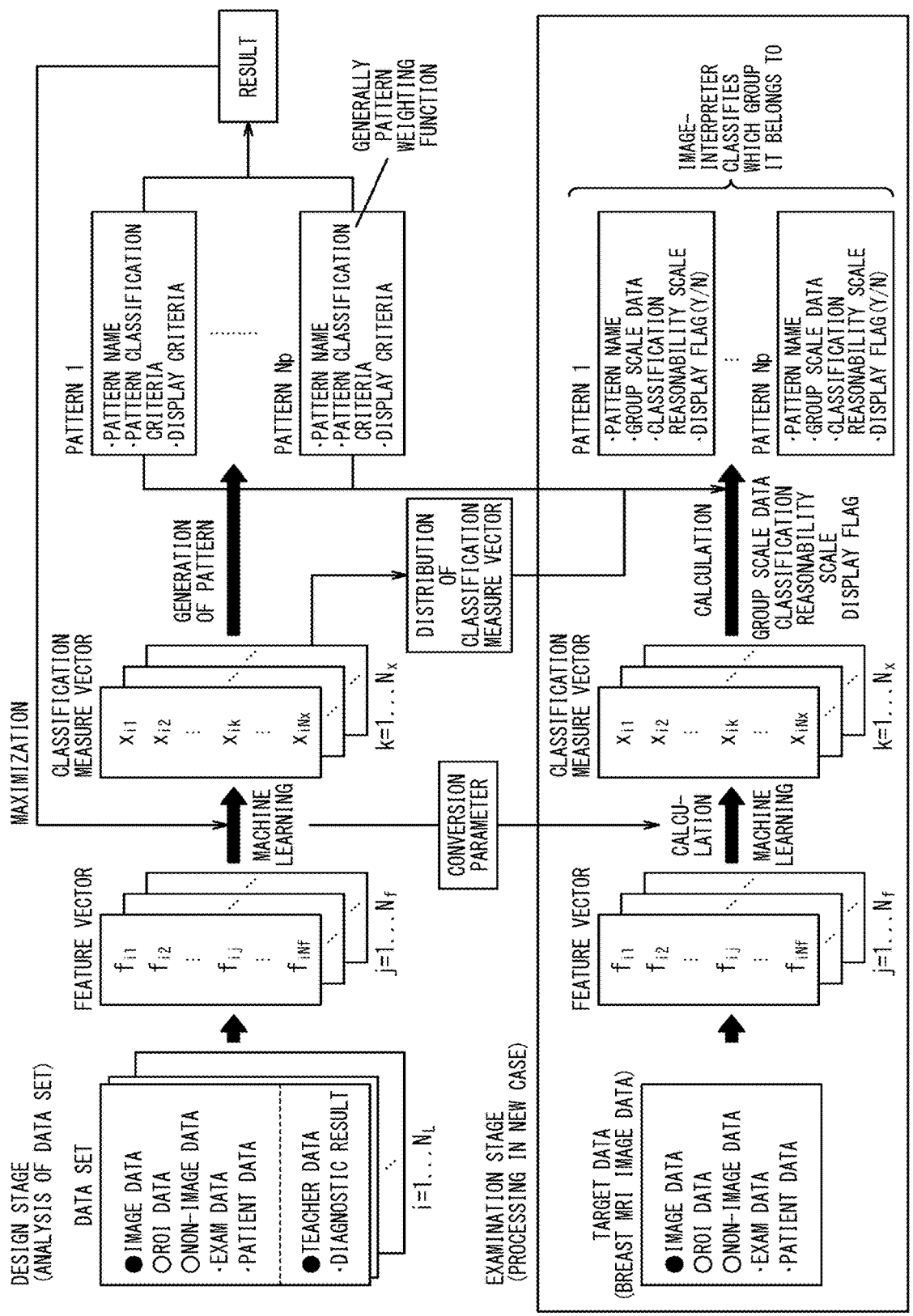
FIG. 3 is a diagram for assisting an explanation of the functions of the medical data processing apparatus according to the first embodiment.

FIG. 3 is a diagram for assisting an explanation of the functions of the medical data processing apparatus 1.

A case where the medical data processing apparatus 1 sets a lesion area of the image data, thereby identifying a lesion state in the lesion area, for example, "negative" or "positive", based on the presented data and the observation result of the image data will be described here. The data presented is decision reference data that is used as a reference for the image-interpreter to make a decision of "negative" or "positive".

As the data in an examination stage for constructing the classification method, for example, $N_L$ breast MR image data is used. For each of the $N_L$ breast MR image data, "benign" or "malignant" is given as teacher data of training data based on the result of established diagnosis. Here, "positive" designate prediction results corresponding with malignant lesion and "negative" designate prediction result corresponding with benign lesion.

The medical data processing apparatus 1 generates a pattern consisting of pattern names and the like by calculating the classification measure vector $N_x$ based on the data set consisting of the $N_L$ cases. Then, the classification result of patters obtained by the data set consisting of $N_L$ cases is computed with the image data in an examination stage and presented to the image-interpreter as decision reference data. The image-interpreter can easily identify "negative" or "positive" based on the presented decision reference data. Further, the image-interpreter can review the examination image data by comparison with the decision reference data, and confirm whether the classification is appropriate. Thereby, the image-interpreter can also correct the classification to make his/her decision, if necessary.

The medical data processing apparatus 1 displays multiple patterns as decision reference data. The medical data processing apparatus 1 displays, as a pattern, a name representing the feature of the image data; reference data as to whether or not the examination image data belongs to the pattern; and reference data for determining whether the examination image data in the pattern is benign or malignant. Instead of always displaying the same pattern, only the necessary patterns are displayed. The display or non-display of a pattern is determined based on a value (classification reasonability scale) indicating whether the classification in the pattern likely be reasonable.

When designing such an prediction method, "PPV<constant" is introduced as a design condition that an discrimination performance having a smaller value of positive predictive value (PPV) than defined value. Furthermore, design goals are set so that the discrimination performance with "maximum specificity" can be expected. For example, the constant is "0.05", which means the discriminating performance such that "PPV<0.05". Under this condition, if it is determined that the region of interest is classified into a certain pattern in the examination, the probability that the ROI is malignant is required to be 5% or less. That is, the classified pattern is designed so that the lesion is highly likely to be benign.

Furthermore, since the goal is to have maximum specificity, the pattern is designed so that the possibility of miss-discrimination of benign lesion to malignant is reduced. Conditions and goals can also be set using other criteria such as sensitivity and negative predictive value (NPV).

The medical data processing apparatus according to the embodiment includes two stages (1) and (2) in the following processing.

(1) design stage (classification of data set)
(2) examination stage (processing in new case)

The above (1) design stage is to analyze the probability distribution of the teacher data set and save the result. The design step may be performed only once before a new case in an examination stage is given.

The above (2) examination stage is a processing of the examination stage executed for each new case. In this processing, one of the new cases will be processed and data that can be used as a reference for decision will be presented.

Where to divide the processing in each of the above (1) and (2) stages is arbitrary, but the processing will be described below based on a typical example.

Figure 4:
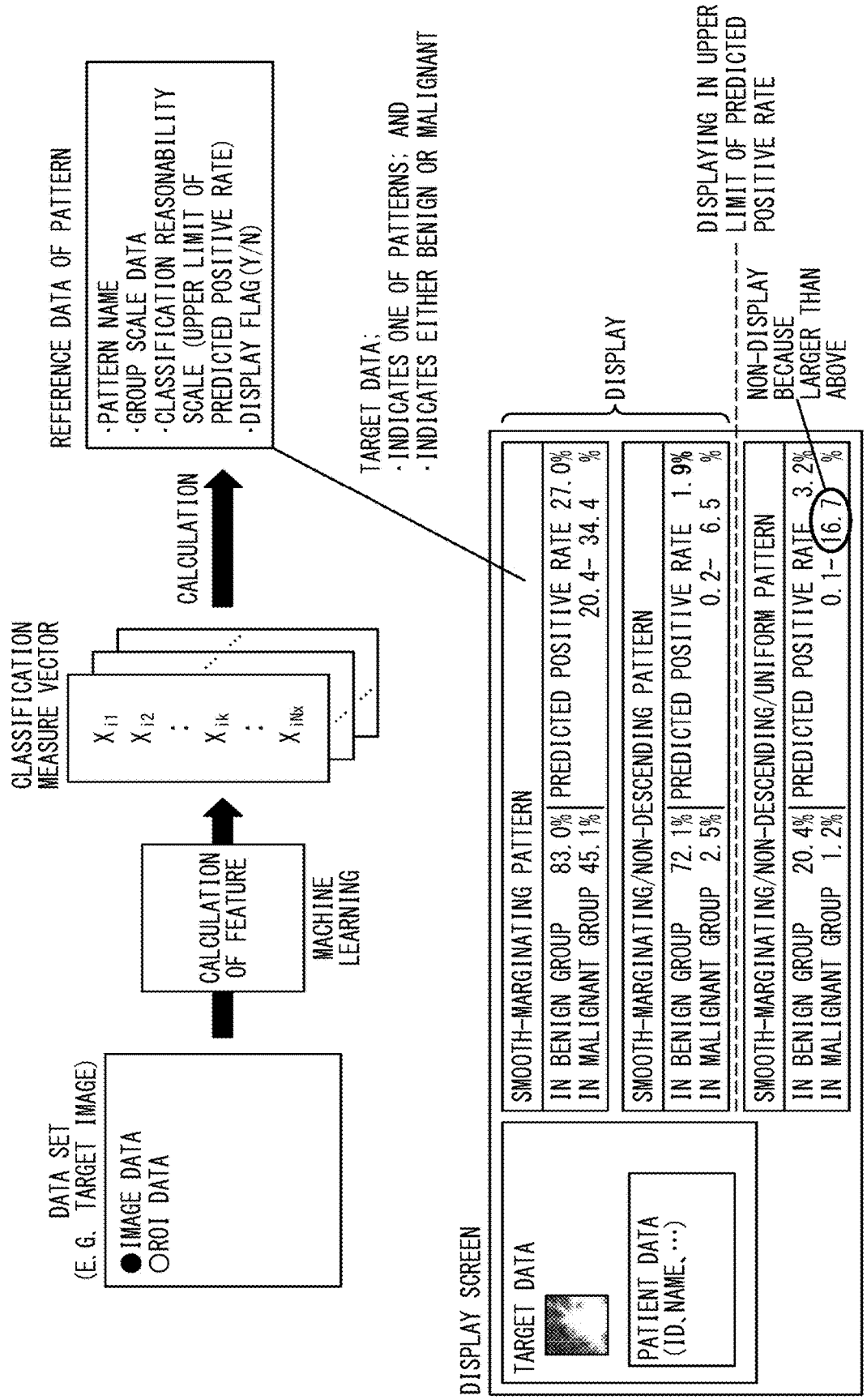
FIG. 4 is a diagram showing an outline of functions of the medical data processing apparatus according to the first embodiment.

FIG. 4 is a diagram showing an outline of functions of the medical data processing apparatus 1.

As shown in FIG. 4, the processing function 21 inputs the image data of the subject into the trained model that generates the classification reasonability scale based on the image data of the subject, thereby generating a classification reasonability scale. The extracting function 22 extracts a part of the patterns where the lesion is easily identified from the multiple patterns, on the basis of the classification reasonability scale of each pattern of the multiple patterns. The output function 23 preferentially outputs a part of the patterns extracted by the extracting function 22 (display screen on the lower side of FIG. 4).

Figure 5:
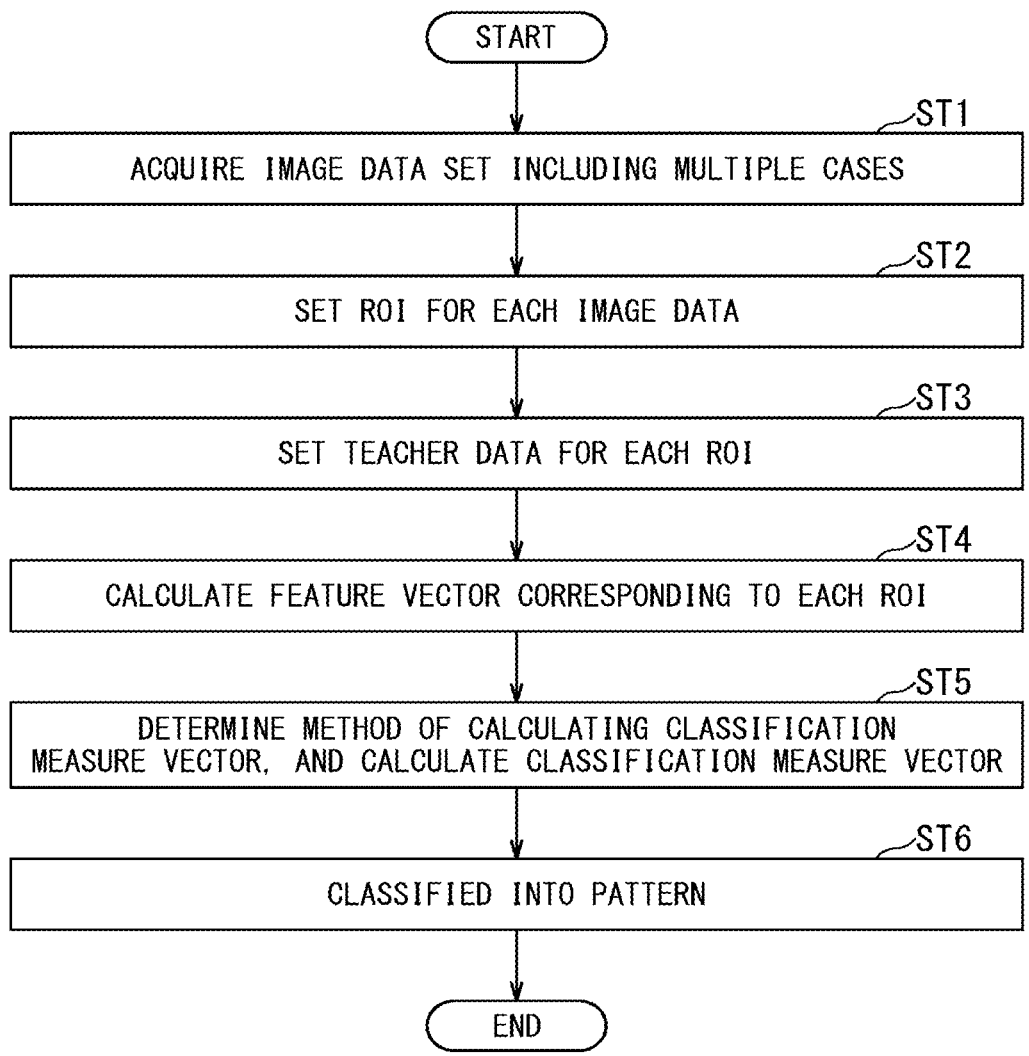
FIG. 5 is a diagram showing an operation of the medical data processing apparatus according to the first embodiment in the design stage as a flowchart.
Figure 6:
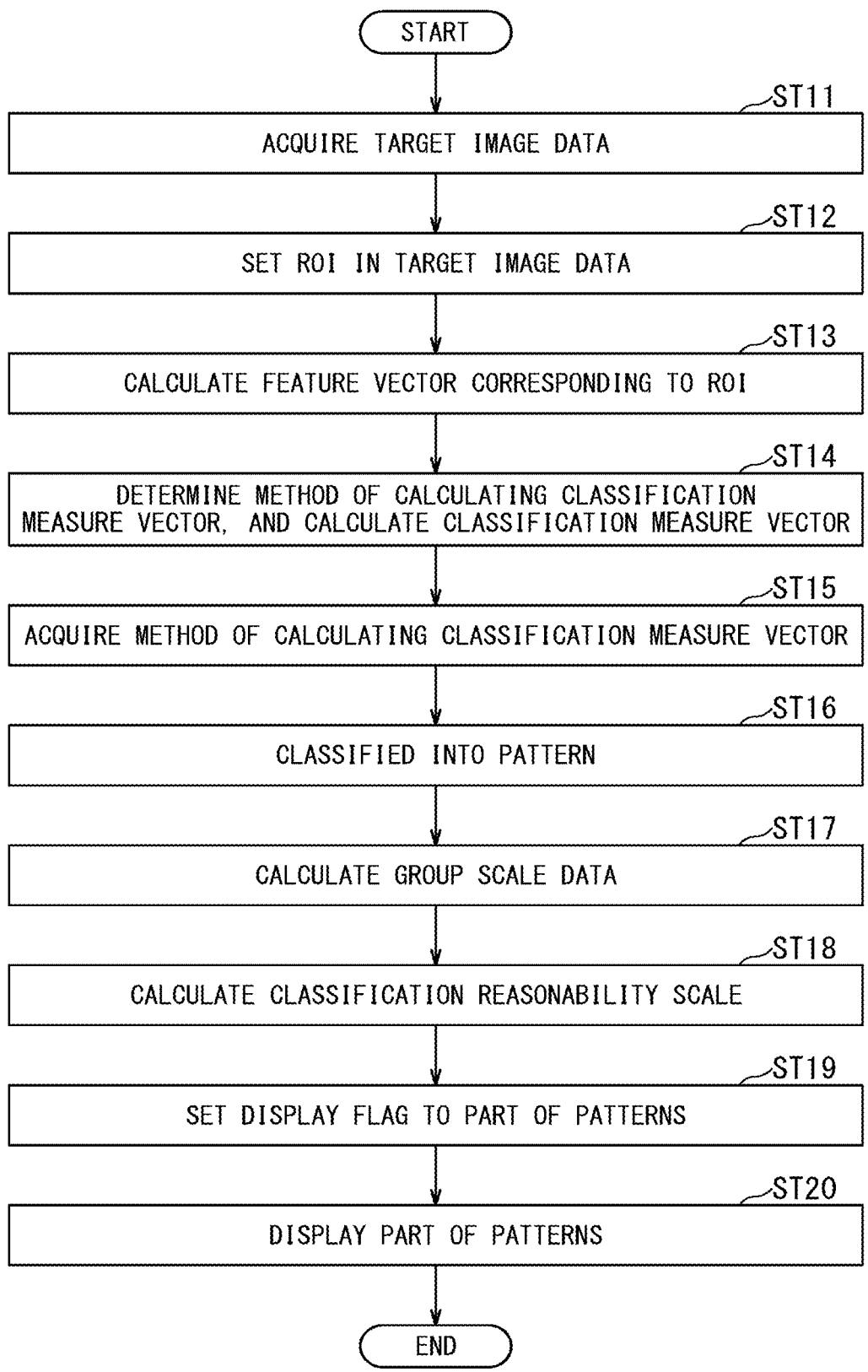
FIG. 6 is a diagram showing an operation of the medical data processing apparatus according to the first embodiment in the examination stage of the decision reference data as a flowchart.

FIG. 5 is a diagram showing an operation of the medical data processing apparatus 1 in the design stage as a flowchart. FIG. 6 is a diagram showing an operation of the medical data processing apparatus 1 in the examination stage of the decision reference data as a flowchart. In FIGS. 5 and 6, the reference numeral "ST" with a number indicates each step of the flowchart.

The processing function 21 acquires an image data set including multiple cases (step ST1). The ROI setting function 211 sets ROI for each image data in the image data set (step ST2). In step ST2, for example, the ROI setting function 211 extracts an analysis target region, for example, a tumor region, and sets it as the ROI based on the breast MRI image data collected in the contrast MRI of breast cancer. The ROI setting function 211 sets a total number of $N_L$ ROIs based on $N_L$ breast MRI image data including multiple cases.

The feature calculating function 212 sets teacher data for each of the $N_L$ ROIs set in step ST2 (step ST3). As a specific example, the state of the mass, for example, "benign" or "malignant", is assigned to each ROI. Alternatively, each ROI may be assigned a mass state, such as negative, positive, normal, lesion, abnormal, and the like. In addition, three or more values may be assigned using a specific lesion name. In an application that the result of the established diagnosis is used as the teacher data, the teacher data can be given after the established diagnosis is acquired.

The feature calculating function 212 calculates multiple features corresponding to the multiple ROIs set in step ST2 as feature vectors (step ST4). In step ST4, the feature calculating function 212 expresses the j-th features with respect to the ROI i as $f_{ij}$ (shown in FIG. 3). Further, multiple features for the ROI i constitute a feature vector $F_i$.

For example, the feature is the average value of the initial enhancement ratio of the contrast dynamic image. The initial enhancement ratio is an average value in all pixels in the ROI of fraction of the subtraction of pixel values in pre-contrast and post-contrast image over the pre-contrast pixel value. The difference in pixel values is acquired by subtracting the pixel values of pre-contrast phase from the pixel values of the first phase or the second phase after contrast enhancement. In addition, the features may be various contrast-related parameters such as peak enhancement ratio and enhancement ratio in delayed phase, or may be an average of these. Further, the features may be not only an average value but also various statistics. A wide variety of features can be calculated by combining contrast-enhancement-related parameters and texture analysis values. Further, it may be a feature of a morphological image such as circularity. Usually, alignment processing and motion correction processing are applied to the contrast dynamic image.

The measures acquiring function 213 determines a method for calculating the classification measure vector, and calculates the classification measure vector by the calculation method (step ST5). The measures acquiring function 213 calculates the classification measure vector by converting the feature vector of each image data in the teacher data. This corresponds to, for example, determining the calculation method of the classification vector in Japanese Patent Application Laid-Open No. 2015-116319. The j-th classification scale of the ROI i is expressed as $x_{ij}$ (shown in FIG. 3). Multiple classification scales of the ROI i are represented by the classification measure vector $X_i$. The feature vector $F_x$ is represented by the following equation (1) by a model in relation to the classification measure vector $X_i$.

$$X_i = F_x(f_i; \text{model parameters}) \tag{1}$$

Appropriate model and model parameters can give linguistic meaning to the features represented by each element of the classification measure vector. Therefore, the measures acquiring function 213 determines the model parameters in step ST5 such that appropriate meaning is given to each element.

Each element of the classification scale (hereinafter, the element number is represented by k) is given a name according to the magnitude of its value. For example, the first element (k=1) of the classification measure vector $x_i$ is a measure of edge and shape complexity. A range of smaller value ($x_{ij} \leq T$) is given a name such as "smooth" or "simple", and a range of larger value ($x_{ij} > T$) is given a name such as "irregular" or "complex". The second element (k=2) of the classification measure vector $x_i$ has a small value when the latter half of the contrast curve descends (examples of names are "washout", "downslope", etc.), and a large value when the latter half does not descend (examples of names are "not washout", "not downslope", etc.).

The conversion parameters from the feature vector to the classification measure vector are determined by using various linear/nonlinear optimization methods based on the data of the entire region and the teacher data. Machine learning techniques such as artificial neural networks and random trees can also be applied (second modified example to be described later). A relatively simple method is to select only the appropriate elements of the feature vector and use them as the classification measure vector. Specifically, when two variables are classified by the two elements among the combinations of the two elements, the combination that maximizes the scale of the reasonability of the classification can be selected. The classification reasonability scale will be described later.

The measures acquiring function 213 determines the method for calculating the classification measure vector, and then calculates the classification measure vector $X_i$ according to the determined method.

The extracting function 22 classifies each pattern based on the classification measure vector acquired in step TS5 (step ST6). The simplest pattern classification method is classification by threshold value.

FIG. 7 is a diagram showing a pattern setting table. FIG. 7 shows pattern classification based on a threshold value.

FIG. 7 is a figure which shows an example of a pattern candidate classified by a threshold value as a table. In the table shown in FIG. 7, each of h=1, 2, ... corresponds to one pattern. In the table shown in FIG. 7, multiple pattern numbers h=1, 2, ..., 9, 10, ... are represented. In reality, many patterns are represented, but the table shows only some of them. For convenience of explanation, the types h1 to h9 in the normal distribution model are referred to as "patterns" in the embodiment.

The pattern classification criteria in the table are expressed as discriminant inequalities. The table is composed of the threshold value regarding which element of the pattern classification scale, the direction of the inequality sign, and the threshold value. In the table, the element xs1 of k=1, which is a classification scale showing the complexity of edges and shapes, is applied to the classification of the first pattern. It is determined to belong to this pattern when the complexity is low. Therefore, "smooth-marginating" is set as the pattern name.

Various discriminant analysis methods can be applied to determine the factors used for the prediction, the orientation of the inequality sign, and the threshold value. Using these methods, the discriminant can be determined from the classification measure vector of each group.

One of the specific methods for determining the threshold value is to select the threshold value having the "maximum specificity" among the threshold values satisfying the condition of "PPV<constant" and the direction of the inequality sign at that time. PPV is a positive predictive value, which is the proportion of the mass group whose teacher data is "tumor" among the ROIs predicted by this pattern. It is also possible to determine the threshold based on the confidence interval (described later) of the predicted positive rate instead of PPV. This is a case where it is assumed that the selected pattern is predicted to be positive, but it can be considered that the selected pattern is negative. The PPV calculated at this time will be 1-NPV (negative predictive value) instead of PPV.

Classification by threshold can be expressed not only by inequalities but also by pattern weighting functions. The equation described in the lower part of the pattern classification criteria column of the table is the expression by the pattern weighting function.

The above describes the case of a method of counting the number of regions based on the classification measure vector of all ROIs and the teacher data to determine the threshold value, but the present invention is not limited to this case. As another method, the probability distribution of each group may be represented by, for example, a multidimensional normal distribution based on the pattern classification measure vector of each group. In that case, the distribution function (or probability density function) is acquired by fitting. Similarly, in the case of this method, the orientation of the threshold value and the inequality sign can be determined based on the distribution of each group and the conditions such as PPV and specificity (first modified example to be described later).

In addition, the display criteria of the table have display criteria and a child pattern for each pattern. These details will be described in the next examination stage.

Returning to the description of FIG. 5, the medical data processing apparatus 1 stores the following data (a) to (d) such that they can be used in the next examination stage.

(a) Distribution of classification measure vector

The distribution of the classification measure vectors refers to $N_L$ calculated classification measure vectors, parameters representing the distribution of the classification measure vectors, and lesion probabilities of the ROI. As a method of expressing the distribution data, in addition to the above, there is also a configuration expressed by the number of occurrences of each level (by one or more threshold values of each group), the probability of occurrence of each level of each group, and the histogram of each group. These are equivalent.

(b) Pattern name
(c) Pattern classification criteria
(d) Display criteria (and child pattern)

Proceeding to the description of FIG. 6, the medical data processing apparatus 1 acquires examination image data (e.g., breast MRI image data) to process the presentation of decision reference data for new case (step ST11). Then, the ROI setting function 211 sets the tumor region as the ROI based on the examination image data acquired in step ST11 (step ST12). The feature calculating function 212 calculates the features corresponding to the ROI as a feature vector (step ST13). The calculating of the feature vector in step ST13 is performed by the same method as in step ST4 shown in FIG. 5.

The feature calculating function 212 determines a method for calculating the classification measure vector of the examination image data, and calculates the classification measure vector by the calculation method (step ST14). The determination of the classification measure vector calculation method in step ST14 and the calculation of the classification measure vector are performed by the same method as in step ST5 shown in FIG. 5. When the method of simply selecting two elements of the feature vector is used, only the two elements of the feature vector may be calculated from the beginning, and they may be used as they are as a classification scale.

The measures acquiring function 213 acquires the classification measure vector corresponding to the multiple teacher data set by step ST3 shown in FIG. 5 (step ST15). Alternatively, the parameters of the distribution function determined for each group, such as the mean and standard deviation, are acquired (first modified example to be described later). In addition, the incidence rate (lesion probability of the ROI) of each group in a new case is read. For example, if it is assumed that 70% of the cases to be examined by this method are malignant and 30% are benign, these ratios are read. The rate of 70% is the "lesion probability of the ROI", which is generally different from the incidence of each group in the teacher data set. Lesion probability in the ROI refers to as prevalence sometime.

The extracting function 22 classifies each pattern from the classification measure vector acquired in step ST15 (step ST16). The extracting function 22 calculates group scale data, which is a value that serves as a measure of which group the pattern belongs to, based on the distribution (mean/standard deviation/probability of occurrence, or classification measure vector of the entire teacher data set) of the classification measure vector acquired for each group (step ST17). Group scale data is calculated for each pattern. Since the numerical definition of the pattern is specified in the "pattern classification criteria", the group scale data is calculated according to the "pattern classification criteria" shown in the table of FIG. 7.

The "pattern classification criterion" is more commonly expressed as a "pattern weighting function". In the example shown in the table of FIG. 7, "xs1≤T1h" is represented by the function u (T1h−xs1). u (x) is a step function as shown in the following equation (2).

$$\begin{cases} u(x) = 0 & x < 0 \\ u(x) = 1 & x \geq 0 \end{cases} \quad (2)$$

As the pattern weight function, a function on the bell can be used. When the classification measure vector $X_s$ of the new case is close to the typical point $\mu_h$ of the pattern h, the value is close to "1", and the farther away, the value is closer to "0".

$$w_h(X_s)=\exp(-\tfrac{1}{2}(X_s-\mu_h)^T R_h^{-1}(X_s-\alpha_h)) \quad (3)$$

$w_h(X_s)$ is a function for determining whether or not the classification measure vector $X_s$ belongs to the pattern h.

In another configuration of the weighting function (first variant described below), the following function is used such that it is determined whether any vector X belongs to the pattern h when the typical point $\mu_h$ is equal to the classification measure vector $X_s$ of the new case ($\mu_h=X_s$).

$$W_h(X,X_S)=\exp(-\tfrac{1}{2}(X-X_s)^T R_h^{-1}(X-X_s)) \quad (4)$$

At this time, the pattern classification criteria of the pattern h is a notation "on the bell, k=1, 2". According to this notation, the element of $R_h^{-1}$ can be replaced with "0" except for the two elements of k=1 and k=2 (first modified example to be described later).

In this way, it is possible to refer to the classification measure vector of the new case for the calculation of the group scale data. Similarly, the prediction based on the threshold value can be configured such that the threshold value changes depending on the prediction.

Subsequently, specific examples (A) to (G) for calculating the group scale data will be described. In addition, "$N_{pb}$" is the number of benign regions among the regions included in the pattern. "$N_{pm}$" is the number of malignant regions among the regions included in the pattern, $N_{pb}=N_b-N_{pb}$ and $N_{nm}=N_m-N_{pm}$. Here, $N_b$ is the number of regions in the benign group, and $N_m$ is the number of regions in the malignant group. $P_m$ is the lesion probability of the ROI, $P_b=1-P_m$.

(A) Accuracy=$(N_{pm}+N_{nm})/(N_b+N_m)$ (B) Positive rate (expected value) in the benign group $P_{pb}=N_{pb}(N_{pb}+N_{nb})$—(1-specificity)

(C) Confidence intervals for positive rates in the benign group (lower and upper limits)—omitted (D) Positive rate in malignant group (expected value) $P_{pm}=N_{pm}/(N_{pm}+N_{nm})$—(Sensitivity)

(E) Confidence interval of positive rate in malignant group (lower limit and upper limit)—omitted (F) Predicted positive rate (expected value)=$N_{pm}/(N_{pb}+N_{pm})$—(Positive predictive value PPV); or
Predicted positive rate (expected value)=$P_{pm}\times Pm (P_{pb}\times P_b+P_{pm}\times P_m)$ (G) Confidence interval for predicted positive rate (lower and upper limits)—omitted When the density functions $P_{pb}(X)$ and $P_{pm}(X)$ determined for each group and the lesion probability $P_b$ are acquired (first modified example to be described later), $P_{pb}$ and $P_{pm}$ are acquired by weighted integration. The number of regions per group is not acquired.

$$P_{pb}=\int_{X\subset\Omega_b}w_h(X,X_s)P_{pb}(X)dX, P_{pm}=\int_{x\subset\Omega_b}w_h(X,X_s)P_{pm}(X)dX \quad (5)$$

The benign/malignant prior probabilities $P_b$, $P_m=1-P_b$, the data probability distributions $P_{pb}(X)$, $P_{pm}(X)$, and the measurement noise probability distribution $A_{wh}(X, X_s)$ are given (A: Coefficient for setting the integral to "1"). Data $X_s$ is measured. The predicted positive rate is the posterior probability of the probability that the data is acquired by the malignant region by Bayes' theorem.

Various methods have been proposed to calculate the confidence intervals for the positive rate in the benign group, the positive rate in the malignant group, and the predicted positive rate. For example, a method based on the binomial distribution is known to be accurate, and it is desirable to adopt it.

In addition to the above (A) to (G), various measure values such as odds ratio can be considered, and these expected values and confidence intervals are calculated as group scale data.

Returning to the description of FIG. 6, the extracting function 22 calculates the classification reasonability scale (step ST18). The extracting function 22 calculates the classification reasonability scale using the calculated value of the group scale as a scale showing how reliable it is to predict positive or negative according to the pattern. Expected values or confidence intervals calculated as a group scale, such as accuracy and predicted positive rate, can also be used directly as an classification reasonability scale. However, in the embodiment, the classification reasonability scale is acquired by the following pseudo code from the confidence interval of the predicted positive rate. The "for positive prediction", "PPV design lower limit value at the time of positive prediction", and "confidence interval upper limit value of predicted positive rate" in the pseudo code are the contents of the "designed goal" in the table shown in FIG. 7.

FIG. 8 is a diagram showing an example of pseudo code.

The first and second lines of the pseudo code shown in FIG. 8 are the amount of the confidence interval protruding from the design range. When the third line is satisfied, it is appropriate to predict is as positive, and in this case, the value in the first line is used as an classification reasonability scale. However, the positive and negative are reversed so that the larger value has higher reasonability.

The fifth line shows that the confidence interval falls within the design conditions, in which case the lower confidence interval of the sensitivity is used as the classification reasonability scale. If the third line is not satisfied, it is appropriate to predict it as negative, so the value in the second line is inverted positively and negatively and used as an classification reasonability scale. The 10th line shows that the confidence interval falls within the design conditions, in which case the lower bound of the confidence interval for specificity is used as the classification reasonability scale.

Returning to the description of FIG. 6, the extracting function 22 sets a display flag for a part of the extracted patterns (step ST19). The display flag is calculated according to the display criteria shown in the table shown in FIG. 7. The display criteria of the pattern of h=9 is "the classification reasonability scale is larger than that of all the upper patterns (parent patterns)". Only when this condition is satisfied, the display flag of the pattern is set to "true", and when not, the display flag is set to "false". Furthermore, as an additional condition, a condition that the pattern weight function is not "0" is added. Therefore, the display flag is set to "false" for patterns that do not satisfy the pattern classification criteria. Further, if the display criteria is satisfied in other cases, the display flag is set to "true", and if not satisfied, the display flag is set to "false".

In the table shown in FIG. 7, consider the case where the three patterns 1, 4 and 9 satisfy the pattern classification criteria. These are the three candidates for setting the display flag to "true". The upper pattern of the pattern of h=9 includes two of a pattern of h=4 in which "9" is described in the child pattern (parent pattern of pattern 9), and of a pattern of h=1 in which "4" is described in the child pattern (parent pattern of pattern 4).

Figure 9:
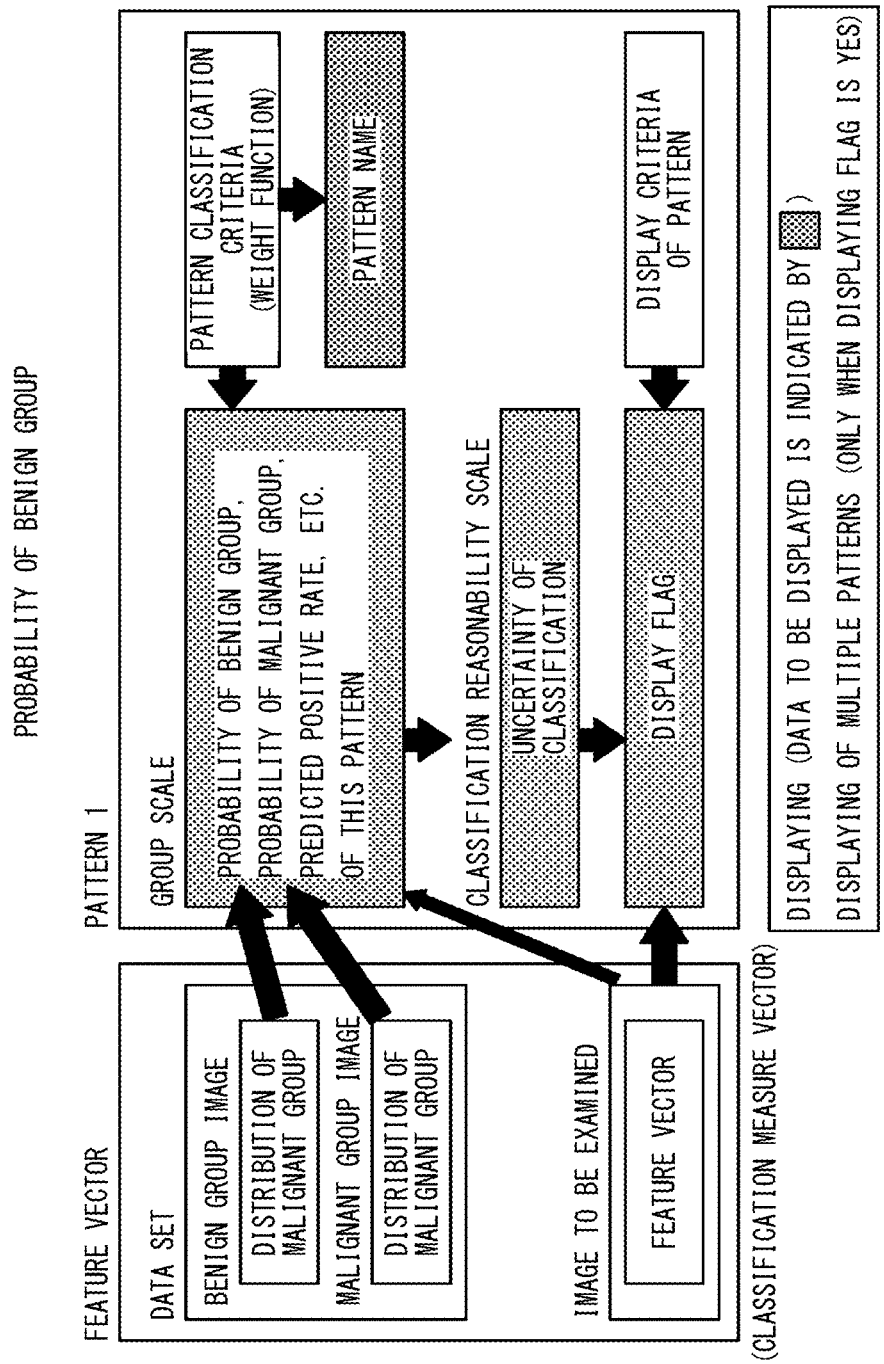
FIG. 9 is a diagram showing a calculation processing of a display flag in the medical data processing apparatus according to the first embodiment.

In the table shown in FIG. 7, the upper limits of these predicted positive rates are displayed as 34.4% (pattern 1), 6.5% (pattern 4), and 16.7% (pattern 9), respectively. The classification reasonability scales are −0.344% (pattern 1), −0.065% (Pattern 4), and −0.167% (pattern 9). Since the classification reasonability scale of pattern 9 is smaller than the classification reasonability scale of pattern 4, it can be seen that pattern 9 does not meet the display criteria. Therefore, the display flag of the pattern 9 is set to "false", so that the pattern 9 is not actually displayed on the screen. Since the pattern 4 satisfies the display criteria, it becomes "true", and since the pattern 1 always has the display criteria of "true", the display flag is "true". The calculation process of the display flag is shown in FIG. 9. In FIG. 9, since the classification reasonability scale of pattern 9 shown in FIG. 7 does not meet the display criteria, the display flag of pattern 9 is set to "false". On the other hand, since the classification reasonability scale of pattern 4 satisfies the display criteria, the display flag of pattern 4 is set to "true".

The medical data processing apparatus 1 displays the pattern names and the calculated values of the group scale for some of the extracted patterns on the display 14 according to the table shown in FIG. 7 (step ST20).

Figure 10:
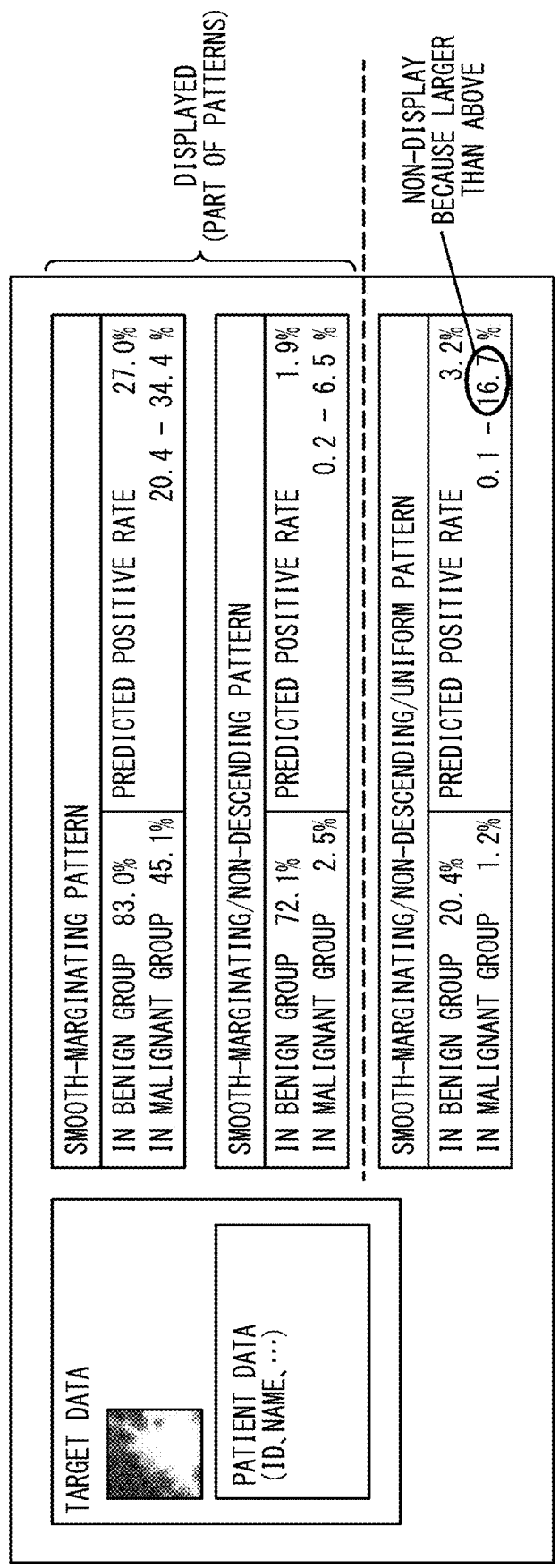
FIG. 10 is a diagram showing a display example of a part of the extracted patterns in the medical data processing apparatus according to the first embodiment.

FIG. 10 is a diagram showing a display example of a part of the extracted pattern.

As shown in FIG. 10, the first "smooth-marginating pattern" is displayed as character data based on the pattern name of the first pattern in the table shown in FIG. 7. The numerical values displayed in each pattern are the calculated values of the group scale. The value of "in the benign group" is the calculated value of the positive rate (expected value) in the benign group, and the value of "in the malignant group" is the calculated value of the positive rate in the malignant group (expected value). In addition, the expected value of the predicted positive rate (or predicted malignancy rate) and the width of the confidence interval are also displayed as the classification reasonability scale.

Only patterns whose display flag is "true" are displayed. Therefore, the third pattern (pattern 9) in FIG. 10 is not actually displayed. The extracting function 22 prescribes a specific pattern to be displayed as criteria regardless of the priority, so that the output function 23 preferentially displays a part of the extracted patterns on the display 14. The output function 23 displays a specific pattern regardless of the priority on the display 14.

In this way, according to the medical data processing apparatus 1, it is determined whether or not to display each pattern according to the value of the classification reasonability scale. As a result, since only a part of the patterns are displayed, it is possible to present the operator with appropriate data for performing an efficient diagnosis.

The learning data group may be classified into the multiple patterns in advance, so the benign probability/malignant probability of each pattern (e.g., it may have a distribution of "benign=2 to 50%") is calculated in advance. In this case, when the multiple patterns corresponding to the image data of the subject are set, the output function 23 is able to preferentially display a part of the multiple patterns that easily identify malignant or benign on the display 14.

According to the medical data processing apparatus 1, it is possible display data from a viewpoint different from the target as the multiple patterns acquired based on the image data, and display, as reference data for the pattern, character data (specifically, the name of the pattern) indicating the pattern. On the other hand, according to the medical data processing apparatus 1, it is desired to comprehensively display the multiple patterns, but on the other hand, it is possible to prevent the presented patterns from becoming excessive.

According to the medical data processing apparatus 1, in particular, by displaying a name representing a feature of an image as reference data for each pattern candidate, it is possible to provide useful data for interpreting an image of breast cancer MRI and describing a report of the result. At that time, if the displayed pattern is insufficient, the data necessary for correct diagnosis cannot be presented, and if it is excessive, efficient diagnosis is hindered. However, according to the medical data processing apparatus 1, it is possible to realize the presentation of the minimum necessary pattern.

First Modified Example

At the design stage shown in FIG. 5, the probability distribution of the pattern classification vector of each group is represented by a multidimensional normal distribution, and the probability density function is acquired by fitting. These values are stored as distribution data for the classification measure vector. As a result of fitting, the average value and standard deviation of each group are acquired.

FIG. 11 is a diagram showing an example of a pattern setting table. FIG. 11 shows pattern classification by approximating the distribution of the classification measure vector by the normal distribution model.

The pattern weight function is calculated by the above-mentioned formula of $w_h(X, X_s)$. Among the elements of $R_h^{-1}$, the value is set to "0" for the elements not described in the "pattern weight function" in the table. For example, the pattern weighting function of pattern 6 in the table shown in FIG. 11 describes three elements of xs1, xs2, and xs3. This indicates that the weight function for the normal distribution for these three elements of the classification measure vector is used, and the elements of $R_h^{-1}$ other than these three elements are replaced with "0".

In the examination stage shown in FIG. 6, the stored average value and standard deviation are acquired as the distribution of the classification measure vector, and the pattern weight function is calculated in the same manner as in the design stage. The positive rate (expected value) $P_{pb}$ in the benign group and the positive rate (expected value) $P_{pm}$ in the malignant group are calculated by the above equation (5).

The predicted positive rate (expected value) is calculated from $P_{pb}$ and $P_{pm}$ as described above. The confidence interval is also calculated as described above.

According to the first modified example of the medical data processing apparatus 1, only a part of the patterns are displayed as a result of determining whether to display each pattern according to the value of the classification reasonability scale. Therefore, similarly, it is possible to present appropriate data for performing an efficient diagnosis to the operator.

Second Modified Example

The above-mentioned FIG. 3 shows a configuration for determining the parameters of the conversion from the feature vector to the classification measure vector. When determining the model parameters for the conversion to the classification measure vector, the step of finding the classification grade in the teacher data can also be simplified. $X_i$ is calculated from the following equation (6) for each ROI i, and $P_{pb}$ is calculated from the following equation (7) for each pattern h.

$$X_i = F_x(f_i; \text{model parameters}) \tag{6}$$

$$P_{pb} = \int_{X \subset \Omega_b} w_h(X, X_s) P_{pb}(X) dX, P_{pm} = \int_{X \subset \Omega_b} w_h(X, X_s) P_{pm}(X) dX \tag{7}$$

Here, the classification reasonability scale of the pattern h is calculated from $P_pb$ and $P_{pm}$ by a pseudo code (shown in FIG. 8). The maximum classification reasonability scale of the ROI i is the maximum value of the classification reasonability scale (h=1, 2, ... ). The classification result is the lower limit of the confidence interval of the maximum classification reasonability scale (i=1, 2, ... ).

To determine the conversion parameters, the above steps are iteratively performed to determine the model parameters that maximize the discriminant performance. A known optimization technique is used to maximize the discrimination results. Regression analysis using artificial neural networks and random forests, and model estimation by linear algorithms are also applicable.

Such conversion parameters are applied to the treatment in new cases.

According to the second modified example of the medical data processing apparatus 1, only a part of the patterns are displayed as a result of determining whether to display each pattern according to the value of the classification reasonability scale. Similarly, it is possible to present appropriate data for making an efficient diagnosis to the operator.

Second Embodiment

The medical data processing apparatus 1A according to the second embodiment calculates a confidence interval of the probability of data on the lesion from the features of the image about the subject, thereby determining the lesion or the probability classification related to the lesion on the basis of the lesion. Further, the medical data processing apparatus 1A is able to select the counting range of the number of cases (or the number of examinations) according to the confidence interval, if necessary.

As a first comparative example, there is a technique for calculating a features of an image in a lesion region of a CT image or an MRI image of a subject, thereby predicting lesion-presence/lesion-absence, benign/malignant, etc. by determining the features with a threshold value. In multi-case clinical studies for the evaluation of such techniques, the positive predictive value (PPV), the negative predictive value (NPV), and their confidence intervals may be used for the evaluation.

In the first comparative example, when it is predicted to be positive, the positive predictive value can be regarded as the lesion probability or the malignant probability. Then, in the case of being predicted to be negative, the negative predictive value can be regarded as the probability of no lesion or the benign probability. However, it does not represent the probability that there is no lesion when it is predicted to be positive or the probability that there is a lesion when it is predicted to be negative. In order to obtain reliable results, it is necessary to reduce the confidence interval of the positive predictive value and the negative predictive value. For that purpose, it is necessary to evaluate using a sufficiently large number of cases. Further, when the feature of the image relating to the subject is close to the threshold value, or when the position is far from the threshold and biased from the majority of examinations, the feature is located at a biased position in the counting range for counting the number of cases. Therefore, the positive predictive value and the negative predictive value evaluated by the determination based on the threshold value have a large asymmetry in the counting range with respect to the feature relating to the subject. The positive predictive value or negative predictive value can be a value that is significantly different from the actual positive or negative probability of the subject. Similarly, the positive predictive value and the confidence interval for the negative predictive value may differ from the actual probability range of the subject.

The confidence interval of the positive predictive value (PPV) and the confidence interval of the negative predictive value (NPV) represent the average performance and width when a large number of examinations are performed. They do not directly represent the nature of the new examination. The actual performance value of the new examination is different from the value at the positive predictive value and the negative predictive value. This difference is particularly large when the value of the feature of the image with respect to the subject is near the threshold value. Even if both the positive predictive value confidence interval and the negative predictive value confidence interval are displayed, only one of the values should be referred to. The new examination is a positive examination, but when you want to see the negative probability of negative, none of them show the actual correct answer rate. Hereinafter, for convenience of explanation, terms such as lesion, lesion probability, malignant, malignant probability, lesion-presence/lesion-absence, no-lesion probability, and their confidence intervals will be used. This is an explanatory word. As shown herein and in the drawings, these are representative of prediction of "lesion-presence/lesion-absence", "lesion type", "good/poor prognosis" and "with/without therapeutic suitability", and their probabilities or their confidence intervals.

There is a technique called the simple Bayes method for acquiring a histogram of a benign group and a histogram of a malignant group on the basis of the value of the feature of images related to a large number of cases used in the study, and acquiring the malignant probability by "malignant probability=malignant frequency/(benign frequency+malignant frequency)" on the basis of the benign frequency and the malignant frequency in the value of the feature of the image relating to the subject, as the second comparative example.

In the second comparative example, the malignant probability and the positive probability can be acquired, but there is a problem that the confidence interval cannot be calculated. Therefore, large-scale clinical studies with a sufficiently large number of cases are required to acquire reliable results.

Examples using various amounts by statistical analysis, for example, confidence intervals of standard deviations and average values of image features are widely used in clinical research as the third comparative example. Further, as the fourth comparative example, there is software that displays the percentile of the hippocampal volume measured in the image of the subject (percentile rank) of the hippocampal volume in the normal case group. There is also software that displays the 5th percentile value and the 95th percentile value of the volume and predicts whether the hippocampal volume of the subject is included in this period.

In the third comparative example, the confidence interval of the statistic represents the characteristics of the distribution in a group consisting of multiple cases, and does not indicate the reliability of the examination data (1 case) of one subject. Therefore, it cannot be used as a numerical value indicating the credibility of the analysis result of one examination data. In the fourth comparative example, the percentile display is a measure of whether the hippocampal volume of the subject is in the normal range. It does not represent the probability of being normal, nor is it its confidence interval. It cannot be used as an indicator of the credibility of a normal or abnormal prediction.

Therefore, the medical data processing apparatus 1A according to the second embodiment calculates the confidence interval of the probability of the data regarding the lesion from the feature of the image relating to the subject, determines the lesion or the probability classification associated with the lesion based on it, and selects the counting range of the number of cases according to the confidence interval of the probability.

Since the configuration of the medical data processing apparatus 1A according to the second embodiment is the same as the configuration of the medical data processing apparatus 1 according to the first embodiment shown in FIG. 1, the description thereof will be omitted.

Figure 12:
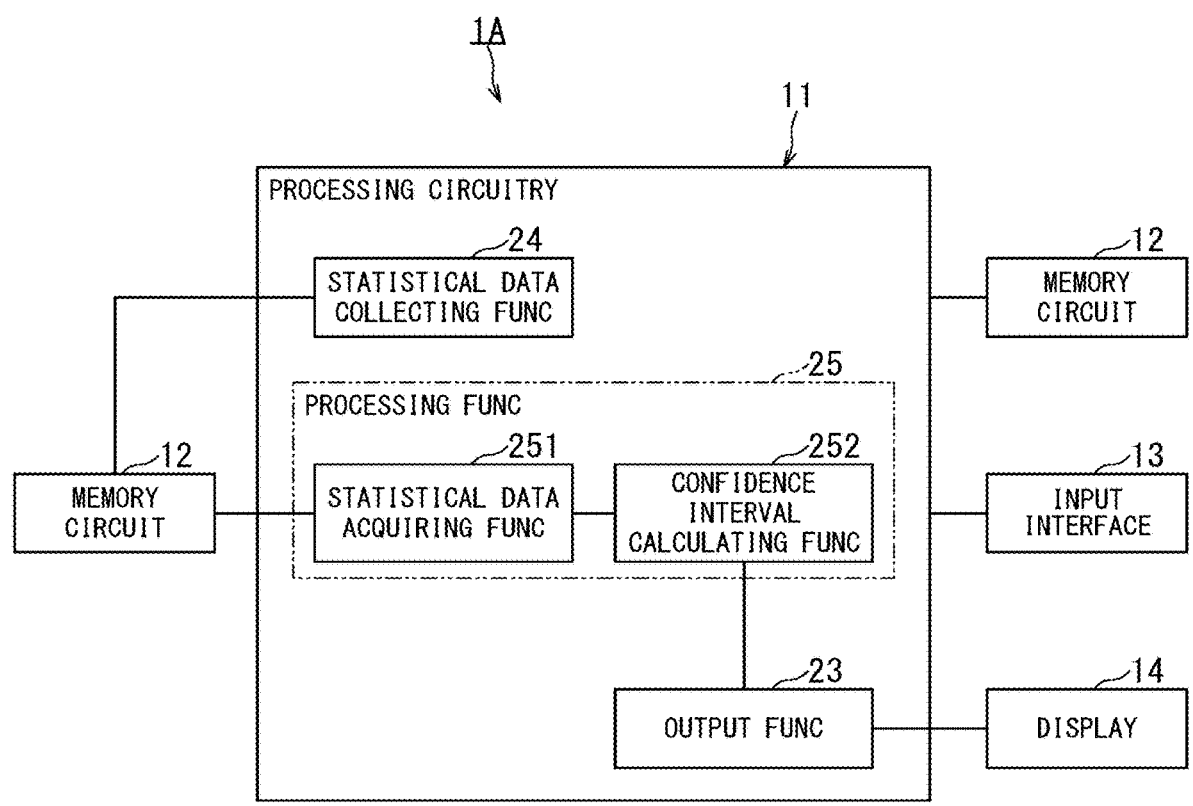
FIG. 12 is a block diagram showing functions of the medical data processing apparatus according to the second embodiment.

FIG. 12 is a block diagram showing functions of the medical data processing apparatus LA.

When the processing circuitry 11 executes a computer program stored in a non-transient recording medium such as the memory circuit 12, the medical data processing apparatus 1 realizes an output function 23, a statistical data collecting function 24, and a processing function 25. All or part of the functions 23 to 25 may be realized as a circuit such as an ASIC in the medical data processing apparatus 1.

The statistical data collecting function 24 has a function of collecting statistical data regarding the frequency of lesions based on the characteristics of a plurality of image data, and a function of storing the collected statistical data in the memory circuit 12. The statistical data collecting function 24 is an example of a statistical data collecting unit.

The processing function 25 has a function of calculating the probability that the image data of the subject is acquired from "lesion-presence" subjects and the confidence interval which is a measure indicating the reliability of the probability. Specifically, the processing function 25 has a statistical data acquiring function 251 and a confidence interval calculating function 252. The processing function 25 is an example of a processing unit.

The statistical data acquiring function 251 has a function of acquiring statistical data regarding the frequency of lesions aggregated based on the characteristics of multiple image data collected by the statistical data collecting function 24 from the memory circuit 12. Alternatively, the statistical data acquiring function 251 acquires multiple image data or image feature values from the memory circuit 12 and calculates statistical data. The statistical data acquiring function 251 is an example of a statistical data acquiring unit.

The confidence interval calculating function 252 has a function of calculating the probability that the image data of the subject is acquired from "lesion-presence" subjects, and a confidence interval that is an indicator of the reliability of the probability on the basis of an arbitrary range including the measured value of the subject, using the frequency distribution shown in the statistical data. The confidence interval calculating function 252 is an example of a confidence interval calculating unit.

The output function 23 includes a function of outputting data on the lesion based on the probability by the processing function 25 and the confidence interval of the probability. For example, the output function 23 outputs the probability and the confidence interval of the probability as data on the lesion as described later using the first function f1 to the first-G function f1G (e.g., it is displayed on the display 14). Further, the output function 23 outputs, as the data regarding the lesion, the predicted result regarding the lesion of the subject based on the relationship between the probability and the confidence interval of the probability, or regarding the probability classification (probability category) of the lesion, as will be described later using the second function f2 to the second-G function f2G (e.g., it is displayed on the display 14).

The specific operations of the functions 23 to 26 will be described later with reference to FIGS. 13 to 44.

(First Function and Second Function)

Figure 13:
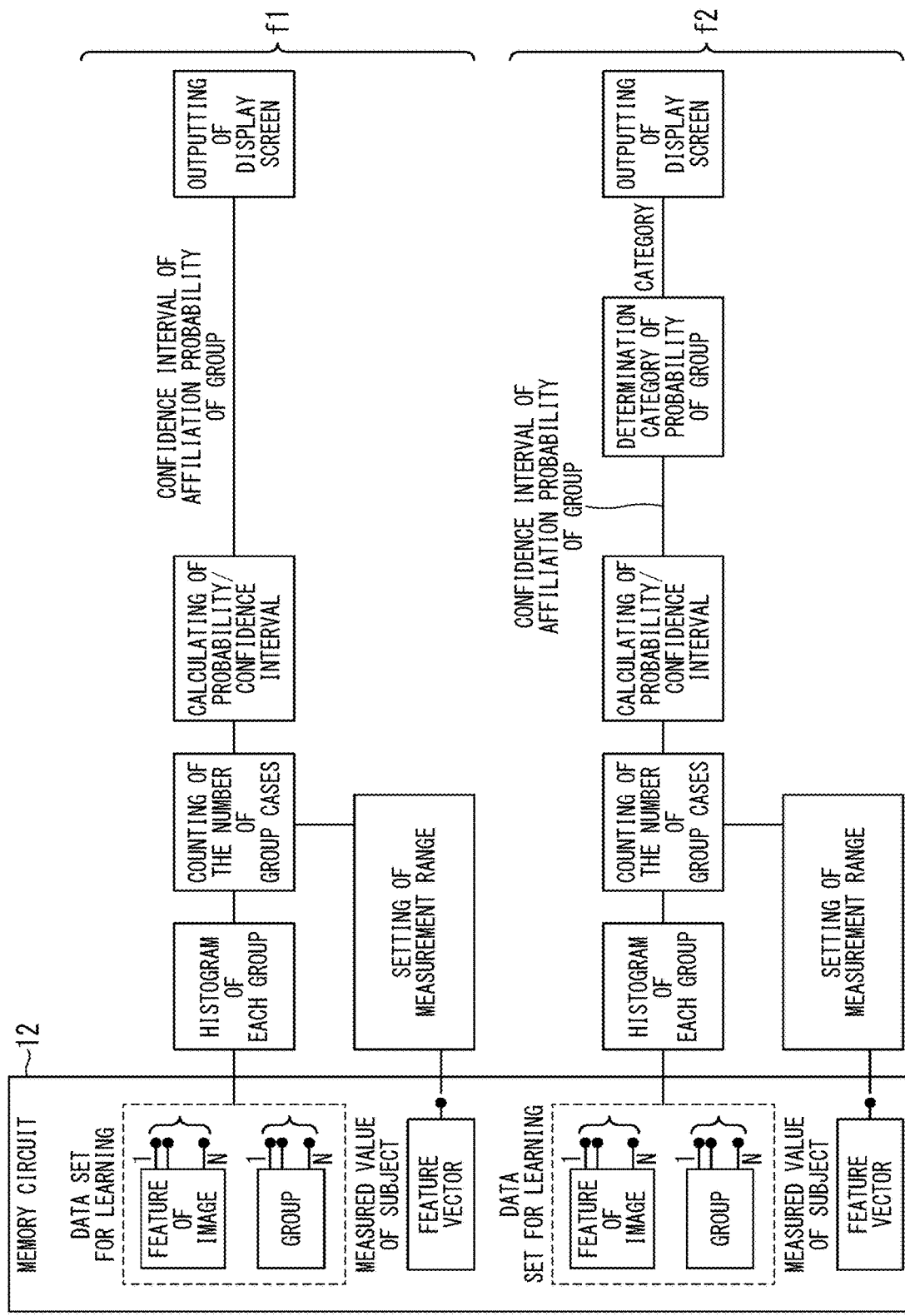
FIG. 13 is a data flow diagram showing a first function and a second function in the medical data processing apparatus according to the second embodiment.

FIG. 13 shows the first function f1 including a function of calculating a confidence interval of a probability such as a lesion probability by the processing function 25 and a function of outputting a confidence interval by the output function 23. For example, the confidence interval output function displays a display screen showing the confidence interval on the display 14. Further, FIG. 13 shows the first function f1 and the second function f2. The second function f2 includes a predicting function of a lesion probability classification etc. based on the confidence interval of the probability by the processing function 25, and an output function of the predicted result by the output function 23. For example, the predicted result output function displays a display screen showing the predicted result on the display 14. FIG. 13 is a diagram showing the first and second functions f1 and f2 of the medical data processing apparatus 1A as a data flow.

The first function f1 of FIG. 13 will be described first. The confidence interval calculating function 252 plots the value (measured value) of the feature of the image relating to the subject on the statistical data (e.g., the frequency distribution (histogram)), the statistical data relating to the frequency of the lesion aggregated based on the characteristics of the image data of the N examinations used in the analysis. Then, the confidence interval calculating function 252 sets a width around the measured value, counts the number of cases, and acquires a confidence interval. The number of cases in a group means the number of cases in each group of multiple image data (examinations included in the counting range). In the first comparative example described above, the positive predictive value and its confidence interval are acquired only in one of the two areas. The positive predictive value is the average positive rate of examinations that are predicted to be positive. The negative predictive value is the average negative rate of examinations that are predicted to be negative. On the other hand, in the above-mentioned second comparative example, the confidence interval cannot be acquired.

On the other hand, the first function f1 is to acquire the confidence interval in the counting range according to the measured value with respect to the subject, as shown by the arrow in FIG. 14A. FIG. 14A shows the measured values for the subject arranged in the statistical data (e.g., frequency distribution (histogram)). Since the confidence interval of the lesion probability represents the range of variation in the probability that the subject is acquired from "lesion-presence" subjects, it can be used to show the credibility of the predicted result of whether or not the subject is acquired from "lesion-presence" subjects. Further, the confidence interval calculating function 252 acquires the confidence interval within an appropriate counting range according to the measured value of the subject. Therefore, the confidence interval calculating function 252 can indicate the probability for the measured value for a specific subject, not the average probability. Therefore, even in a small study, the confidence interval can be narrowed depending on the measured values of the subject without using clinical data of a large number of cases. It has the effect of acquiring reliable and useful results.

For example, images of N examinations used for analysis and values of a group corresponding to each examination are prepared in advance. There are two groups, a "no lesion" group and a "lesion" group. As shown in FIG. 15, a graph U15 is shown in which a histogram based on the feature of the data of "no lesion" and a histogram composed of the feature of the data of "lesion-presence" out of N tests are superimposed. The measured values (shown in graph B15) for the subject are plotted against the graph U15 of this histogram. The result of calculating the number of cases of "no lesion" per fixed width around the measured value is shown by the point "a" in the graph M15. Similarly, the result of calculating the number of cases with "lesion-presence" per fixed width is indicated by the point "b". The confidence interval calculating function 252 calculates the lesion probability by "b/(a+b)", and calculates the confidence interval (upper limit value and lower limit value) of the lesion probability by the following equations (8) and (9).

$$P_{lower} = I_\alpha^{inv}(b, a+1) \quad (8)$$

$$P_{upper} = I_{1-\alpha}^{inv}(b+1, a) \quad (9)$$

$I_\alpha^{inv}(a,b)$ is the inverse of the incomplete beta function $I_\alpha(a,b)$. There are several methods for calculating the confidence interval of the probability of belonging to a group (hereinafter referred to as "probability of belonging to a group"). For example, the confidence interval calculating function 252 can also calculate the lesion probability (upper limit value and lower limit value) by the following equations (10) and (11). In addition, "$\alpha$" is a significance level, and "0.025" is typically used as "$\alpha$".

$$P_{lower} = I_\alpha^{inv}(b+1, a+1) \quad (10)$$

$$P_{upper} = I_{1-\alpha}^{inv}(b+1, a+1) \quad (11)$$

Furthermore, it may be suggested that there is a large variation in the lesion probability acquired with a wide confidence interval depending on the measured values for the subject. According to the first function f1, the output function 23 is possible to present this to the operator, so that the operator determines not to use the unreliable predicted result.

The confidence interval calculating function 252 may be configured to optimize the counting range to an appropriate width according to each value of the feature. As a result, the confidence interval may be narrowed because the optimum counting range according to the measured value for the subject is used. Therefore, the possibility of acquiring reliable results increases.

Further, the confidence interval calculating function 252 may be configured to select an appropriate width by using the value of the confidence interval as shown by the multiple arrows in FIG. 14B. In that case, first, the confidence interval calculating function 252 determines a narrow confidence interval among a large number of confidence intervals corresponding to a large number of counting ranges. Then, the confidence interval calculating function 252 displays the malignant probability and the confidence interval, and predicts benign/malignant/unknown. As a result, the counting range can be set to an appropriate width according to the measured value instead of being fixed. Regardless of the measured value, it is possible to make a prediction while suppressing appropriate variation according to the measured value. The counting range is a range having a certain width centered on the counting value, and the width is determined so that, for example, the lower limit of the confidence interval is the largest. In this case, the output function 23 can output a predicted result according to the average value of the lesion probability, the confidence interval (upper limit value and lower limit value) of the lesion probability, or the prediction condition of the confidence interval.

The second function f2 of FIG. 13 will be described. The confidence interval calculating function 252 predicts the probability classification (Hereinafter, referred to as "probability category" or simply "category") based on the upper limit value or the lower limit value of the confidence interval such as the lesion probability calculated by the first function f1, and displays it. For example, the confidence interval calculating function 252 outputs whether the lesion possibility is high, medium, or low. Here, the category means a classification based on the confidence interval of the lesion probability. For example, it is classified into low possibility of lesion, meddle possibility of lesion, high possibility of lesion, and the like.

(First-A Function and Second-A Function)

FIG. 16 shows the first-A function f1A. The first-A function f1A includes a function of calculating a confidence interval of a probability such as a lesion probability by the processing function 25 and a function of outputting a confidence interval by the output function 23. Further, FIG. 16 shows the first-A function f1A and the second-A function f2A. The second-A function f2A includes a predicting function of a lesion probability classification etc. based on a confidence interval of the probability by the processing function 25, and an output function of the predicted result by the output function 23. The first-A function f1A (the same applies to the second-A function f2A) expresses the counting range by a weighting function. FIG. 16 is a diagram showing a data flow related to the first-A and second-A functions f1A and f2A of the medical data processing apparatus LA.

In the above description of the minimum configuration and the following description, it is simply expressed as a counting range. The counting range may be a range surrounded by a single threshold value or multiple threshold values in the feature space, but can be generally represented by a weighting function (counting weighting function). Preferably, a bell-shaped weighting function is used in which the value of the feature of the image relating to the subject becomes "1" and the value approaches "0" as the distance from the value becomes "1".

When the feature (e.g., the feature vector) is represented by x (x=x1, x2, . . . ), the count weight function is represented as follows.

(1) Simple threshold: When the measured value is u (u=u1, u2, . . . ), and in a case of ui−ri<$x_i$<ui+ri, it is "1", or in the other case, it is "0", with respect to the weight function "w" is "1" for all i.

(2) Multidimensional Gaussian function: w=exp (−0.5 (x−u)$^T$ R$^{-1}$ (x−u))

Note that "R" is a positive symmetric matrix.

When the counting weight function is used, the confidence interval calculating function 252 acquires the total number of data in the counting range w (synonymous with "weight function w") and the number of data belonging to the group i in the total number of data. Assuming that the histogram of the data of each group is Hci (x) and the sum of the histograms of all groups is Ha (x), the total number of data in the counting range w (x) can be obtained by the following equation (12). w (x) is the above-mentioned weighting function, preferably a bell-shaped weighting function. Further, the number of data belonging to the group i is obtained by the following equation (13). In addition, "I" shows a group number, and "x" shows a feature vector.

$$N_a = \int w(x) H_a(x) dx \quad (12)$$

$$N_{ci} = \int w(x) H_i(x) dx \quad (13)$$

(First-B Function and Second-B Function)

FIG. 17 shows the first-B function f1B. The first-B function f1B includes a function of calculating a confidence interval of a probability such as a lesion probability by the processing function 25 and a function of outputting a confidence interval by the output function 23. FIG. 17 shows the first-B function f1B and the second-B function f2B. The second-B function f2B includes a predicting function of a lesion probability classification etc. based on a confidence interval of the probability by the processing function 25, and an output function of the predicted result by the output function 23. The first-B function f1B (the same applies to the second-B function f2B) optimizes (maximizes or minimizes) the counting range. FIG. 17 is a diagram showing a data flow related to the first-B and second-B functions f1B and f2B of the medical data processing apparatus LA.

The counting range does not have to always have a constant width and shape in the feature space, and it is preferable to use an appropriate width and shape according to the value of the feature (hereafter, it is stated that an appropriate counting range will be determined). Focus on a group to determine the appropriate counting range. A counting range in which the lower limit of the confidence interval of the probability of belonging to the group is as large as possible is selected from the counting weight functions that are "1" in the measured value for the subject. Alternatively, a counting range in which the upper limit of the confidence interval of the probability of belonging to the group is as small as possible is selected from the counting weight functions that are "1" in the measured value for the subject.

As shown in FIG. 18, the counting range that maximizes the confidence interval lower limit of the probability of "no lesion" is selected. In the case of the counting range of the value LA represented by the curve RA in the graph U18, the number of cases in the "no lesion" group in the counting range is "a" (shown in the graph M18), the number of cases in the "lesion-presence" group is "b" (shown in graph M18), and the upper limit of the confidence interval for the probability of "no lesion" (=1-lesion probability) is maximized. In the graph U18, the curve RB shows the counting range when the measured value (shown in the graph B18) for the subject is another value LB. As described above, the counting range differs depending on the value of the feature. That is, an appropriate counting range is selected according to the measured values for each subject, and a highly reliable predicted result can be acquired as compared with the method using a simple threshold value that is simply selected from two types of ranges. The confidence interval calculating function 252 calculates the lesion probability by "b/(a+b)", and calculates the confidence intervals (upper limit value and lower limit value) of the lesion probability by the above equations (8) and (9) or the above equations (10) and (11).

(First-C Function and Second-C Function)

FIG. 19 shows the first-C function f1C including the function of calculating the confidence interval of a probability such as a lesion probability by the processing function 25 and the function of outputting the confidence interval by the output function 23. FIG. 19 shows the first-C function f1C and the second-C function f2C. The second-C function f2C includes a predicting function of a lesion probability classification etc. based on a confidence interval of the probability by the processing function 25, and an output function of the predicted result by the output function 23. As described in the first-B function f1B described above, when the counting range is optimized for multiple groups, the counting range corresponding to the number of groups can be acquired. In the first-C function f1C and the second-C function f2C, one group is selected by using the upper limit value or the lower limit value of the confidence interval acquired in the counting range of each group. Then, the counting range of that group is applied to other groups to recalculate the confidence interval. FIG. 19 is a diagram showing a data flow related to the first-C and second-C functions f1C and f2C of the medical data processing apparatus 1A.

The confidence interval calculating function 252 predicts, for each group, a counting range that maximizes the lower limit of the confidence interval for that group. This is repeated, and the counting range having the largest confidence interval lower limit and maximum value is selected from the counting ranges of all groups. Then, it is applied to other groups to calculate the lesion probability and confidence interval. In FIG. 19, a case where four types of brain tumors are used as a group as shown in FIGS. 20A to 20D will be described.

As shown in FIGS. 20A-20D, the finest grouping of multiple tests is "glioma Gr1, 2", "glioma Gr3, 4", "PCNSL (central nervous system primary malignant lymphoma)", "brain metastasis", "meningioma", "pituitary adenoma", and "other", but these are grouped and four groups (classes) of "glioma", "PCNSL", "brain metastasis", and "other" are used.

The characteristic part of the confidence interval calculating function 252 is the procedure (3) in the following four schematic procedures (1) to (4).

(1) When one lesion group is taken, determine the counting range that maximizes the lower limit of the confidence interval of that lesion group.

(2) Repeat this and select the counting range with the largest confidence interval lower limit maximum value from the counting range of all groups (classes) as the main class (main group).

(3) Reapply the count of the main class (main group) to the other groups (classes) to acquire the lesion probability of each group (class) and its confidence interval.

(4) Predict the probability category based on the lower limit of the confidence interval of the main class (main group) and the upper limit of the confidence interval of the other group (class).

Figure 20A:
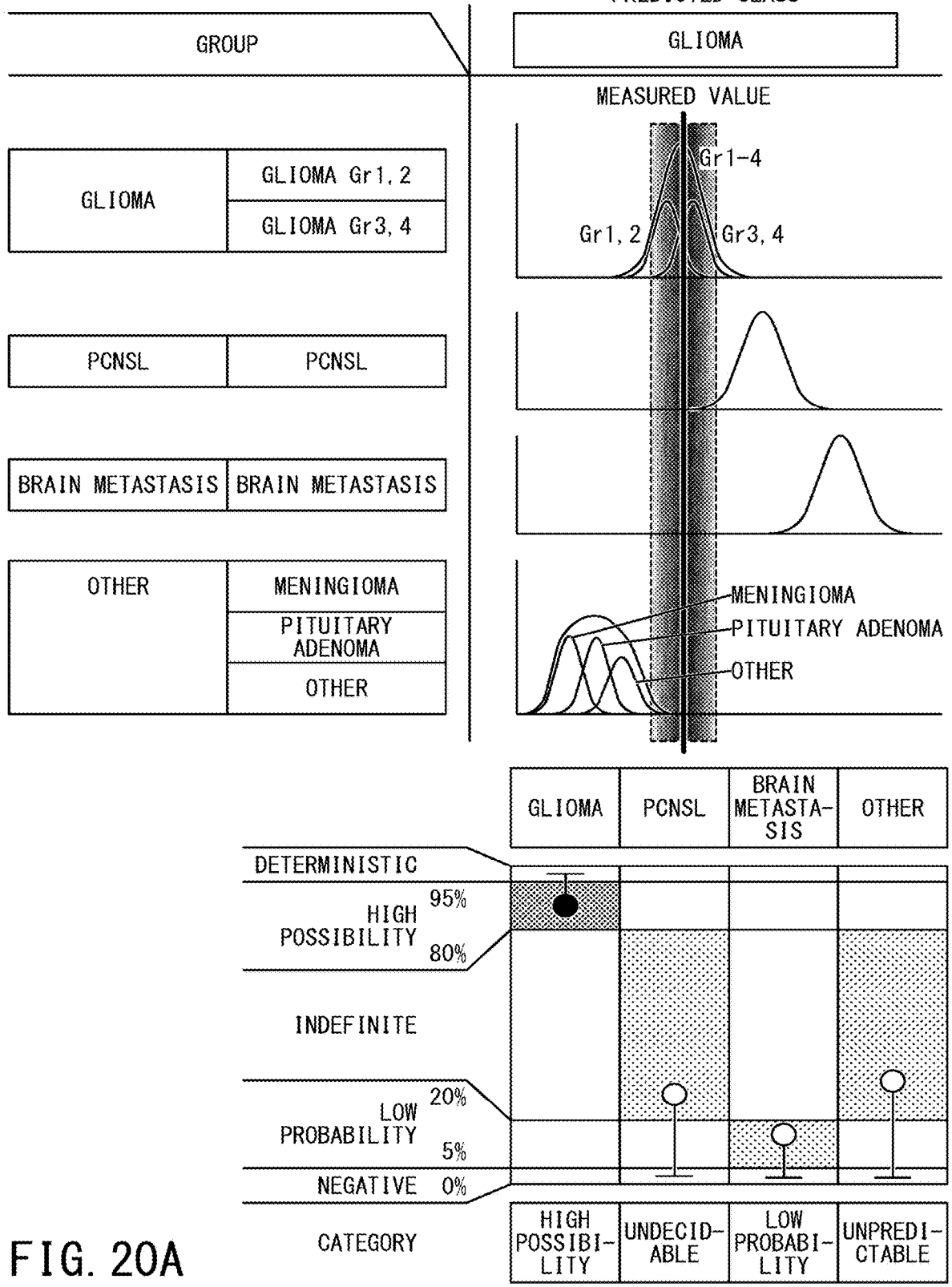
Figure 20B:
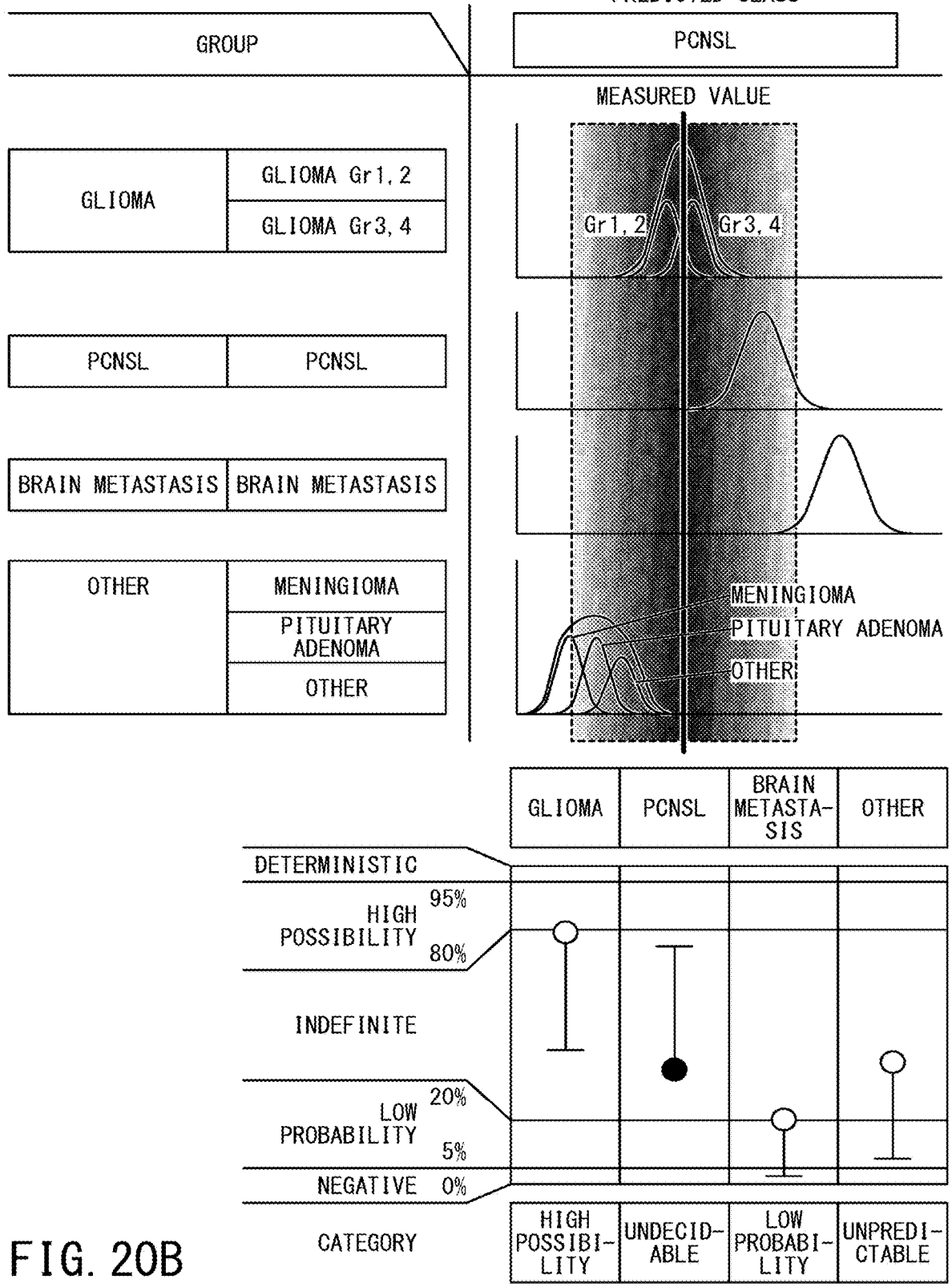
Figure 20C:
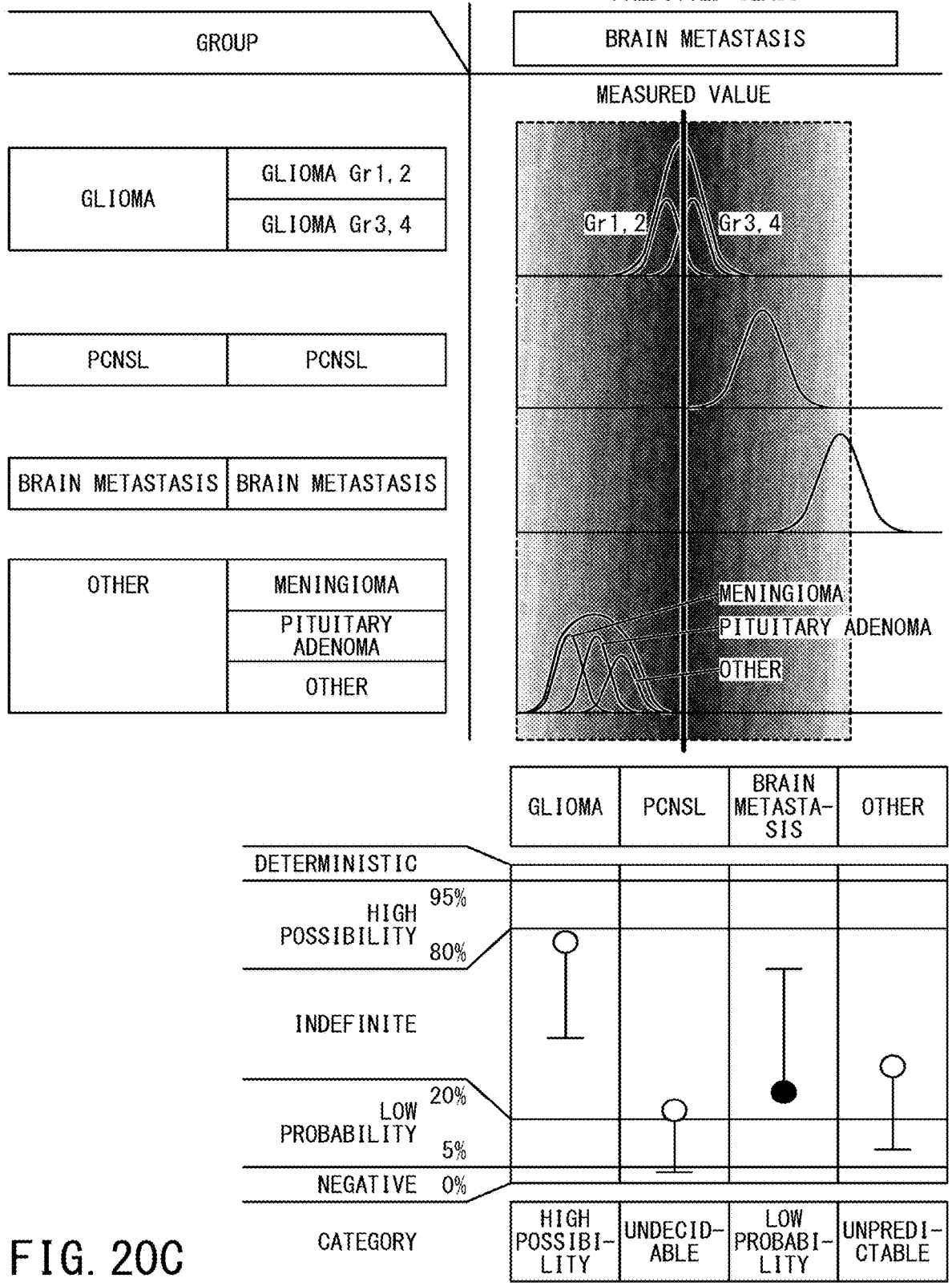
Figure 20D:
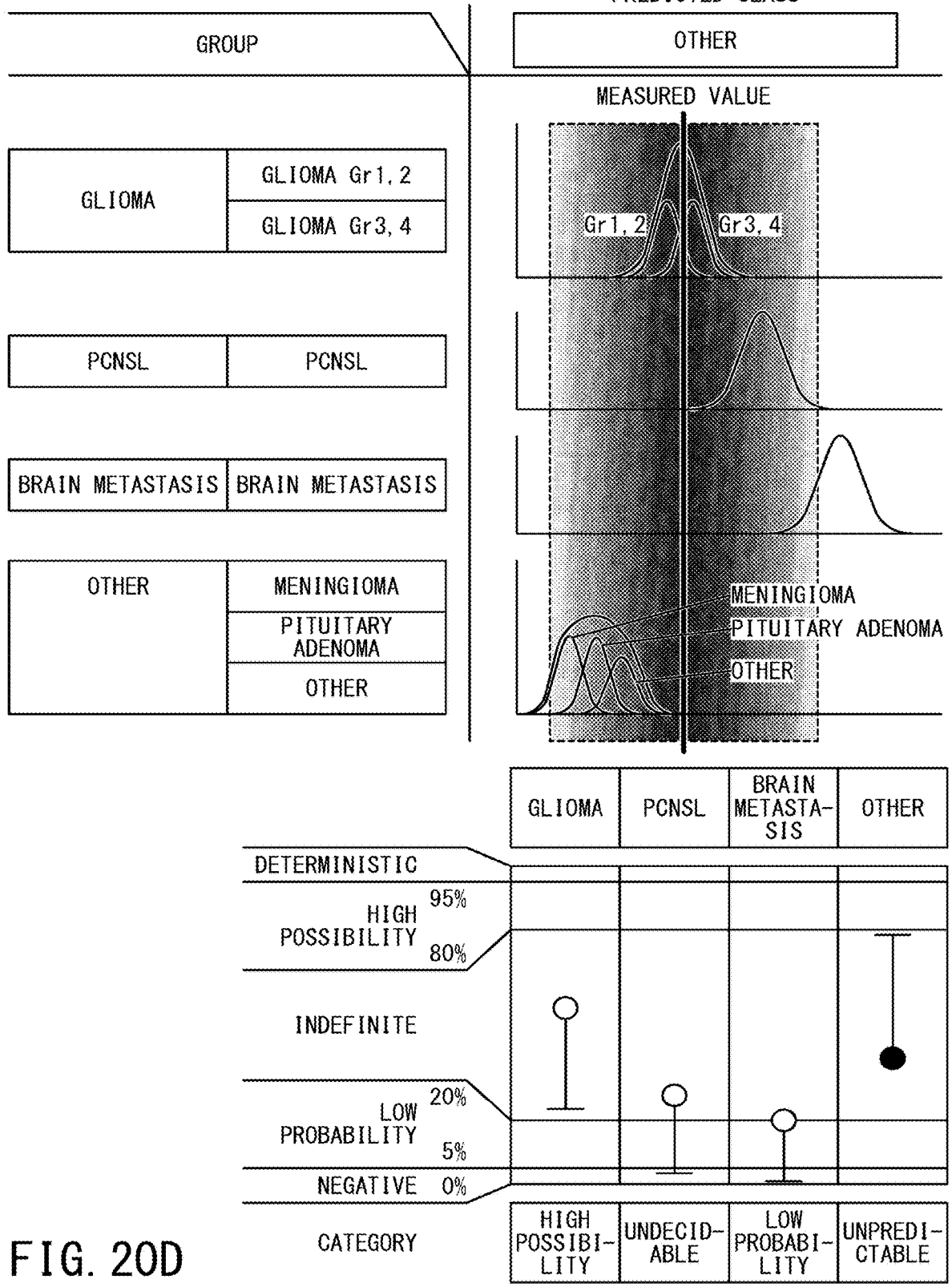

Hereinafter, the processing procedure of the confidence interval calculating function 252 will be specifically described.

i) The research data have been confirmed and include various brain tumors. Histograms of feature values are created for each type of brain tumor. When the four selected major classifications are used as the prediction group, four integrated histograms are generated.

ii) A counting range is set around the measured value of the feature in the subject, and a counting range that maximizes the lower limit of the confidence interval of the probability of "glioma" is acquired (broken line in FIG. 20A). Similarly, the counting ranges that maximize the lower confidence interval of the other groups are determined (broken lines in FIGS. 20B to 20D). Then, the confidence intervals of the probabilities (average) belonging to each group and the probabilities belonging to each group are calculated respectively.

iii) The circle marks indicating the lower limit of the confidence interval of each group shown in FIGS. 20A to 20D are compared, and the counting range of the glioma having the largest value (FIG. 20A) is selected. It is distinguished by making the display form (e.g., the background color) of the position indicating the lower limit of the confidence interval of the glioma different from other positions. This glioma is the main class (main group). The operator can reselect another group as the main class (main group).

iv) Only the main class data acquired from the selected counting range of FIG. 20A is displayed.

v) The probability (mean) and confidence interval belonging to each group in the counting range of the selected main class "glioma" are calculated and displayed.

vi) The lower confidence interval values for the selected glioma and the upper confidence interval values for the other groups are displayed. Which category the value belongs to is predicted and displayed (category "high possibility" shown in FIG. 20A).

FIGS. 21A to 21C are diagrams showing a display example of the predicted result. FIGS. 21A to 21C may be displayed respectively, or may be displayed in parallel on the same display screen. "CBV (Cerebral Blood Volume)" as a feature indicates the cerebral blood volume. "Ktrans" indicates the transition rate constant at which the contrast medium leaks into the EES (Eextracellular Extravascular Space). As shown in FIG. 21B, for example, the "glioma" portion is displayed with a color different from that of other classes such that "Glioma" selected as the main group (main class) is now visible. In addition, the value of the average probability of "glioma" is also displayed. In addition, the average probability value and the like are also displayed for other categories that are subgroups.

Further, as shown in FIG. 21C, an image in which the lesion site is marked (e.g., a DWI (diffusion weighted image) image) or the like can be displayed. "FLAIR (Fluid-Attenuated Inversion Recovery)" is an image in which a water signal is suppressed in MRI. "T1W_CE (T1 Weighted contrast enhanced)" is a T1-weighted image in which contrast is enhanced in MRI. "CBV (Cerebral Blood Volume)" is an image of cerebral blood flow. Further, FIG. 21C shows an image showing a transition rate constant (Ktrans) in which the contrast medium leaks into the EES (Extracellular Extravascular Space), shows an image showing plasma volume (Vp) in a blood vessel, shows an image showing the EES volume (Ve) and an image showing the transition rate constant (Kep) returning to the blood vessel.

In addition, the above-mentioned procedure ii) of the counting range in one group may be performed. In that case, the average value of the probabilities acquired in step ii), the confidence interval, and the category are displayed in step vi) without performing the main group selection and subsequent processes iii) to v). This configuration is not suitable for statistically specialized analysis, such as the sum of the average values of each group of probabilities to be displayed does not become "1". However, since the main group is not selected, the processing of each group is the same, and fair selection is possible. Therefore, the configuration is suitable for analysis software for routine examination.

Further, in addition to the above procedure ii) of the total tumor range within one group, it is also possible to perform the selection between the groups of the counting range iii) to v). After that, the procedure vi) is carried out. In the case of this configuration, in order to perform sufficient analysis, the operator needs to compare with the case where another group is set as the main group, and complicated operations are required to switch the main group. On the other hand, the sum of the average values of each group is "1", which is suitable for statistically rigorous and professional analysis. Therefore, this configuration is suitable for professional analysis software for research.

(First-D Function and Second-D Function)

FIG. 22 shows the second-D function f1D. The second-D function f1D includes a confidence interval of a probability such as a lesion probability by the processing function 25, a graph calculating function by the processing function 25, and an output function of the confidence interval and the graph by the output function 23. FIG. 22 shows the first-D function f1D and the second-D function f2D. The second-D function f2D includes a predicting function of a lesion probability classification etc. based on a confidence interval of the probability by the processing function 25, and an output function of the predicted result by the output function 23. The first-D function f1D (as well as the second-D function f2D) displays a histogram and a counting range. FIG. 22 is a diagram showing a data flow related to the first-D and second-D functions f1D and f2D of the medical data processing apparatus LA.

The output function 23 generates a graph in which the counting range determined according to the measured value for the subject and the measured value for the subject are superimposed on the histogram for each group of the multiple examinations, thereby generating a display screen (e.g., a display screen including the counting range and measured values shown in FIGS. 14A and 14B).

(First-E Function and Second-E Function)

FIG. 23 shows the first-E function f1E. The first-E function f1E includes the category prediction of the group affiliation probability based on the confidence interval of a probability such as a lesion probability by the processing function 25, a calculating function with a category area map, and an output function of the category predicted result by the output function 23 and the category area diagram. FIG. 23 shows the first-E function f1E and the second-E function f2E. The second-E function f2E includes a simultaneous output function of the category predicted result and the category area diagram by the output function 23. The first-E function f1E (the same applies to the second-E function f2E) displays the area map of the category as a graph. FIG. 23 is a diagram showing a data flow related to the first-E and second-E functions f1E and f2E of the medical data processing apparatus LA. The confidence interval calculating function 252 performs a convolution calculation when counting the number of group cases.

As shown in FIG. 24A, a category area diagram showing which category is predicted according to the confidence interval upper limit value and the confidence interval lower limit value of the group affiliation probability of each group is displayed. The group affiliation probability means the probability that a subject having a certain feature value belongs to a certain group. For example, a category area map is displayed using the confidence interval lower limit of the benign probability and the confidence interval lower limit of the malignant probability. Depending on the level for prediction, for example, "99%" and "90%", the area (a) shown in FIGS. 24A and 24B corresponds to "certainly malignant", the area (b) corresponds to "probably malignant", the area (c) corresponds to "unknown (close to malignant)", the area (d) corresponds to "unknown (close to benign)", the area (e) corresponds to "probably benign", and the area (f) corresponds to "certainly benign".

The lower and upper limits of the confidence interval of the subject are plotted in the category area map, and different colors are given to each area of the predicted result and displayed. As a result, it is possible to present in an easy-to-understand manner what the probability is in the data of the subject. In addition, it is possible to show in an easy-to-understand manner how the prediction is made based on the value of the confidence interval or how the prediction is made.

In the graph U25 showing the lesion probability with respect to the width of the threshold range shown in FIG. 25, the maximum value of the lower limit of the confidence interval of the lesion probability is indicated by circle marks. The maximum point is assigned to the vertical axis of the category area diagram R25. On the other hand, in the graph B25 showing the lesion probability with respect to the width of the threshold range, the minimum value of the upper limit of the confidence interval of the lesion probability is indicated by circle marks. Allocate the minimum point to the horizontal axis of the category area map. The average value of the lesion probability, the upper limit value of the confidence interval, and the lower limit value correspond to the "group scale" in the first embodiment. Also, the confidence interval upper and lower limits are used to select and optimize the counting range. In that case, the average value of the lesion probability, the upper limit value of the confidence interval, and the lower limit value correspond to the "classification reasonability scale" of the first embodiment.

The areas indicated by (a) to (f) in the category area diagram R25 are corresponds to 6 categories of "certainly malignant", "probably malignant", "unknown (close to malignant)", "unknown (close to benign)", "probably benign", and "Surely benign" respectively. The category is predicted by where it is plotted on this category area map.

The category area diagram R25 may be predicted for each axis, but is not limited to that case. For example, the category area map may be a category area map including both a diagonal prediction curve and a prediction straight line as shown in FIG. 26A. Further, the category area map may be a category area map including only the prediction straight line as shown in FIG. 26B.

Further, FIG. 27 shows an example in which two groups, "benign" and "malignant", are used as groups. As shown in FIG. 27, category areas according to malignancy and benignness are used. On the other hand, FIG. 28 shows an example in which two groups, "therapeutic effective" and "no therapeutic effect", were used as groups. As shown in FIG. 28, category areas are used depending on whether they are valid or invalid.

(First-F Function and Second-F Function)

FIG. 29 shows the first-F function f1F. The first-F function f1F includes a confidence interval of the lesion probability or the like by the processing function 25, an image display and a calculating function of the area display, an output function of a confidence interval by the output function 23, an image display, and an area display. FIG. 29 shows the second-F function f2F. The second-F function f2F includes the first-F function f1F, the category predicting function of the group affiliation probability by the processing function 25, and the output function of the category predicted result by the output function 23. The first-F function f1F (the same applies to the function f2F of the second floor) displays an image and a feature calculating area. FIG. 29 is a diagram showing a data flow related to the first-F and second-F functions f1F and f2F of the medical data processing apparatus 1A.

The output function 23 displays the image on which the analysis is based and the target area (e.g., the ROI) for which the feature is calculated on the screen. The operator can confirm whether the value of each displayed feature is appropriate in light of the image.

(First-G Function and Second-G Function)

The first-G function f1G by the processing function 25 (the same applies to the second-G function f2G) sets the prevalence of the facility. FIG. 30 is a diagram showing a data flow related to the first-G and second-G functions f1G and f2G of the medical data processing apparatus 1A.

The operator or system administrator can set (change) the probability of occurrence at this facility in each group. In this case, the probabilities of steps ii) and v) and the values of the confidence intervals are corrected using the set probability of occurrence.

In this case, the lesion probability (class prior probability) is often regarded as the same as the ratio of each lesion (class composition ratio) of the cases included in the database used for analysis. The lesion probability indicates what kind of lesion the subject has before performing the examination. This is based on the premise that criteria for registering cases in the database, including race, and criteria for processing whether or not they are subject to examination at the facility can be regarded as the same. However, the lesion probability (prior probability of the group) can vary depending on the characteristics of the facility (whether it is a clinic or a specialized hospital) and what other examinations are done before the target examination. In this case, the calculated lesion probabilities and confidence intervals can be inaccurate by regarding both as the same. In order to absorb the difference between the group ratio in the case database and the probability of occurrence in the institution or the probability of the group depending on the history of the subject, it is necessary to correct the prior probability of the group.

For the calculation of the corrected value of the probability belonging to each group and the confidence interval of a probability, after determining the counting range of the group A, the average of the probabilities of the group A within the counting range and the confidence interval are acquired. Among the cases in the database, the number of cases in group A acquired in the counting range of group A is defined as $n_{p_1}$. The total number of cases in groups other than group A acquired in the counting range of group A is defined as $n_{n_1}$. The total number of cases in group A is defined as $N_p$. The total number of cases in groups other than group A is defined as $N_n$.

Further, the lesion probability P1 in which the cases in the count range of the database are class A is as shown in the following equation (14) on the basis of the change in probability when the prevalence of the number of cases in the database changes from the prevalence a1 to the institutional prevalence (prior probability that the subject is group A) $a_2$. Here, $a_1$ is the prevalence in the database, $S_e$ is the sensitivity, and $S_p$ is the specificity.

$$P_1 = \frac{a_1 S_e}{a_1 S_e + (1-S_p)(1-a_1)} \tag{14}$$

$$a_1 = \frac{N_p}{N_n + N_p}, S_e = \frac{n_{p_1}}{N_p}, S_p = 1 - \frac{n_{n_1}}{N_n}$$

The odds ratio O1 is expressed by the following equation (15).

$$O_1 = \frac{P_1}{1 - P_1} = \frac{S_e}{1 - S_p} \frac{a_1}{1 - a_1} \quad (15)$$

When transformed, it becomes the following equation (16).

$$\frac{P_1}{1 - P_1} \frac{1 - a_1}{a_1} = \frac{S_e}{1 - S_p} \quad (16)$$

Even at the facility where the subject was examined, the "sensitivity/(1−specificity)" on the right side does not change, but the lesion probability for which the group is "A" is considered to change to $a_2$.

$$\frac{P_2}{1 - P_2} \frac{1 - a_2}{a_2} = \frac{S_e}{1 - S_p} = \frac{P_1}{1 - P_1} \frac{1 - a_1}{a_1} \quad (17)$$

$$\frac{P_2}{1 - P_2} = \frac{P_1}{1 - P_1} \frac{1 - a_1}{a_1} \frac{a_2}{1 - a_2} \quad (18)$$

When equation (18) is solved for $P_2$, it is expressed by the following equation (19). Here, k is defined as the following equation (20).

$$P_2 = \frac{kP_1/(1 - P_1)}{1 + kP_1/(1 - P_1)} \quad (19)$$

$$k = \frac{(1 - a_1)a_2}{a_1(1 - a_2)} \quad (20)$$

As a result, the corrected probability value and the confidence interval of the probability can be calculated as follows.

The predicted lesion probability $P_2$ when the prior probability is $a_2$ is obtained from the following equations (19) and (20). It is based on the lesion probability P1 when the prior probability is "$a_1$". The confidence interval when the prior probability is "$a_2$" is also acquired in the same manner.

(Variations of Prediction Measures)

The confidence interval calculating function 252 has mainly described an example of predicting lesion-presence or lesion-absence, but the present invention is not limited to that case. For example, the prediction measure can be applied in various ways depending on how the group is taken and the number of dimensions of the feature space. The prediction measures are shown below.

(I) Amount to calculate confidence interval (probability confidence interval)

(I-i) In the case of one variable: probability of lesion existence, probability of severity, probability of malignancy (I-ii) In the case of multiple variables: Probability of existence of each lesion, category classification, stage classification, probability of each lesion type, probability of each tissue type (I-iii) Prediction: Probability of effectiveness for each type of drug, probability of effectiveness of treatment (treatment)

(II) Group (II-i) Subject status (lesion-presence/lesion-absence, type)

(II-ii) Lesion-presence/lesion-absence, prediction of malignant/benign lesion, prediction of lesion category (category 0-5), lesion type classification (subtype, etc.), prediction of histological type (III) Forecast (III-i) Drug efficacy, therapeutic suitability (effect), prognosis (severe/not), occurrence of serious events, complete treatment/no treatment (IV) Number of attributes to be predicted (IV-i) 2 levels, 1 variable to multi-level, multiple variables (can be considered as classification into multiple groups by multiple variables)

Note that "multilevel, multiple variables" can be considered as classification into multiple groups by multiple variables. FIG. 31 is an example thereof.

As shown in FIG. 31, consider a case where the degree of liver fibrosis is represented by four groups (stages) of F0 to F4, and these groups are predicted by two variables (feature 1 and feature 2). According to the above-described embodiment, the counting range (shown by F0 to F4 in the graph) is set according to the measured values (feature 1 and feature 2) relating to the subject. The probability of F0 (average value), the probability of F1 (average value), . . . , the probability of F4 (average value), and their confidence intervals are calculated. For these confidence intervals, the upper limit, the lower limit, and the average value are plotted on the graph L32 of FIG. 32. For example, among the groups in which the upper limit of these probabilities exceeds the threshold value, the group having the highest degree of fibrosis is presented as a predicted result. In another example, the graph R32 of FIG. 32 presents a group in which the lower limit of the probability exceeds the threshold and the lower limit is the largest as the predicted result.

(Variation of Features)

The confidence interval calculating function 252 has mainly described an example of predicting lesion-presence or lesion-absence, but the present invention is not limited to that case. The feature may be as follows.

(V) Feature calculated by combining image processing (Vi) Circularity, sphericity (V-ii) average value, energy, entropy, contrast etc. (Texture Features)

(V-iii) Maximum diameter, volume (VI) Functional map statistics using conventional methods (VI-i) ADC (Apparent DIFFUSION Coefficient), FA (Fractional Anisotropy)

(VI-ii) rCBF (relative regional cerebral blood flow, rCBV (relative regional cerebral blood volume, MTT (mean transit time), TTP (time to peak))

(VI-iii) Ktrans, Kep (Tofts model)

(VII) Features determined by machine learning (VII-i) Neural network (VII-ii) Support vector machine (VII-iii) Random forest, extremely random tree (VII-iv) Logistic regression (VIII) In addition to the feature of the image, non-image data such as the R-R interval of the heartbeat, the result of the blood examination, and the presence or absence of symptoms may be added.

As an example of the feature of the image by machine learning, an example of using a hostile generation network (Generative Adversarial Networks) is given. It is known that using a hostile generation network (shown in FIG. 33), each unit in the middle layer, which is composed of a relatively small number of units, is learned to represent some feature of the image. The output of the intermediate unit thus acquired can be used as a feature.

In addition, various machine learning can be used for regression. FIG. 34 shows a case where SVM (Support vector machine) is used for regression. The regressed parameters can be used as features. Artificial neural networks and random trees can also be applied to regression. The explanation of the graphs U34, M34, and B34 is the same as the explanation of the graphs U15, M15, and B15 shown in FIG. 15, so the description thereof will be omitted.

(Example of Counting Range Optimization Method)

When predicting benign/malignant, the case of optimizing the counting range of the benign group will be described as an example. The case where the feature has two or more dimensions will be described with reference to FIGS. 35A and 35B.

As shown in FIG. 35A, first, one of the upper threshold/lower threshold of each feature is expanded by, for example, 1% with respect to the distribution width of the variable. There are two ways to increase the confidence interval upper limit/the confidence interval lower limit for one variable. Therefore, there is a possibility of "number of variables×2" as the method of expansion, and the one with the smallest confidence interval width is selected. This is repeated to gradually expand the threshold range. "The width of the confidence interval is small" means that the minimum value of the upper limit of the confidence interval is small when the minimum value of the upper limit of the confidence interval is acquired. At the same time, it is also taken into consideration that the difference between the measured values of the upper threshold and the lower threshold (the upper threshold width and the lower threshold width) is small.

Second, the same as above, but the threshold range is generalized and the range is represented by the bell-shaped integral weight function. The one with the smallest confidence interval is selected from among the many with slightly different parameters of the bell-shaped integral weight function.

As shown in FIG. 35B, thirdly, a large number of threshold ranges and integral weight functions including measured values are generated by random numbers. The horizontal axis plots the volume of the range, and the vertical axis plots the width of the confidence interval (upper and lower limits of the confidence interval). The minimum value of the envelope is acquired. In other words, the minimum value of the width of the confidence interval in the integration range generated by random numbers is acquired.

Fourth, the threshold range is divided by a constant width. In the case of one variable, it is divided into N, and in the case of m variable, it is divided into $N^m$ ranges. The width of the confidence interval is calculated by changing the number of divisions N of one variable.

Fifth, these are problems of optimizing the parameters of the counting range so as to minimize the confidence interval upper limit or maximize the confidence interval lower limit. In addition to the above, various optimization methods can be applied.

(Variation of Category Prediction)

In the example below, the "lower limit" represents the lower limit of the confidence interval or the maximum value of the lower limit of the confidence interval. The "upper limit" represents the upper limit of the confidence interval or the minimum value of the upper limit of the confidence interval.

As shown in FIG. 36, consider an example of predicting the categories of the lesion-absence group and the lesion-presence group. It is effective in cases where a subject whose "lesion-absence" is certain should be selected, where all subjects with a possibility of lesion should be selected, where a subject who has the possibility of having no lesion at all should be selected, and where a subject with certain lesion-presence should be selected.

With the display as shown in FIG. 36, a subject whose lesion can be ruled out can be selected without additional diagnosis. A subject that can be confirmed without additional diagnosis can be selected. Since "lower limit+upper limit=1", the two predictions on the left and right are equivalent.

FIG. 37 shows an example of predicting the lesion category of each group in the case of four groups of lesions A, B, C, and D. The lesions are differentiated by selecting the one with the highest possibility from multiple lesions.

FIG. 38 shows an example of predicting the category of each group of F1, F2, F3, and F4 other than the stages F0 and F0 of liver fibrosis. The most probable lesion is selected from multiple lesions and the lesions are differentiated. Since the lower part of FIG. 38 is equivalent to the lower part of FIG. 37, the notation is omitted.

FIGS. 39A and 39B show examples of predicting the effects of the drugs A, B, and C in categories, respectively. A drug that is effective for the subject is selected from multiple drugs, and the drug efficacy is predicted. Note that the same predicted method can also be used to predict a category for selecting a treatment method that is effective for a subject from among multiple treatment methods, and be used to predict the category for choosing a treatment with less complications.

FIGS. 40A and 40B show an example of predicting the incidence of each of the serious events as a category, and an example of predicting whether a good QOL (Quality of Life) can be recovered/maintained as a category from some viewpoints. The possibility of occurrence for each type of coronary event is predicted for each subject. At the same time, the possibility of recovering and maintaining good QOL is predicted.

(Example of Hierarchical Prediction)

Figure 41A:
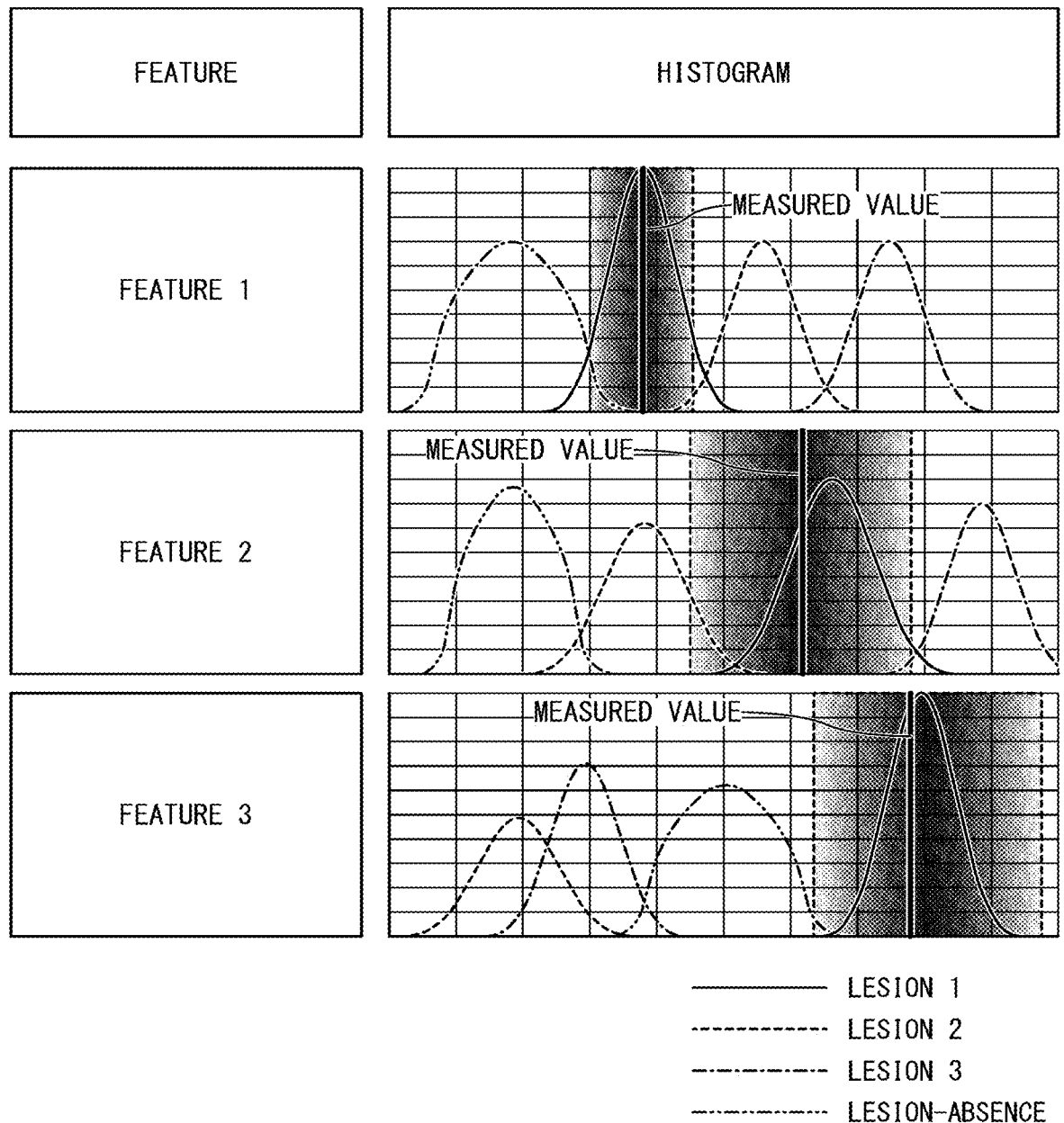
Figure 41C:
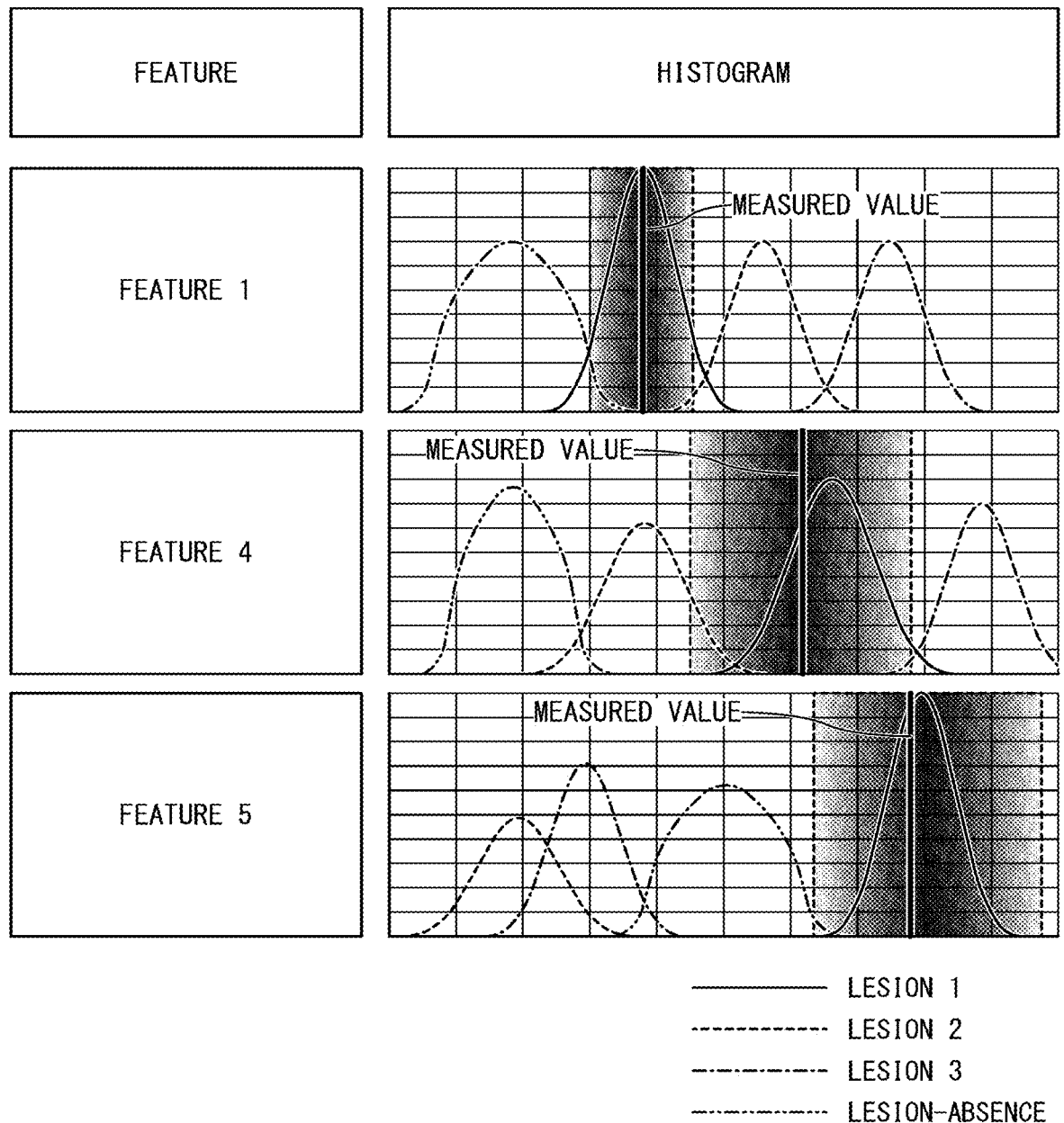
Figure 41D:
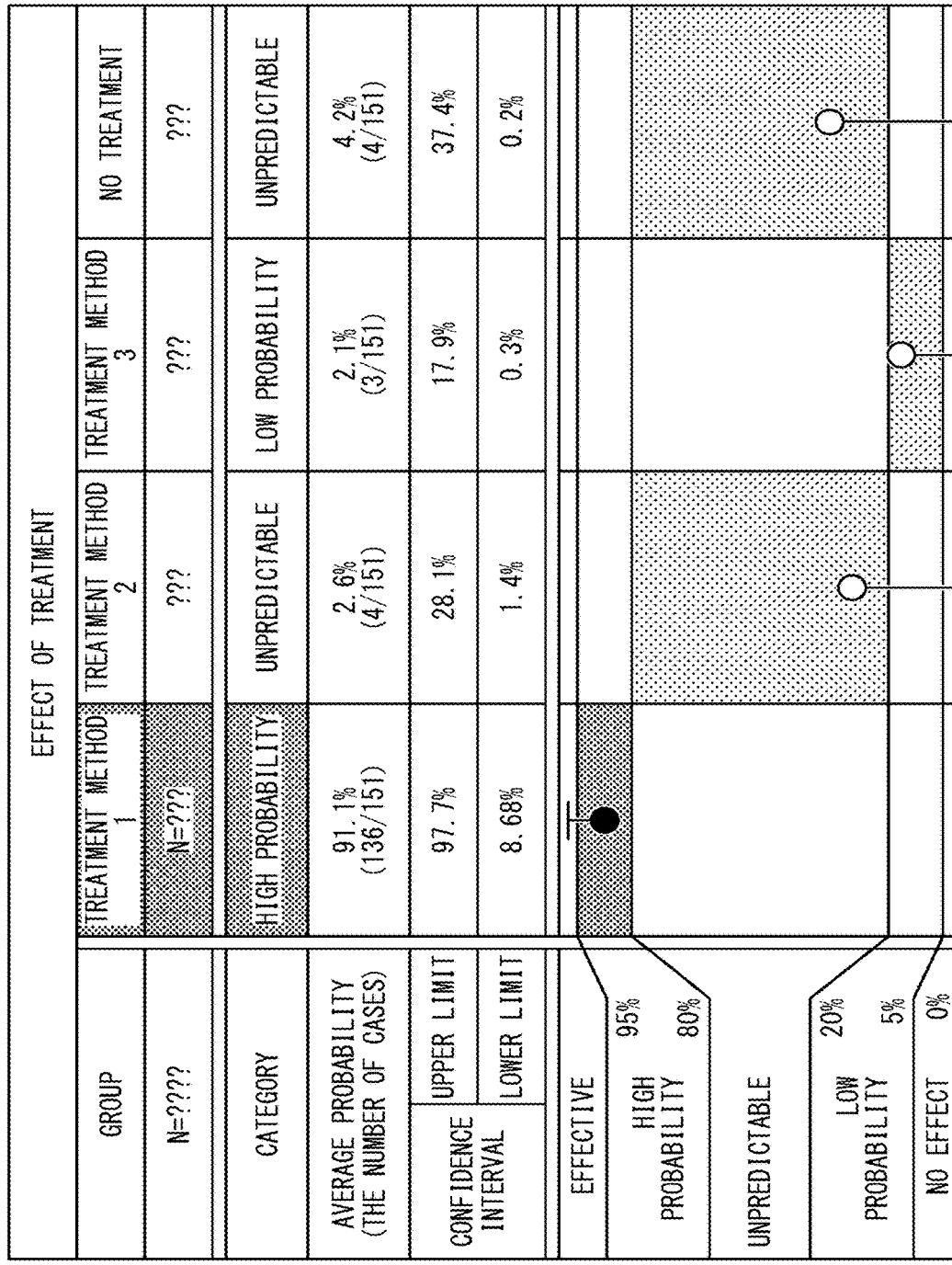
Figure 41E:
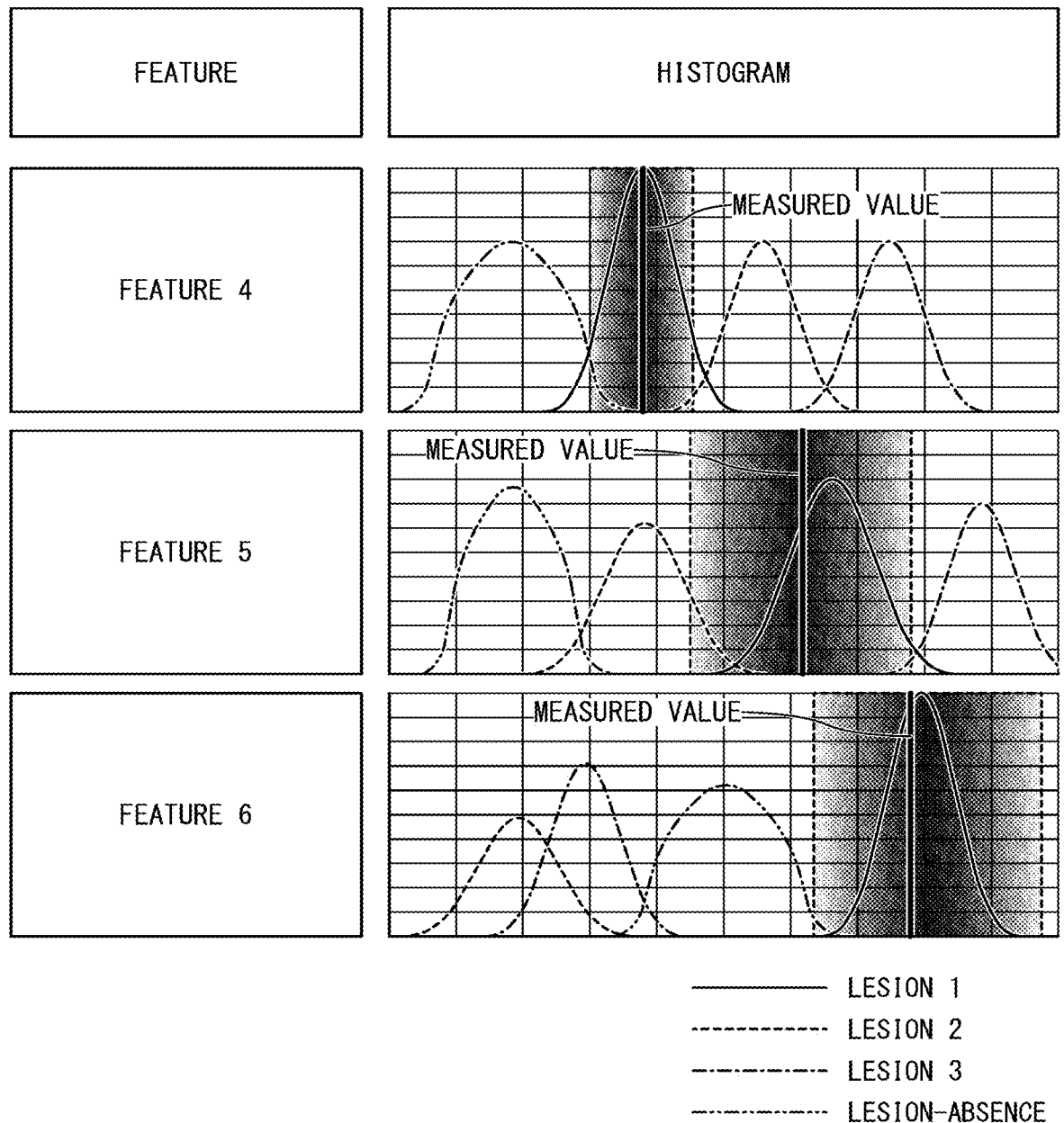
Figure 41F:
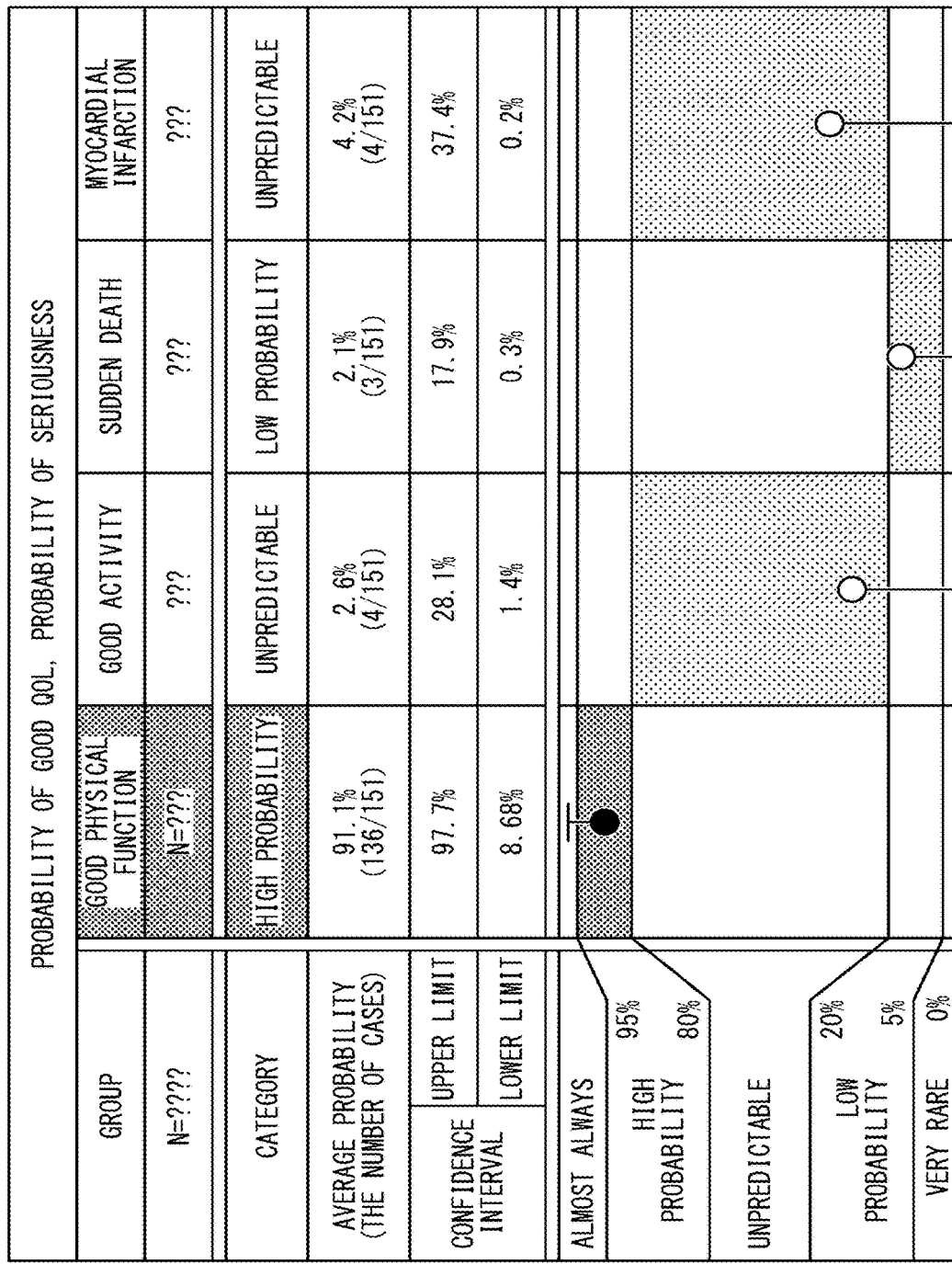

FIGS. 41A and 41B are examples of predicting the lesion probability in three layers. FIGS. 41C and 41D are examples of predicting the effect of treatment by each treatment method in three layers. FIGS. 41E and 41F are examples of predicting the probability of good QOL and the probability of aggravation in three layers. For such a prediction, the case data recorded in a complex manner is used. In the case data, image data or feature data, other non-imaging examination data, type of lesion, selected treatment method and its effect, good/bad of various QOLs, and occurrence of various seriousness is included.

In the prediction, first, all the cases are divided into four lesion groups (major classification), and the counting range of the feature is set. The number of cases in each major classification of lesions 1 to 4 is calculated. The confidence interval for the probability of each lesion predicts the possibility of each lesion by category. A major classification (type of lesion) is predicted using the confidence interval values (FIGS. 41A and 41B).

Next, the effect of each treatment method is predicted for the cases narrowed down to the cases in the predicted group (assumed to be predicted to be lesion 1). The cases of lesion 1 for which the major classification group was predicted are divided into eight groups (middle classification) of "effective of treatment method 1", "no effect of treatment method 1", "effective of treatment method 2", "no effect of treatment method 2", "effective of treatment method 3", "no effect of treatment method 3", "effective of treatment method 4", and "no effect of treatment method 4". By setting the counting range of the feature, the number of cases in each of these middle classification can be acquired. Regarding the presence or absence probability of the effect of the treatment method 1, the probability of the effect and the confidence interval thereof are acquired based on the number of cases of "effective of the treatment method 1" and "no effect of the treatment method 1". Similarly, for the treatment methods 2 to 4, the probability of effectiveness and the confidence interval are required. Based on these, the possibility of effectiveness is predicted by category. The middle classification is predicted using the confidence interval values (FIGS. 41C and 41D). In the example shown in FIG. 41D, it is assumed that the treatment group 1 is selected.

Finally, the probability of good QOL and the probability of aggravation are predicted for the cases in which the major classification is "lesion 1" and the middle classification is "effective of treatment method 1". Alternatively, there may be a configuration in which "no effect of treatment method 2" is added to the middle classification. These target cases are further divided into a "good physical function" group and a "poor physical function" group (small classification 1). In addition, the same target cases are divided into a "good activity" group and a "poor activity" group (small classification 2). Further, the same target cases are divided into a "sudden death" group and a "non-sudden death" group (small classification 3). Further, the same target cases are divided into a "myocardial infarction" group and a "non-myocardial infarction" group (small classification 4). The number of cases in each of these sub-taxa is acquired by setting the counting range of the feature. The probability of "good physical function" and the confidence interval of the probability are acquired from the number of cases of "good physical function" and the number of cases of "poor physical function". Similarly, the probability and confidence interval of "good activity", the probability and confidence interval of "sudden death", and the probability and confidence interval of "myocardial infarction" are acquired. The values of these confidence intervals are used to predict the categories of subclasses 1 to 4 (FIGS. 41E and 41F). Regarding the probability of good QOL and the probability of aggravation, for each of the sub-categories 1 to 4, it is predicted in each of the sub-categories 1 to 4 whether the QOL is good or poor, or whether or not the aggravation occurs.

(Example of GUI that Sets and Changes the Counting Range)

In the initial display of the histogram, the counting range acquired by optimization is displayed as shown in FIG. 42. In the graph shown in FIG. 42, the range between the value of the feature marked with a circle and the value of the feature marked with a square is the counting range. When the operator operates the circle mark and the square mark with the mouse as the input interface 13, the range is expanded or narrowed. As a result, the probability of belonging to the group and its confidence interval are recalculated and the updated values are displayed.

In the graph shown in FIG. 43, the upper limit and the lower limit of the confidence interval when the counting range is expanded or narrowed are displayed in advance. Therefore, before the operator actually changes the counting range, it is possible for the operator to know what the recalculated confidence interval lower limit and upper limit will be. Since it is possible to determine how to change without trial and error, the operation time can be shortened.

FIG. 44 shows a histogram display when the feature is three variables. In the case of multiple variables, only one of the multiple dimensions is displayed, and the other dimensions fix the counting range.

As shown in FIGS. 42 to 44, a graph showing changes in the predicted positive rate with respect to the upper and lower threshold values of the confidence interval is displayed for each feature based on the automatically determined threshold range. Then, when the operation of changing the threshold value is performed, the graph is updated.

According to at least one embodiment described above, it is possible to present the operator with appropriate data for performing an efficient diagnosis.

While certain embodiments have been described, these embodiments have been presented by way of example only, and are not intended to limit the scope of the inventions. Indeed, the novel methods and systems described herein may be embodied in a variety of other forms; furthermore, various omissions, substitutions, changes, and combinations of embodiments in the form of the methods and systems described herein may be made without departing from the spirit of the inventions. The accompanying claims and their equivalents are intended to cover such forms or modifications as would fall within the scope and spirit of the inventions.

What is claimed is:

1. A medical data processing apparatus, comprising: processing circuitry configured to calculate a probability that received target image data has a lesion and a confidence interval indicating a reliability of the calculated probability; and output data on the lesion based on the calculated probability and the confidence interval of the probability, wherein the processing circuitry is further configured to acquire statistical data on a frequency of lesions aggregated based on characteristics of a plurality of image data, calculate the probability that the target image has the lesion and the confidence interval indicating the reliability of the probability, based on an arbitrary range including a measured value of the target image data using a frequency distribution indicated by the acquired statistical data, and output the data on the lesion based on the calculated probability and the confidence interval of the probability.

2. The medical data processing apparatus according to claim 1, wherein the processing circuitry is further configured to calculate a range of a feature to which a feature of the target image data belongs as a counting range.

3. The medical data processing apparatus according to claim 2, wherein the processing circuitry is further configured to: acquire a number of cases belonging to the counting range for each group in the plurality of the image data, and calculate an average value of probabilities of belonging and the a confidence interval for at least one group.

4. The medical data processing apparatus according to claim 1, wherein the processing circuitry is further configured to output, as the data on the lesion, a predicted result regarding the lesion of the target image data based on a relationship between the calculated probability and the confidence interval of the calculated probability.

5. The medical data processing apparatus according to claim 4, wherein the processing circuitry is further configured to output a determination result according to a prediction condition of the confidence interval.

6. The medical data processing apparatus according to claim 1, wherein the processing circuitry is further configured to output, as the data on the lesion, the calculated probability, and the confidence interval of the calculated probability.

7. The medical data processing apparatus according to claim 1, wherein the processing circuitry is further configured to collect the statistical data on the frequency of the lesion based on the characteristics of the plurality of image data.

8. The medical data processing apparatus according to claim 1, wherein the processing circuitry is further configured to classify the received target image data into a plurality of image patterns, and calculate a confidence interval indicating the lesion probability of each image pattern as a classification reasonability scale, extract a part of the image patterns from which the lesion can be easily identified from the plurality of image patterns based on the classification reasonability scale of each image pattern of the plurality of image patterns, and preferentially display a part of the image patterns on a display.

9. The medical data processing apparatus according to claim 8, wherein the processing circuitry is further configured to input the received target image data into a trained model that generates the classification reasonability scale based on the received target image data, thereby generating the classification reasonability scale.

10. The medical data processing apparatus according to claim 8, wherein the processing circuitry is further configured to set a region of interest (ROI) of the target image data, and classify the target image data into a plurality of image patterns based on the ROI.

11. The medical data processing apparatus according to claim 8, wherein the processing circuitry is further configured to display a name of a part of the image patterns as character data.

12. The medical data processing apparatus according to claim 8, wherein the processing circuitry is further configured to use a predicted benign rate or a width of the confidence interval indicating a predicted malignancy rate as the classification reasonability scale.

13. The medical data processing apparatus according to claim 8, wherein the processing circuitry is further configured to: predefine a specific image pattern to be displayed as a criterion regardless of a priority, display the specific image pattern on the display, and preferentially display the part of the image patterns on the display.

14. The medical data processing apparatus according to claim 8, wherein the processing circuitry is configured to the probability of having the lesion is a benign probability or a malignant probability of mass.

15. A medical data processing method comprising: calculating a probability that received target image data has a lesion and a confidence interval indicating a reliability of the calculated probability, and outputting data on the lesion based on the calculated probability and the confidence interval of the probability, wherein the method is further comprises: acquire statistical data on a frequency of lesions aggregated based on characteristics of a plurality of image data, calculating the probability that the target image has the lesion and the confidence interval indicating the reliability of the probability, based on an arbitrary range including a measured value of the target image data using a frequency distribution indicated by the acquired statistical data, and outputting the data on the lesion based on the calculated probability and the confidence interval of the probability.

16. A non-transitory computer readable medium storing a program that when executed by circuitry, causes the circuitry to perform a method comprising: calculating a probability that received target image data has a lesion and a confidence interval indicating a reliability of the calculated probability, and outputting data on the lesion based on the calculated probability and the confidence interval of the probability, wherein the method further comprises to acquiring statistical data on a frequency of lesions aggregated based on characteristics of a plurality of image data, calculating the probability that the target image has the lesion and the confidence interval indicating the reliability of the probability, based on an arbitrary range including a measured value of the target image data using a frequency distribution indicated by the acquired statistical data, and outputting the data on the lesion based on the calculated probability and the confidence interval of the probability.

* * * * *